United States Patent
Goodwin, Jr.

(10) Patent No.: US 7,704,325 B2
(45) Date of Patent: Apr. 27, 2010

(54) CRYSTAL FORMING APPARATUS AND METHOD FOR USING SAME

(75) Inventor: Richard H. Goodwin, Jr., Bethesda, MD (US)

(73) Assignee: Neuro Probe Incorporated, Gaithersburg, MD (US)

( * ) Notice: Subject to any disclaimer, the term of this patent is extended or adjusted under 35 U.S.C. 154(b) by 7 days.

(21) Appl. No.: 11/968,422

(22) Filed: Jan. 2, 2008

(65) Prior Publication Data

US 2008/0134963 A1    Jun. 12, 2008

Related U.S. Application Data

(60) Division of application No. 10/914,201, filed on Aug. 10, 2004, now Pat. No. 7,332,029, which is a continuation-in-part of application No. 10/765,053, filed on Jan. 28, 2004, now Pat. No. 7,014,706, which is a division of application No. 10/345,217, filed on Jan. 16, 2003, now Pat. No. 6,767,401.

(60) Provisional application No. 60/349,252, filed on Jan. 18, 2002.

(51) Int. Cl.
 *C30B 35/00* (2006.01)
(52) U.S. Cl. .............. 117/206; 117/200; 117/201; 117/202; 117/204; 117/900; 23/295 R; 422/99; 422/100; 422/245.1
(58) Field of Classification Search .............. 23/295 R; 117/200, 201, 202, 204, 206, 900; 422/99, 422/100, 245.1; 435/235.1
See application file for complete search history.

(56) References Cited

U.S. PATENT DOCUMENTS

| | | | |
|---|---|---|---|
| 2,561,339 A | 7/1951 | Chediak |
| 3,055,808 A | 9/1962 | Henderson |
| 3,107,204 A | 10/1963 | Brown et al. |
| 3,165,450 A | 1/1965 | Scheidt |
| 4,012,288 A | 3/1977 | Lyman et al. |
| 4,299,921 A | 11/1981 | Youssef |
| 4,599,314 A | 7/1986 | Shami |
| 4,599,315 A | 7/1986 | Terasaki et al. |
| 4,682,891 A | 7/1987 | de Macario et al. |
| 4,770,856 A | 9/1988 | Uthemann et al. |
| 4,822,741 A | 4/1989 | Banes |

(Continued)

FOREIGN PATENT DOCUMENTS

WO    WO 00/60345    10/2000

OTHER PUBLICATIONS

European Patent Office Examination Report, Feb. 19, 2008.

*Primary Examiner*—Felisa C Hiteshew
(74) *Attorney, Agent, or Firm*—Plumsea Law Group, LLC

(57) ABSTRACT

A crystal forming apparatus and method for using the apparatus, the method including depositing a precipitant solution in a site, incubating the site, during which time volatile vapor evaporates from the precipitant solution and accumulates in the site, and pumping the accumulated volatile vapor away from the site. An exemplary apparatus includes a sealed site except for a vent on the sealed site. In one embodiment, the vent is a passive vent that inhibits vapor diffusion out of the site. In another embodiment, the vent is an active vent that opens in response to a pressure differential. The present invention accelerates and controls the crystal growth process by pumping volatile vapor away from the sealed site.

39 Claims, 26 Drawing Sheets

SECTION 5C-5C

U.S. PATENT DOCUMENTS

| | | |
|---|---|---|
| 4,886,646 A | 12/1989 | Carter et al. |
| 5,013,531 A | 5/1991 | Snyder et al. |
| 5,096,676 A | 3/1992 | McPherson et al. |
| 5,221,410 A | 6/1993 | Kushner et al. |
| 5,284,753 A | 2/1994 | Goodwin, Jr. |
| 5,332,905 A | 7/1994 | Brooker |
| 5,723,943 A | 3/1998 | Brooker et al. |
| 6,027,565 A | 2/2000 | Bugg et al. |
| 6,141,131 A | 10/2000 | Brooker et al. |
| 6,147,798 A | 11/2000 | Brooker et al. |
| 6,258,331 B1 | 7/2001 | Sanjoh |
| 6,296,673 B1 | 10/2001 | Santarsiero et al. |
| 6,406,903 B2 | 6/2002 | Bray et al. |
| 6,447,726 B1 | 9/2002 | Delucas et al. |
| 6,468,736 B2 | 10/2002 | Brooker |
| 6,579,358 B2 | 6/2003 | Delucas et al. |
| 6,592,824 B2 | 7/2003 | Delucas et al. |
| 6,623,708 B2 | 9/2003 | Delucas et al. |
| 6,761,861 B2 | 7/2004 | Rouleau et al. |
| 6,767,401 B2 | 7/2004 | Goodwin, Jr. |
| 2002/0031789 A1 | 3/2002 | Brooker |
| 2004/0071599 A1 | 4/2004 | Rusch et al. |

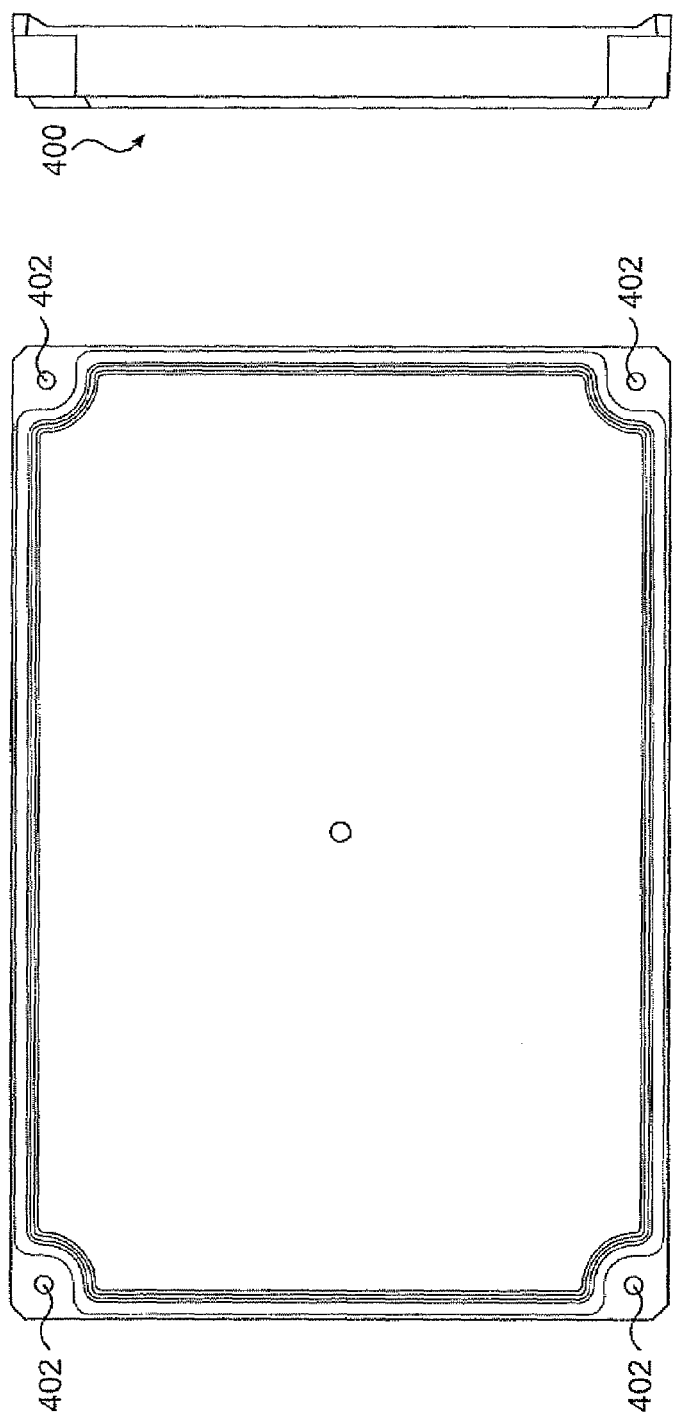
*FIG. 4A*
*FIG. 4C*
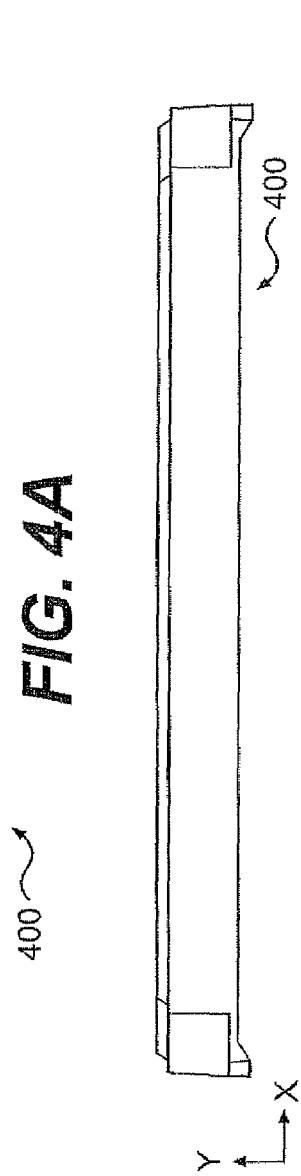
*FIG. 4B*

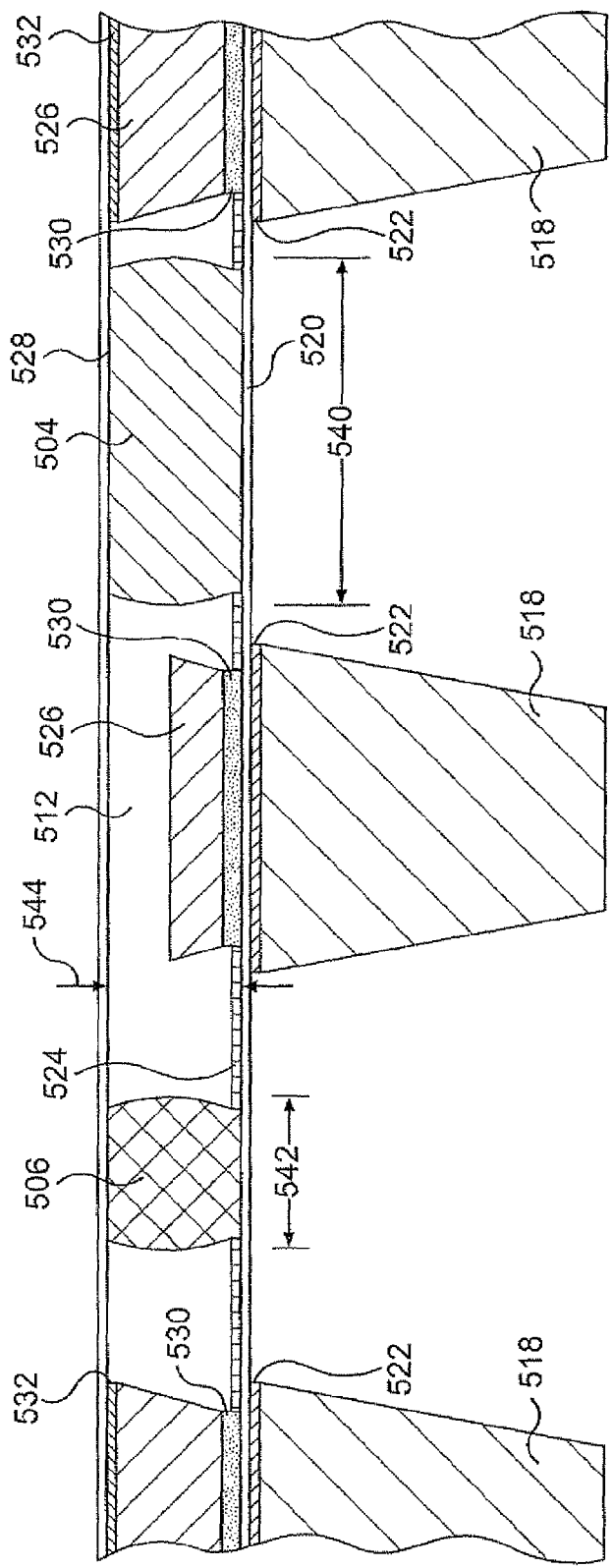

SECTION 5D-5D

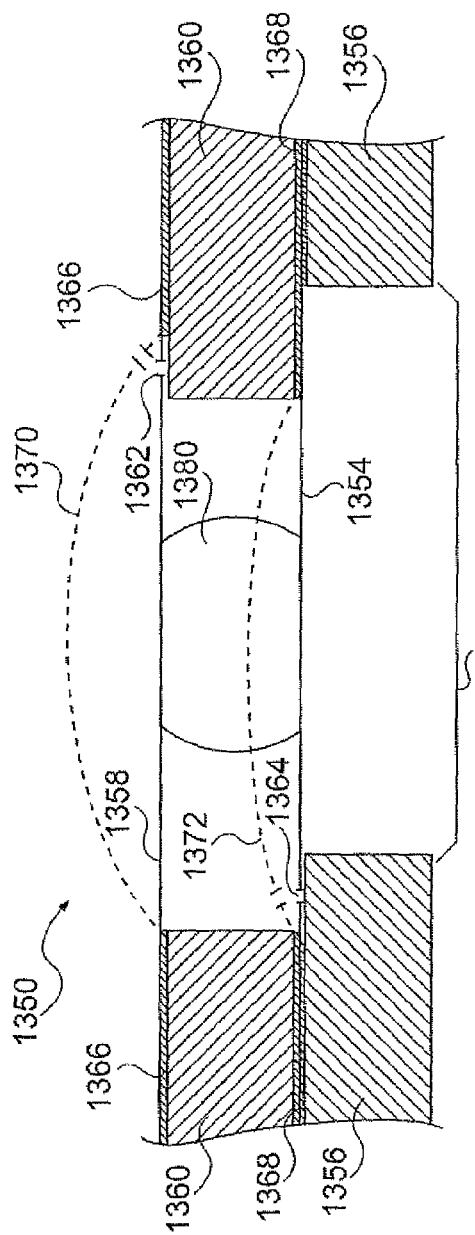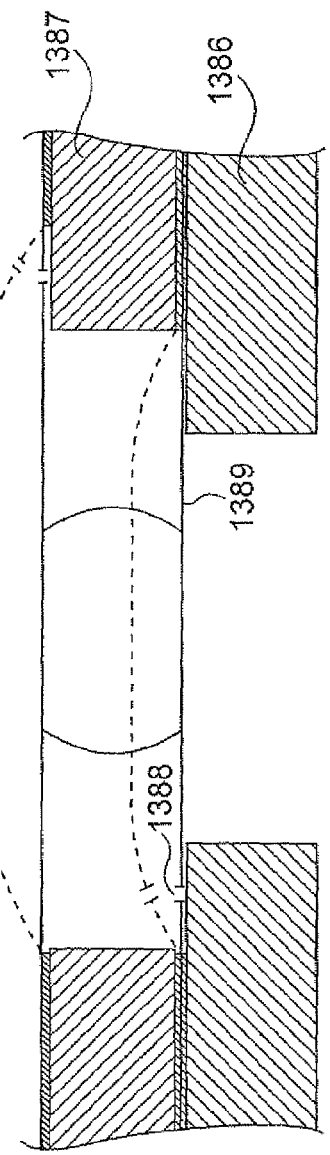
FIG. 13B
FIG. 13C

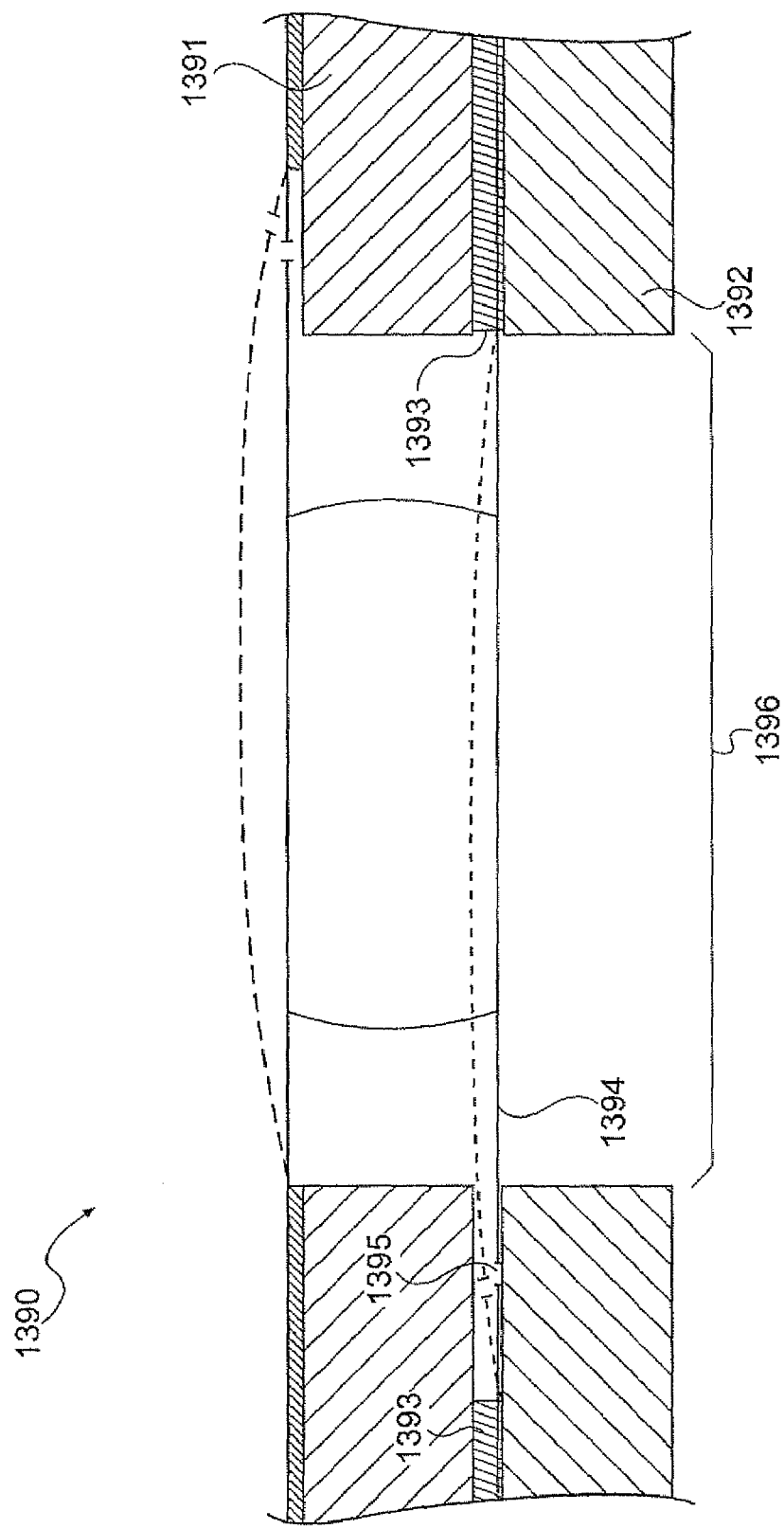

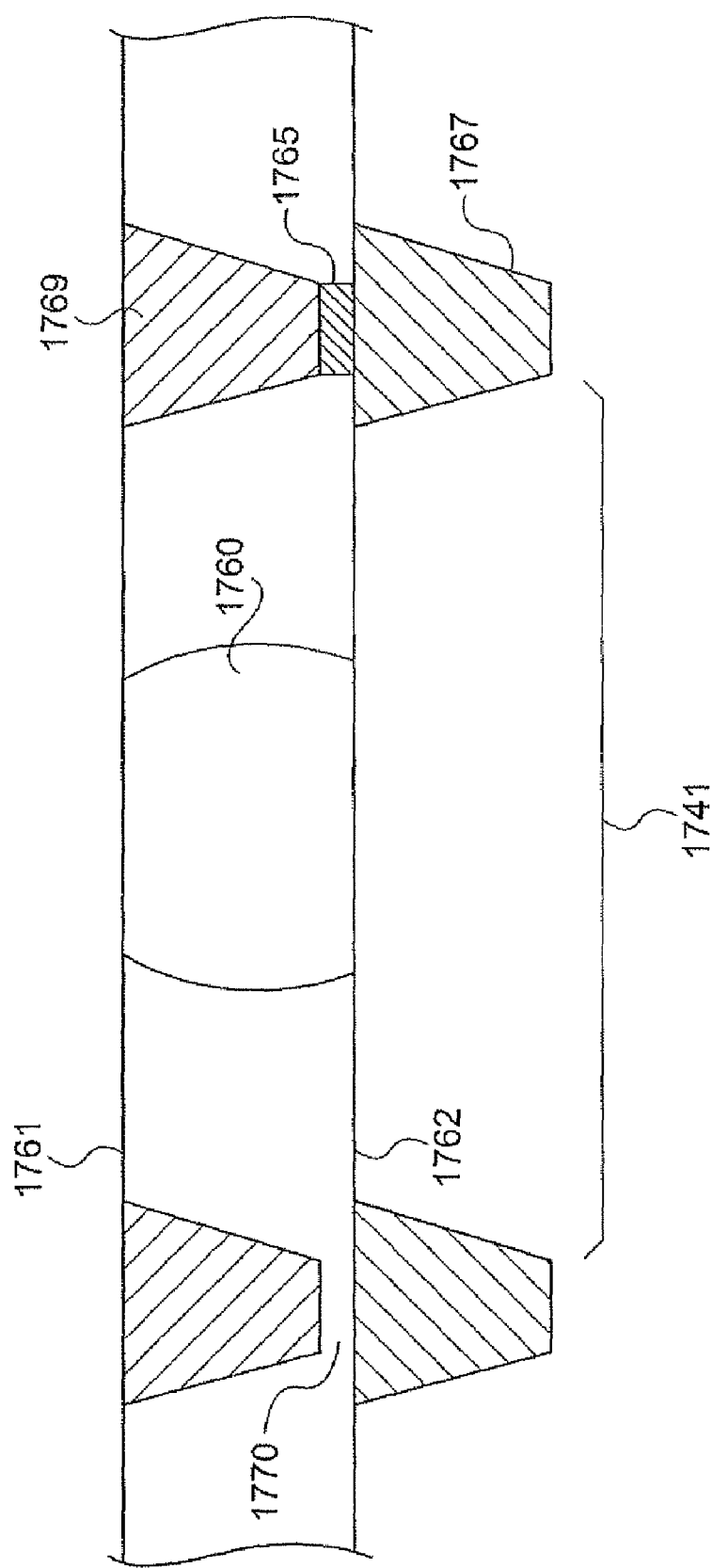

CRYSTAL FORMING APPARATUS AND METHOD FOR USING SAME

This application is a division of U.S. application Ser. No. 10/914,201, filed Aug. 10, 2004, now U.S. Pat. No. 7,332,029 which is a continuation-in-part of U.S. application Ser. No. 10/765,053, filed Jan. 28, 2004, now U.S. Pat. No. 7,014,706, which is a division of U.S. application Ser. No. 10/345,217, filed Jan. 16, 2003, now U.S. Pat. No. 6,767,401, which claims the benefit of U.S. Provisional Application No. 60/349,252, filed Jan. 18, 2002, all of which are herein incorporated by reference in their entirety.

BACKGROUND

1. Field of the Invention

The present invention relates generally to crystallization chambers and to apparatus and methods for conducting multiple crystal forming experiments.

2. Background of the Invention

There remains a need in the prior art for a fast, reliable, and cost-effective crystallization apparatus that enables a researcher to conduct multiple crystal forming experiments, with minimal set-up effort and small amounts of sample solutions. Small sample size is particularly important in protein crystallization, where the protein is scarce and very expensive, and one kind of protein is used with, for example, two thousand different crystal growing solutions to ascertain which ones promote crystal growth. In the specific context of crystallization apparatus that use multiple-well microplates (see, for example, U.S. Pat. No. 5,221,410 to Kushner et al., which is incorporated by reference herein), there remains a need for a crystallization apparatus that is fast, reliable, and easily automated, yet can also be used with manual methods. Specifically, there is a need for an apparatus that is compatible with robotic systems that dispense small volumes of sample solutions and detect the presence of very small crystals.

SUMMARY OF THE INVENTION

According to a representative embodiment, the present invention is a crystallization apparatus, as well as a method for using the apparatus, that provides a film on which to place sample solutions. In addition to the film, the apparatus can include other components on which complementary solutions can be placed, and which, together with the film, form a plurality of independent crystallization environments or sites. The apparatus and method can be adapted to perform, for example, hanging drop, sitting drop, or sandwich drop vapor diffusion crystallization. As used herein, sandwich drop refers to a drop that contacts two surfaces, such as opposing upper and lower surfaces—although the apparatus can also, of course, be oriented differently, such as vertically in which case the surfaces are vertical as opposed to horizontal.

An embodiment of the present invention provides a crystal forming apparatus that includes a plate and a film. The plate has a site adapted to hold a screening solution. The film is adjacent to the plate. The film seals the site and is adapted to contain a precipitant solution inside the site with an air gap between the screening solution and the precipitant solution.

In an aspect of this embodiment, the plate is a microplate and the site is a well of the microplate. A sample of screening solution can be disposed in the well and a sample of precipitant solution can be held by the film and suspended over the sample of screening solution.

In another aspect of this embodiment, the plate is a second film supported by a first support structure. The first film is supported by a second support structure. The second support structure is disposed on top of the second film. The first film is disposed on a side of the second support structure opposite the second film. The second support structure and the first film are adapted to seal the site. The second support structure is, for example, a lattice having a first through-hole, a second through-hole, and a passage connecting the first through-hole to the second through-hole.

Another embodiment of the present invention provides a method for forming crystals that includes depositing a screening solution into a well of a microplate, depositing a precipitant solution onto a film, and placing the film over the well such that the precipitant solution is suspended over the screening solution.

Another embodiment of the present invention provides a method for forming crystals that includes depositing a screening solution onto a first film, depositing a precipitant solution onto the first film proximate to the screening solution, sealing the screening solution and the precipitant solution within a site between the first film and a second film, and providing, within the site, an air gap between the screening solution and the precipitant solution.

Another embodiment of the present invention provides a method for forming crystals that includes depositing a precipitant solution in a site, incubating the site, during which time volatile vapor (e.g., water or alcohol) evaporate from the precipitant solution and accumulate in the site, and removing the accumulated volatile vapor from the site. An exemplary apparatus includes a sealed site except for a vent on the sealed site. In one embodiment, the vent is a passive vent that is open, but that inhibits vapor diffusion out of the site. In another embodiment, the vent is an active vent that is normally closed when the pressure inside the site is substantially equal to the outside pressure, but that opens to allow passage of volatile vapor out and ambient air or gas in the site when the inside pressure and the outside pressure are substantially different. The present invention accelerates and controls the initiation and continuation of the crystal growth process by pumping volatile vapor away from the sealed site and thereby increasing the concentration of the protein in the precipitant solution.

BRIEF DESCRIPTION OF THE DRAWINGS

FIG. 4A is a schematic diagram of an exemplary lid for a crystallization apparatus, according to an embodiment of the present invention.

FIGS. 4B and 4C are schematic diagrams of side views of the exemplary lid shown in FIG. 4A.

FIG. 5C is a schematic diagram of a cross-sectional view of the crystallization apparatus of FIG. 5A along line 5C-5C.

FIGS. 13B, 13C, and 13D are schematic diagrams of cross-sectional side views of exemplary crystallization apparatus having a crystallization site with an active valve provided by film openings that are closed by structures of the crystallization apparatus and opened by differential pressure, according to an embodiment of the present invention.

FIG. 17B is a schematic diagram of a cross-sectional view of the crystallization site along line A-A of FIG. 17A, according an embodiment of the present invention.

DETAILED DESCRIPTION OF THE INVENTION

An embodiment of the crystallization apparatus of the present invention includes a microplate with greased rims and a film bonded to a frame. The frame is mounted on top of the microplate, such that the film contacts the greased rims of the microplate to create individual, independent environments in which crystals may form. In a further embodiment, the apparatus includes a lid placed over the frame to protect the frame, film, and microplate, and to allow one apparatus to be stacked on top of another.

Figure 1A:
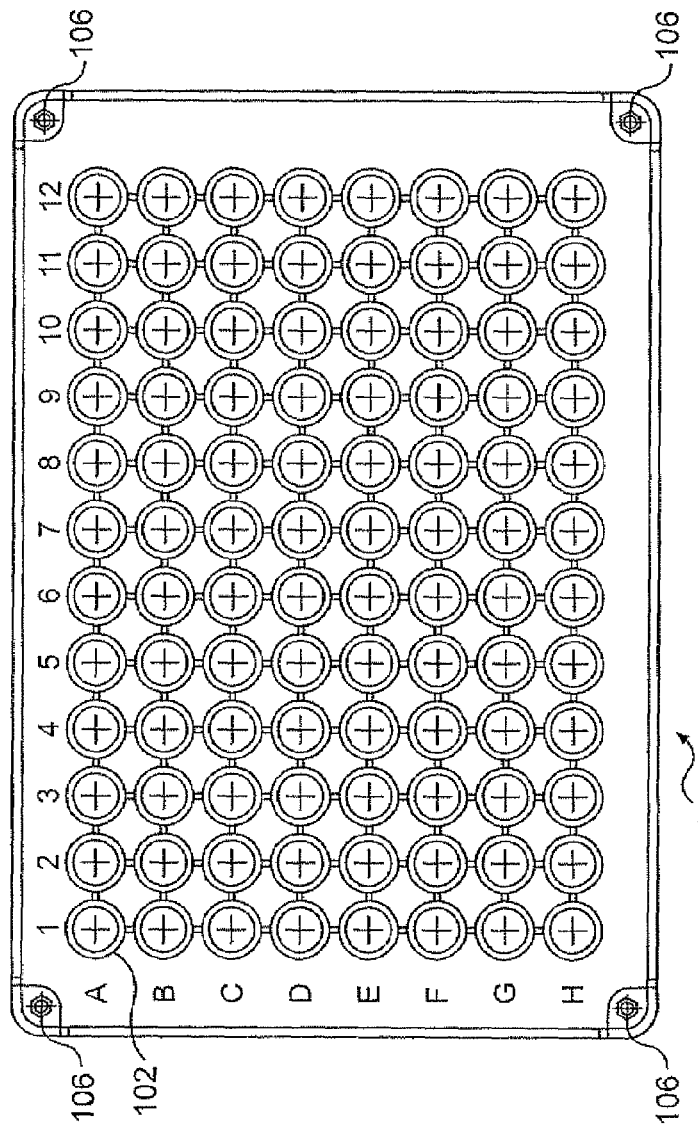
FIG. 1A is a schematic diagram of a top view of an exemplary microplate of a crystallization apparatus, according to an embodiment of the present invention.
Figure 1B:
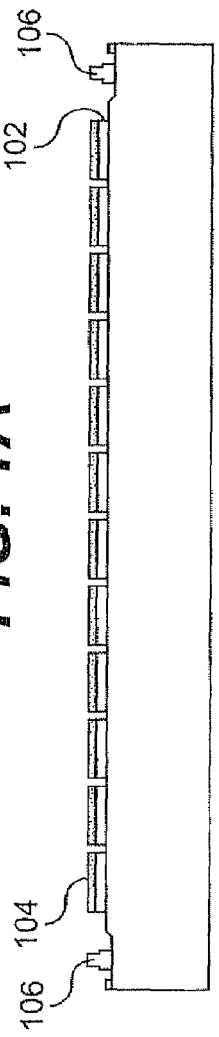
FIGS. 1B and 1C are schematic diagrams of side views of the exemplary microplate shown in FIG. 1A.
Figure 1C:
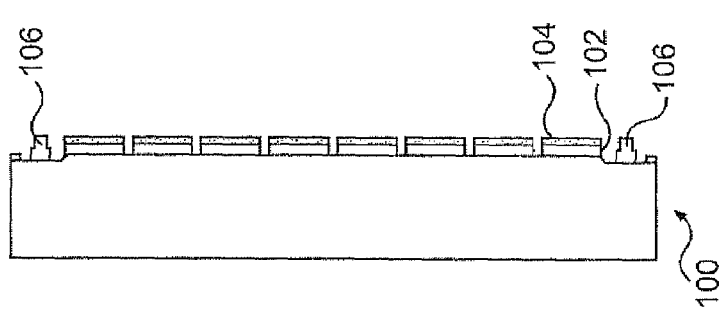

FIGS. 1A, 1B, and 1C illustrate a microplate 100, according to an embodiment of the present invention. As shown, microplate 100 has rims 102, each of which is covered with a layer of grease 104. In a specific embodiment, the microplate 100 is a polystyrene 96-well microplate with greased rims. Grease 104 is any material suitable for sealing a gap between a film and rims 102. Grease 104 could be, for example, a malleable sealant with adhesive properties. Grease 104 could also be a gasket with adhesive properties. In an alternative embodiment, if the materials of a film and the rims 102 can contact each other and provide an adequate seal, then grease 104 is not needed.

Microplate 100 also has reference pins 106 for aligning and retaining a frame. Although, in this example, microplate 100 has four pins 106, microplate 100 could, of course, have as many pins (at least two, but could also be three, four, or more) as needed to properly align and retain a frame. In addition, microplate 100 could use other alignment/retention means, such as adhesives, interference fits, or interlocking or interlocating components or features.

Figure 2:
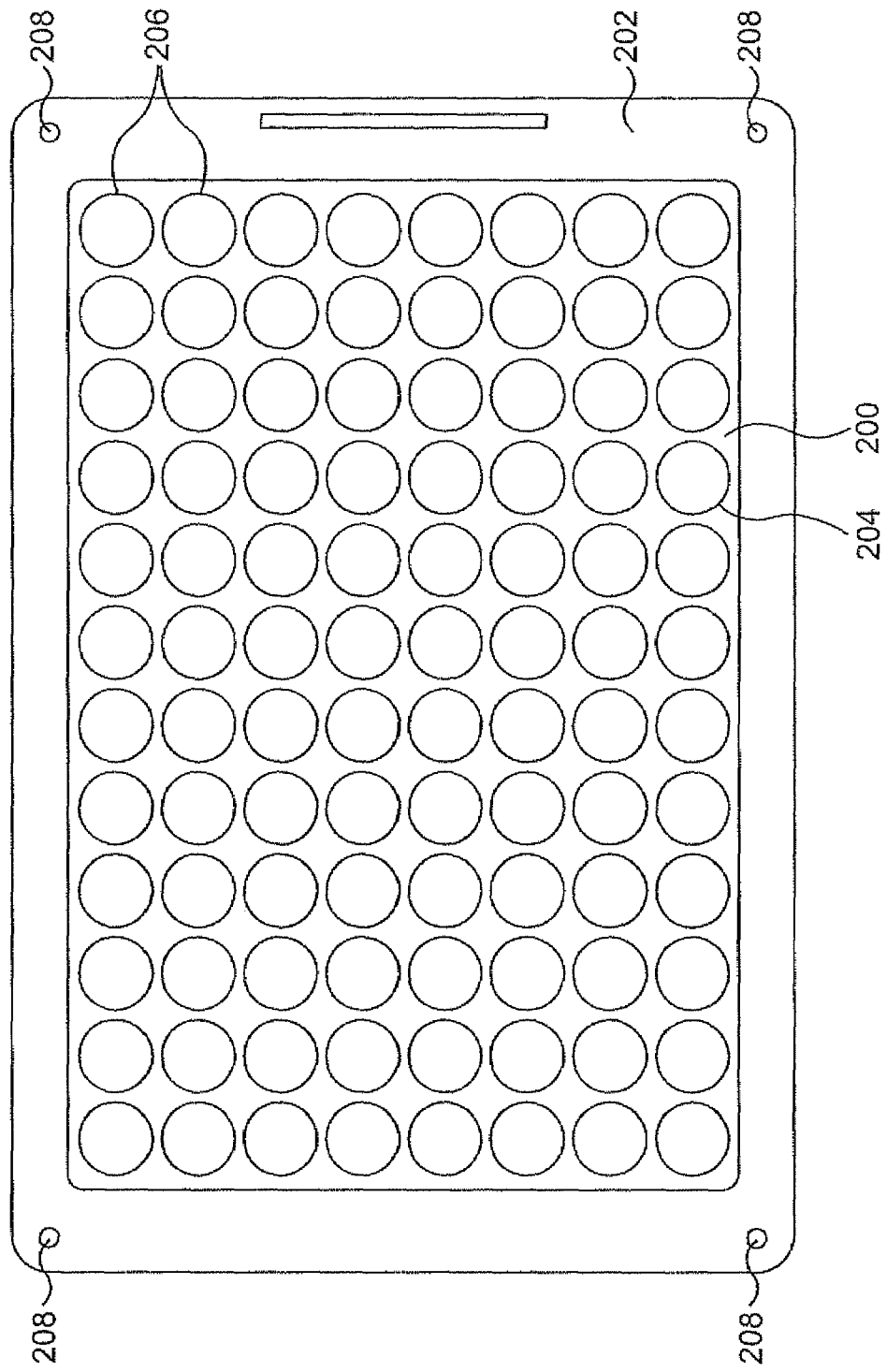
FIG. 2 is a schematic diagram of an exemplary film and frame of a crystallization apparatus, according to an embodiment of the present invention.

FIG. 2 illustrates a film 200 bonded to a frame 202, according to an embodiment of the present invention. In a specific embodiment, film 200 is Teflon™, e.g., 0.001 inch Teflon™. As shown in FIG. 2, film 200 preferably has marked positioning rings 204, which are, for example, silk-screened in ink on top of film 200. These positioning rings 204 correspond to the well configuration of the microplate on which film 200 and frame 202 are to be mounted, and help guide placement of precipitant solutions onto film 200. Markings (e.g., in the example shown in FIG. 2, numbers and letters) assist in monitoring the particularities of each site.

As used herein, a precipitant solution refers to a solution of a compound that is to be crystallized, and a screening solution refers to a solution that may or may not promote crystallization. For example, in the context of protein crystallization screening, in which a goal is to identify solutions (from among many possible screening solutions) that facilitate the formation of protein crystals, a protein solution, which is relatively concentrated, is typically mixed 50:50 with each of the possible screening solutions. This 50:50 solution is the precipitant solution and is placed in a site along with its corresponding 100% screening solution, where vapor diffusion then begins.

Positioning rings 204 provide multiple crystallization sites. The terms "test site" or "site" are used herein to refer to a delineated spot on a film where a precipitant solution is positioned. The position of the sites is defined by, for example, a pattern 206 on film 200. The pattern 206, which identifies the locations of the sites, may be formed by ink imprinted on the film, may be a patterned film of plastic or silicone, or may be defined by a patterned hydrophobic coating silk-screened or otherwise applied to the film. The coating may simply define the locations of the test sites, or it may also function as a hydrophobic barrier, spatially restricting a precipitant solution.

Frame 202 is rigid enough to keep film 200 flat, to ensure that film 200 adequately covers each well of microplate 100 when the components are assembled (described in more detail below). While keeping film 200 flat, at the same time, frame 202 can allow film 200 some degree of movement (e.g., by having slack, flexibility, or elasticity) in a direction generally perpendicular (normal) or at an angle to the face of film 200. Frame 202 includes reference holes 208, which engage reference pins 106 of microplate 100 to align the components during assembly. Frame 202 can be any formable material, such as plastic, stainless steel, or aluminum. In a specific embodiment, frame 202 is an anodized aluminum frame. Film 200 can be attached to frame 202 by any suitable fastening means, including glue, adhesives, heat seals, ultrasonic seals, or mechanical means.

Figure 3A:
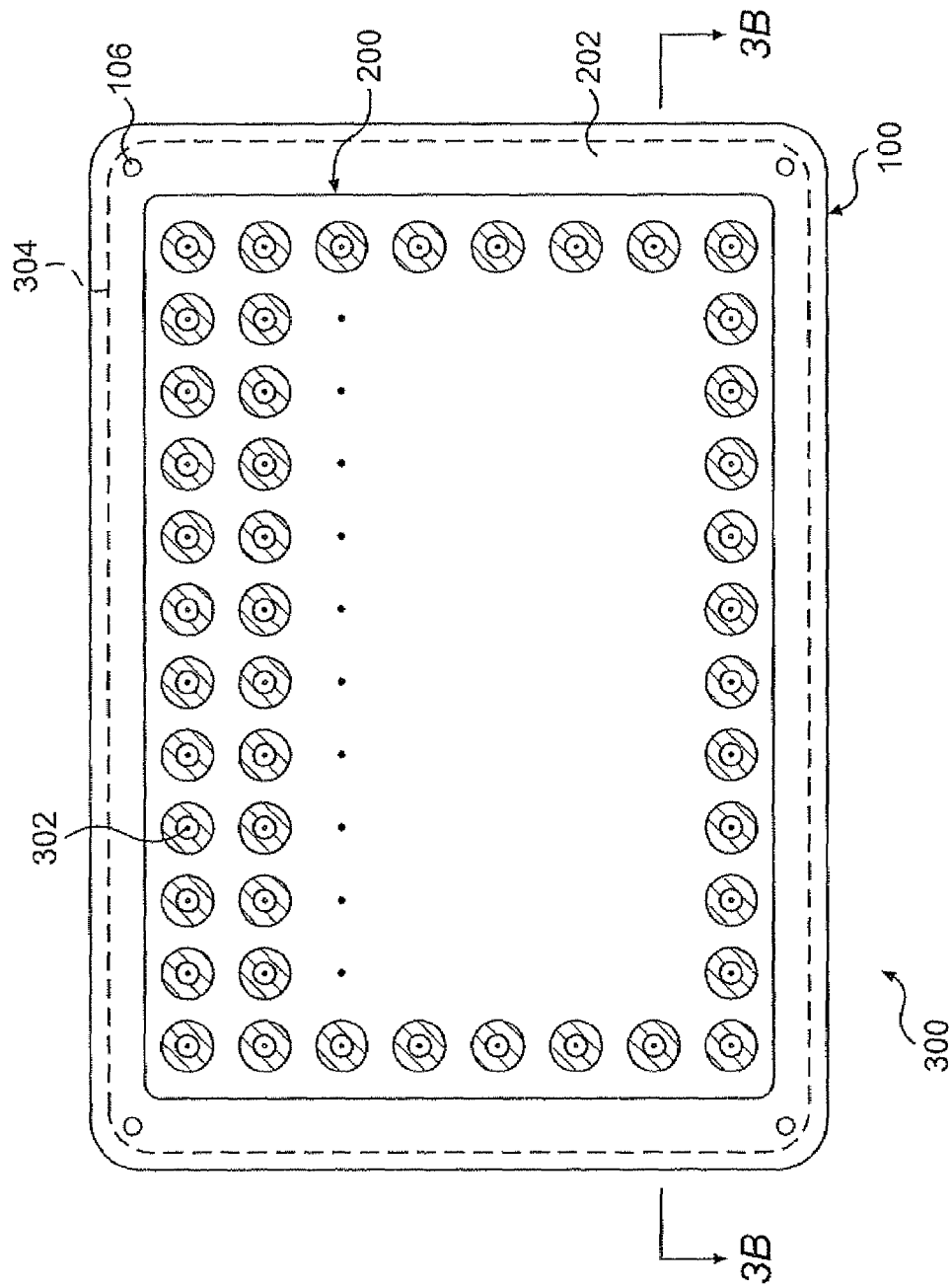
FIG. 3A is a schematic diagram of an exemplary crystallization apparatus, according to an embodiment of the present invention.

FIG. 3A illustrates an assembled multiple-site crystallization apparatus 300, according to an embodiment of the present invention. As shown, frame 202 of FIG. 2 is mounted on top of microplate 100 of FIG. 1A to provide multiple-site crystallization apparatus 300.

In this embodiment, apparatus 300 includes microplate 100 having ninety-six wells 302, a rim 304 around microplate 100, four reference pins 106, and an overlaying film 200 surrounded by a frame 202. Although not shown in FIG. 3A, apparatus 300 could also include a lid over frame 202, to protect the test sites and provide a surface on which to stack another microplate.

Figure 3B:
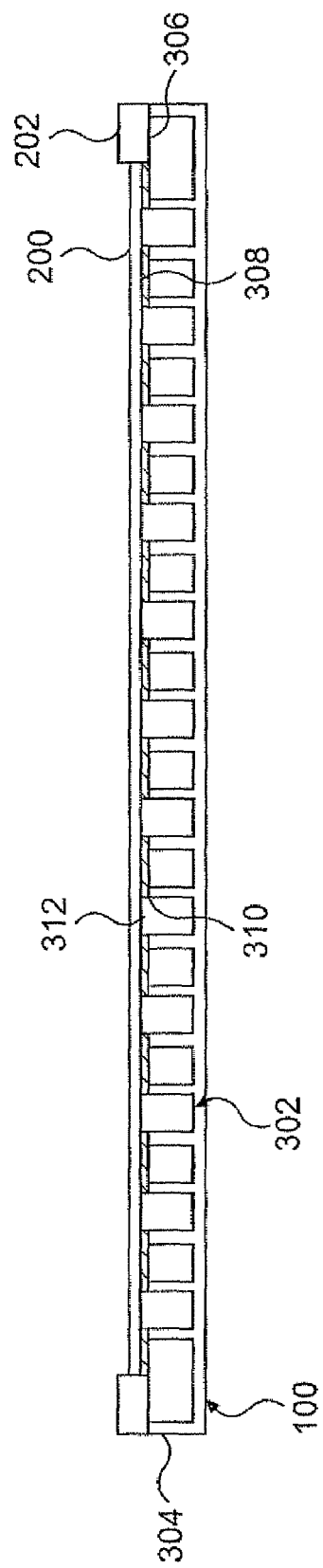
FIG. 3B is a schematic diagram showing a cross-sectional view of the crystallization apparatus shown in FIG. 3A along line 3B-3B.

FIG. 3B is a cross-sectional view of the embodiment of FIG. 3A taken along line 3B-3B, with frame 202 and film 200 on top of microplate 100. Optionally, frame 202 is secured to microplate 100 with a layer of pressure-sensitive adhesive 306. FIG. 3A shows how reference pins 106 align microplate 100 and framed film 200. Although FIGS. 3A and 3B show microplate 100 as having cylindrical wells, as one of ordinary skill in the art would appreciate, the wells could be any number of shapes, e.g., the wells could be oval or cubical with radiused corners.

In FIG. 3A, frame 202 with the attached film 200 is positioned over microplate 100 so that rim 304 of microplate 100 is under frame 202. Microplate 100 may be manufactured from any rigid material that is not biologically or chemically active with the screening solutions and is not water-soluble, e.g., glass, sapphire, acrylic, polystyrene, or polycarbonate. Microplate 100 has a plurality of wells 302 (in this example, ninety-six). The position and spacing of the wells is preferably a standard spacing, e.g., the standard spacing for 96-well microplates (e.g., 9 mm center to center), and the outside dimensions of frame 202 are preferably (although not necessarily) identical to the dimensions of standard microplates, so that automatic equipment can be used to handle frame 202 and microplate 100.

According to an embodiment of the method of the present invention, the exemplary crystallization apparatus shown in FIGS. 1A-3B is used as follows. First, the wells of microplate 100 are filled with an appropriate volume of crystal growing (screening) solution. Preferably, each well of microplate 100 is filled with a different crystal growing (screening) solution, to test the efficacies of the different crystal growing solutions with respect to a particular compound (e.g., a particular protein).

Film 200 is then placed upside down and precipitant solutions are pipetted onto the centers of positioning rings 204. Proper placement of the drops on film 200 can be accomplished with a hand-held pipette, an automatic variable-volume pipette, or an automatic pipetting machine. The Kushner patent, incorporated by reference above, contains several examples of crystal growth procedures.

Next, frame 202, with the attached film 200, is inverted and pressed onto the four corner reference pins 106 of microplate 100. With frame 202 pressed onto microplate 100, the ring 102 at each site preferably makes full contact with film 200. If, for some reason, a ring 102 does not fully contact film 200, then film 200 is gently pressed until the ring 102 makes complete contact. Although frame 202 keeps film 200 relatively flat, film 200 still possesses some "give" (e.g., some amount of elasticity, flexibility, or slack) that enables film 200 to move and better contact ring 102, to provide a good seal. If necessary for this seal, as described above, grease 104 can be disposed between film 200 and rings 202.

With frame 202 inverted and mounted on microplate 100, and with film 200 sealing the wells of microplate 100, the vapor diffusion process can begin. In this configuration, at each site, the precipitant solution (e.g., 50% protein solution and 50% screening solution of the associated site) is suspended from film 200 over the crystal growing solution (e.g., 100% screening solution) in the bottom of the wells of microplate 100. An air gap separates the two solutions. During vapor diffusion, vapor travels from the precipitant solution through the air gap to the crystal growing (screening) solution. This process of vapor diffusion concentrates the compound in the precipitant solution. In efficacious crystal growing solutions, the crystallization point is reached, and crystals begin to form.

A further embodiment of the present invention includes a lid that covers the microplate to protect grease from being rubbed off the rims before the frame is mounted on the microplate. FIGS. 4A, 4B, and 4C illustrate an exemplary lid 400, which covers the microplate 100 shown in FIGS. 1A-1C. Lid 400 has four reference openings 402 at its corners, which fit over the four corner reference pins 106 of microplate 100. Thus, a user can keep lid 400 over microplate 100 before using microplate 100, thereby protecting the test sites, the rings 102, the layer of grease 104, and any solution in the sites (see FIGS. 1B and 1C). Lid 400 also protects the test sites after solutions have been added and after frame 202 has been placed on microplate 100. Lid 400 can also provide a platform on which additional apparatus can be stacked, one on top of another, which is especially useful for automated robotic applications.

In a further embodiment of the present invention, film 200 is coated with a semi-hydrophobic material such that when a drop of precipitant solution is placed on film 200, the drop maintains its round shape, instead of leveling out and forming an elongated shape. The semi-hydrophobic material is not so hydrophobic that the drop would fall off if film 200 is inverted. Rather, the semi-hydrophobic material enables the drop to remain attached to film 200 when film 200 is inverted, and helps to keep the round shape of the drop. An example of a semi-hydrophobic material suitable for this purpose is a transparent polymer material, such as Rain-X™ Original Glass Treatment produced by Blue Coral-Slick 50, Ltd. of Cleveland, Ohio.

In a further embodiment of the present invention, a portion of film 200 is covered or partially covered (e.g., in a pattern such as a ring pattern) with a hydrophobic material to delimit areas in which to place and hold the precipitant solution. For example, referring to FIG. 2, the areas inside positioning rings 204 are partially covered with a hydrophobic material, leaving round spots in the center uncovered. The spots in the center are naturally hydrophilic, or are rendered so by coating them with a hydrophilic material. The diameter of the hydrophilic area is varied to produce ideal drop configuration for a given volume of precipitant solution. For example, a 1 mm spot holds a drop of between 0.5 and 1.0 microliters, while a 2 mm diameter spot holds a drop of between 4 and 6 microliters. This hydrophobic/hydrophilic configuration causes drops of precipitant solution to self-center and assume an ideal shape when placed on film 200, within positioning rings 204. Positioning rings 204 act as guides in placing drops at the individual sites, with the smaller hydrophilic areas within the rings precisely positioning the drops.

FIG. 3B illustrates an example of this embodiment. As shown, the bottom surface 308 of the film 200 is partially covered with a patterned hydrophobic coating 310. Hydrophobic coating 310 is patterned to create a number of uncoated test sites 312 corresponding to the location of wells 302 in microplate 100. When drops of precipitant solution are pipetted onto surface 308 (when film 200 is inverted) at the uncoated sites 312, the drops are prevented from moving outside the perimeter of the test sites and contacting each other, and are forced into an optimal shape.

In a further embodiment of the present invention, a portion of film 200 is covered or partially covered (e.g., patterned) with a layer of material that delimits areas in which to place and hold the precipitant solution. Furthermore, the layer of material acts as a physical barrier that contains the precipitant solution. For example, referring to FIG. 2, the area outside of positioning rings 204, or any desirable area, could be covered with a film or coating of measurable thickness. The area inside the positioning rings 204 could be hydrophilic or covered or partially covered or coated with a hydrophilic material or a material with a high affinity for the precipitant solution. It would be preferable if the area inside the positioning rings were transparent or coated or covered partially or entirely with a transparent material. This hydrophobic/hydrophilic or pseudo-well/hydrophilic/high affinity configuration causes drops of precipitant solution to self-center when placed on film 200, within positioning rings 204.

In a further embodiment of the present invention, after placing screening solutions and solutions with the compound to be crystallized at each site, assembling the components, incubating and (possibly) growing crystals, film 200 can be cut away at any site location. This cut-away portion of the film, with its attached sample, can then be removed for closer examination, while leaving the remaining samples undisturbed, Furthermore, after this examination, the film and sample can be placed back onto the site from which it was removed to continue with the crystal forming process.

In a further embodiment of the present invention, lid 400 and microplate 100 are made from materials that have good-to-excellent optical qualities, e.g., polystyrene, TPX, acrylic, and other plastics, and glass, sapphire, and quartz.

In a further embodiment of the present invention, one or multiple frames can be attached to a microplate or lower plate-like component, e.g., film bonded to frames that can be oriented in either the X or Y dimension of the plate in strips, to allow for partial or staggered use of the apparatus. In this multiple frame configuration with a strip layout, the frame could be made as an injection-molded piece with formed wells, with the film bonded to the frame at the bottom of the wells. Instead of using the above-described grease, the wells could be sealed to the lower plate using o-rings or something functionally equivalent.

In a further embodiment of the present invention, microplate 100 is replaced by another frame with film bonded to it, to create a plate-like component that holds solutions in a plurality of sites. The sites can be defined by, for example, hydrophobic material, hydrophobic ink, grease rings, or other chemical or physical structures that can be applied to the film. In this case, instead of grease 104 sealing a gap between film 200 and rims 102, grease 104, or some functional equivalent, would seal the gap between the two films.

In a further embodiment of the present invention, frame 202 does not have the hollow center that is shown, for example, in FIG. 2. Instead, frame 202 has interconnecting lattices with spaces between the lattices in any numerous combinations of patterns using interconnecting segments and open spaces. The test sites fall within the spaces. FIGS. 5A-5D illustrate an example of this embodiment of the present invention, with solutions held between a first film supported by a latticed bottom plate and a second film supported by a latticed top plate.

Figure 5A:
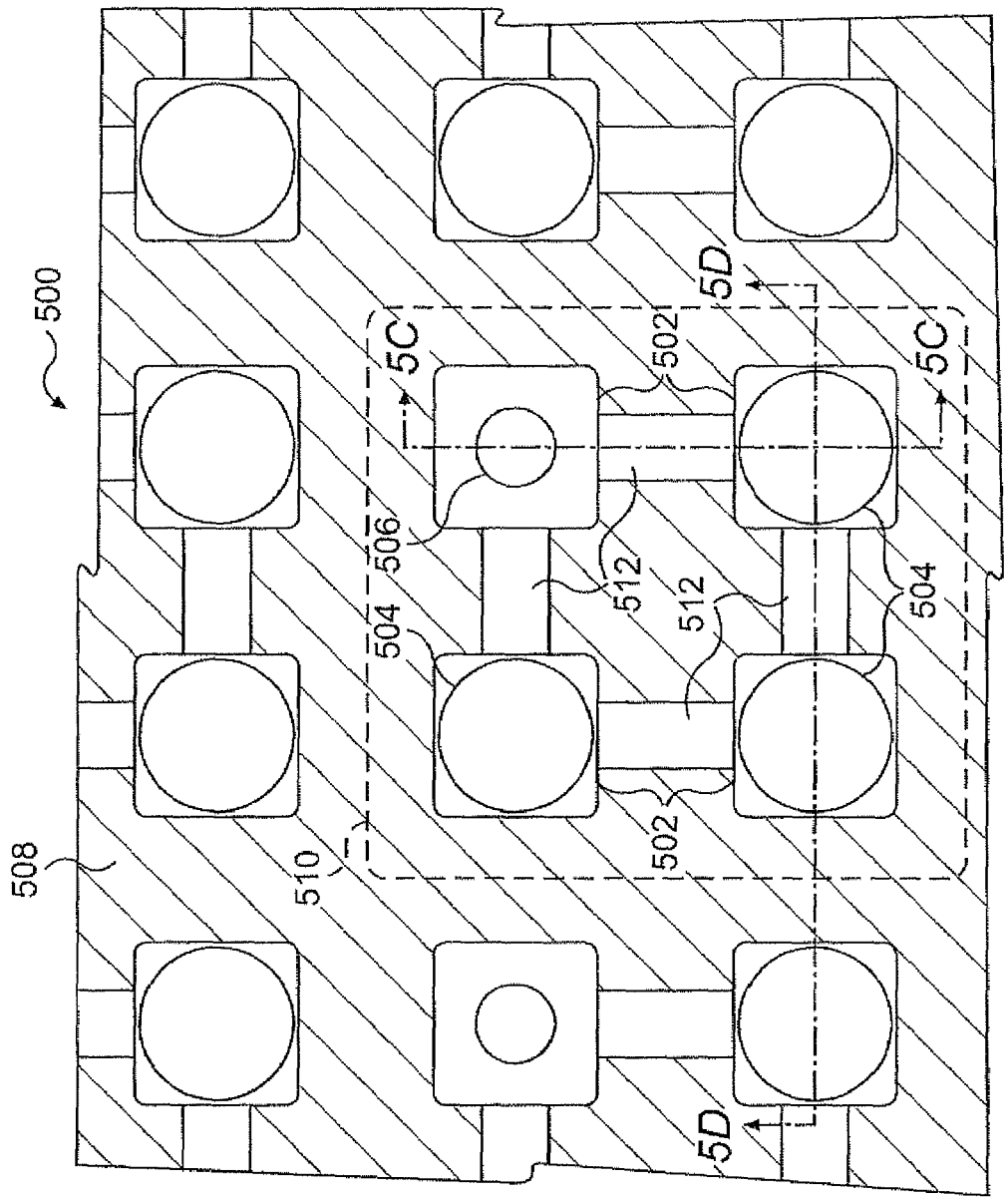
FIG. 5A is a schematic diagram of a top view of a portion of an exemplary crystallization apparatus having two films, according to an embodiment of the present invention.

FIG. 5A shows a top view of a portion of an apparatus 500 according to this embodiment of the present invention. This top view looks down through the transparent top film 528 that is supported from underneath by the top plate 526 and bonded to the top plate 526 with bonding agent 532 (see FIGS. 5C and 5D discussed below). Through-holes 502 are areas in which the bottom surface of the top film is not supported by the top plate, i.e., there is a hole in the top plate. A screening solution 504 (e.g., 100% screening solution) and a precipitant solution 506 (e.g., 50% screening solution and 50% protein solution) are disposed within through-holes 502. In area 508, the bottom surface of the top film is supported by and bonded to the top plate. Preferably, in area 508, the bottom surface of the top film is bonded to the top plate with an adhesive.

In this example, four through-holes 502 are used for a single crystallization site, as represented by the single site 510. Within this site 510, gas passages 512 (or air gaps) connect through-holes 502. Gas passages 512 can be created by, for example, etching the top plate in these areas and removing half of the thickness of the plate, or by molding depressions in the top side of the lattice that forms the top plate. Preferably, an adhesive seal between the top plate and the top film provides a seal for single site 510 that isolates four through-holes 502 from the remaining sites and through-holes of apparatus 500.

Figure 5B:
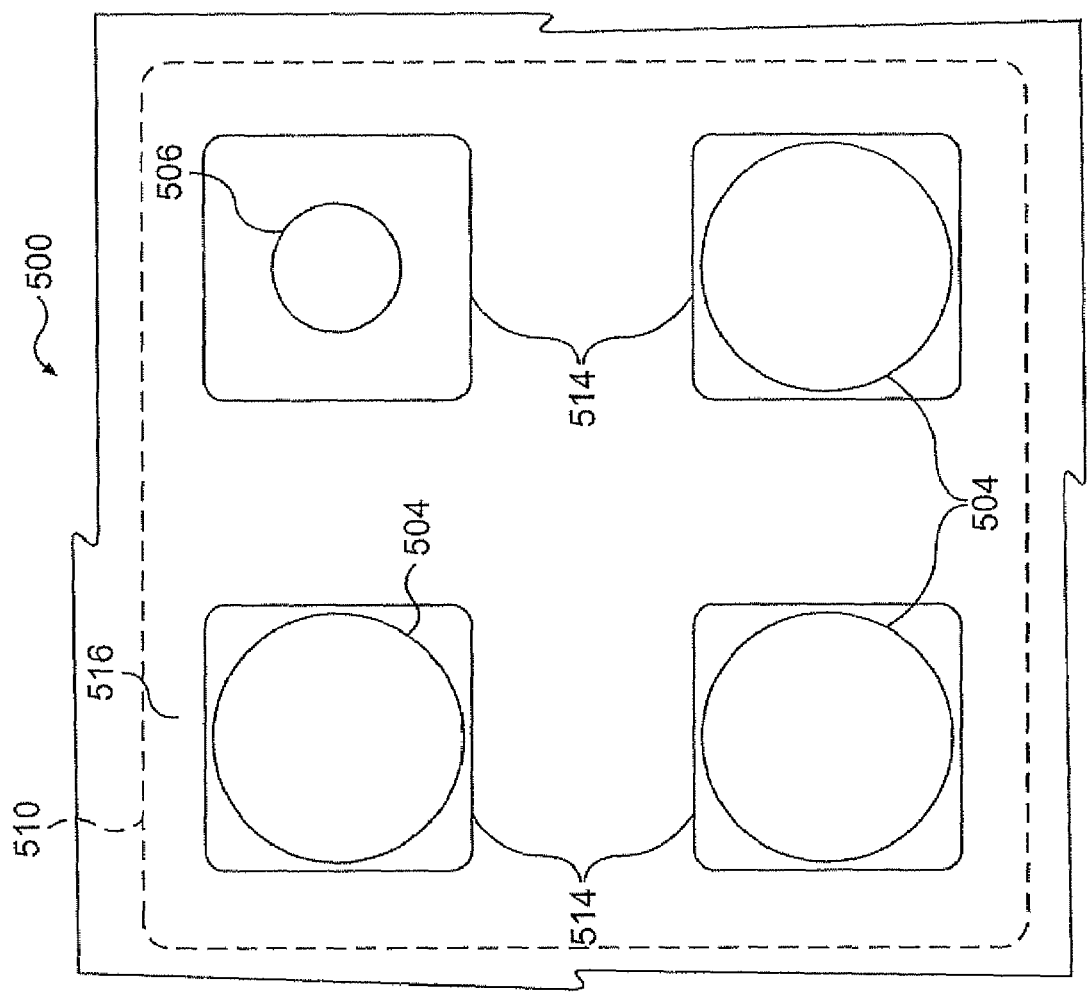
FIG. 5B is a schematic diagram of the crystallization apparatus of FIG. 5A, with the top plate and top film removed.

FIG. 5B illustrates apparatus 500 with the top plate and film removed, showing a view of the bottom film supported by the bottom plate, with screening solution 504 and precipitant solution 506 resting on top of the bottom film. Through-holes 514 in the bottom plate substantially align with through-holes 502 of the top plate. Through-holes 514 are areas in which the bottom surface of the bottom film is not supported by the bottom plate, i.e., there is a hole in the bottom plate. At each site, screening solution 504 and precipitant solution 506 are disposed over through-holes 514, and are preferably held in place using a hydrophobic mask. In area 516, the bottom surface of the bottom film is supported by the bottom plate. Preferably, in area 516, the bottom surface of the bottom film is partially or fully bonded to the bottom plate with an adhesive.

Figure 5D:
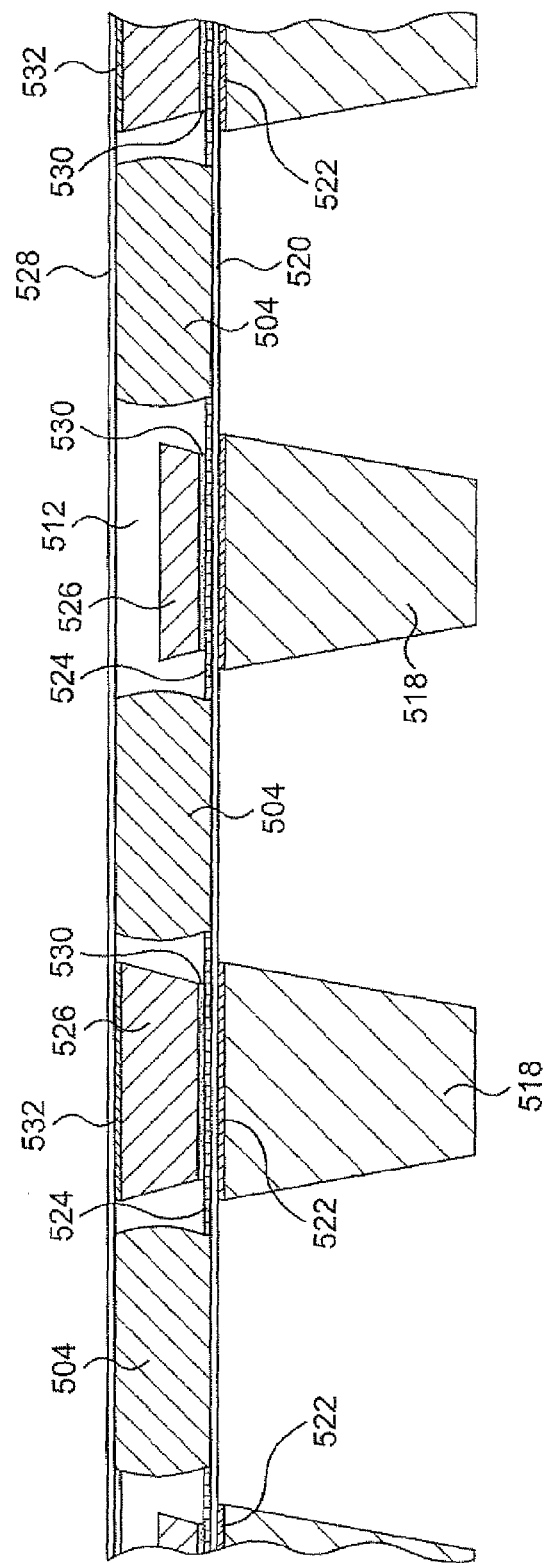
FIG. 5D is a schematic diagram of a cross-sectional view of the crystallization apparatus of FIG. 5A along line 5D-5D.

FIGS. 5C and 5D illustrate cross-sectional views of apparatus 500 along line 5C-5C and line 5D-5D (identified in FIG. 5A), respectively. As shown, bottom plate 518 is bonded to bottom film 520 with an adhesive 522. Screening solution 504 and precipitant solution 506 are disposed on bottom film 520 in the area of through-holes 502 and 514. Preferably, a hydrophobic mask 524 is applied to bottom film 520 to hold solutions 504 and 506 in place.

Top plate 526 is disposed on top of bottom film 520. In a preferred embodiment, top plate 526 is bonded to bottom film 520 with a pressure sensitive adhesive or grease 530. Top plate 526 supports top film 528, which is located on the side of top plate 526 opposite bottom film 520. Top film 528 is preferably bonded to top plate 526 with an adhesive 532.

When top plate 526 and its top film 528 are placed on top of bottom film 520, solutions 504 and 506 are disposed within through-holes 502 of top plate 526 and are sandwiched between and in contact with the bottom surface of top film 528 and the top surface of bottom film 520. As shown in FIGS. 5C and 5D, in this configuration, gas passages 512 are created between adjacent through-holes 502 of site 510. Vapor diffusion through these passages 512 and around solutions 504 and 506 promotes the concentration of the target compound in solution 506 and, if successful, the crystallization of that compound.

An exemplary implementation of the embodiment of FIGS. 5A-5D uses a 384-site plate for top plate 526 and bottom plate 518. In this example, as shown in FIG. 5C, the width 540 of screening solution 504 is approximately 1.0 mm and the width 542 of precipitant solution 506 is approximately 0.500 mm. The distance 544 between the bottom top film 528 and the top of bottom film 520 is approximately 0.375 mm. As an example, this configuration creates spaces for samples of about 100 nl of precipitant solution 506 and 400 nl of screening solution 504.

Although FIGS. 5A-5D illustrate a single crystallization site having four sub-sites (i.e., through-holes in which the solutions are disposed), one of ordinary skill in the art would appreciate that a site could include two or more through-holes.

According to an embodiment of the present invention, the exemplary crystallization apparatus shown in FIGS. 5A-5D is used as follows. First, screening solution 504 is deposited on bottom film 520 within the boundaries of the hydrophobic mask 524. In this example, for site 510, three samples of the same screening solution 504 are deposited on bottom film 520 in locations corresponding to three of the four through-holes 514 of the bottom plate 518 within the single site 510. Next, the precipitant solution 506 is deposited on bottom film 520 within the boundaries of the hydrophobic mask 524. In this example, for site 510, one sample of precipitant solution 506 is deposited on bottom film 520 in a location corresponding to the fourth through-hole 514 of the bottom plate 518 within the single site 510.

With the screening and precipitant samples in place, top plate 526 and top film 528 are placed over bottom film 520 and bottom plate 518 such that through-holes 514 of bottom plate 518 and through-holes 502 of top plate 526 are aligned. Preferably, reference pins in bottom plate 518 and corresponding reference holes in top plate 526 facilitate this alignment. Alternatively, bottom plate 518 is held and positioned in a carrier plate (not shown) and top plate 526 is positioned exactly over bottom plate 518 by that carrier plate when it is placed on top of bottom film 520 and bottom plate 518. Placing top plate 526 on bottom film 520 seals site 510 within bottom film 520, top plate 526, and top film 528. In a preferred embodiment, a sealant is used between bottom film 520 and top plate 526 to help facilitate this seal. The sealant could be, for example, a pressure sensitive adhesive, a malleable sealant with adhesive properties, a gasket with adhesive properties, grease, oil, a gasket, other sealants, or combinations of such sealants.

With top plate 526 and top film placed over bottom film 520, the samples of screening solution 504 and precipitant solution 506 are sandwiched between bottom film 520 and top film 526. The vapor diffusion process then begins. In this configuration, air gaps provided by gas passages 512 separate the screening solution samples from the precipitant solution samples at each site. Vapor diffusion from precipitant solution 506 to screening solutions 504 concentrates precipitant solution 506, potentially creating a crystal forming condition.

In an alternative embodiment of the method for forming crystals associated with FIGS. 5A-5D, the samples of screening solution and precipitant solution are first deposited on the bottom surface of top film 528, instead of on the top surface of bottom film 520. Top plate 526 and top film 528 would be inverted for this first step. In addition, the bottom surface of top film 528 preferably would have a hydrophobic mask to contain and position the samples. After depositing the samples on the bottom surface of top film 526, the top plate 526 and top film 528 are inverted and placed over bottom film 520. The samples are thereby sealed between bottom film 520, top plate 526, and top film 528, and the vapor diffusion process begins.

Figure 6:
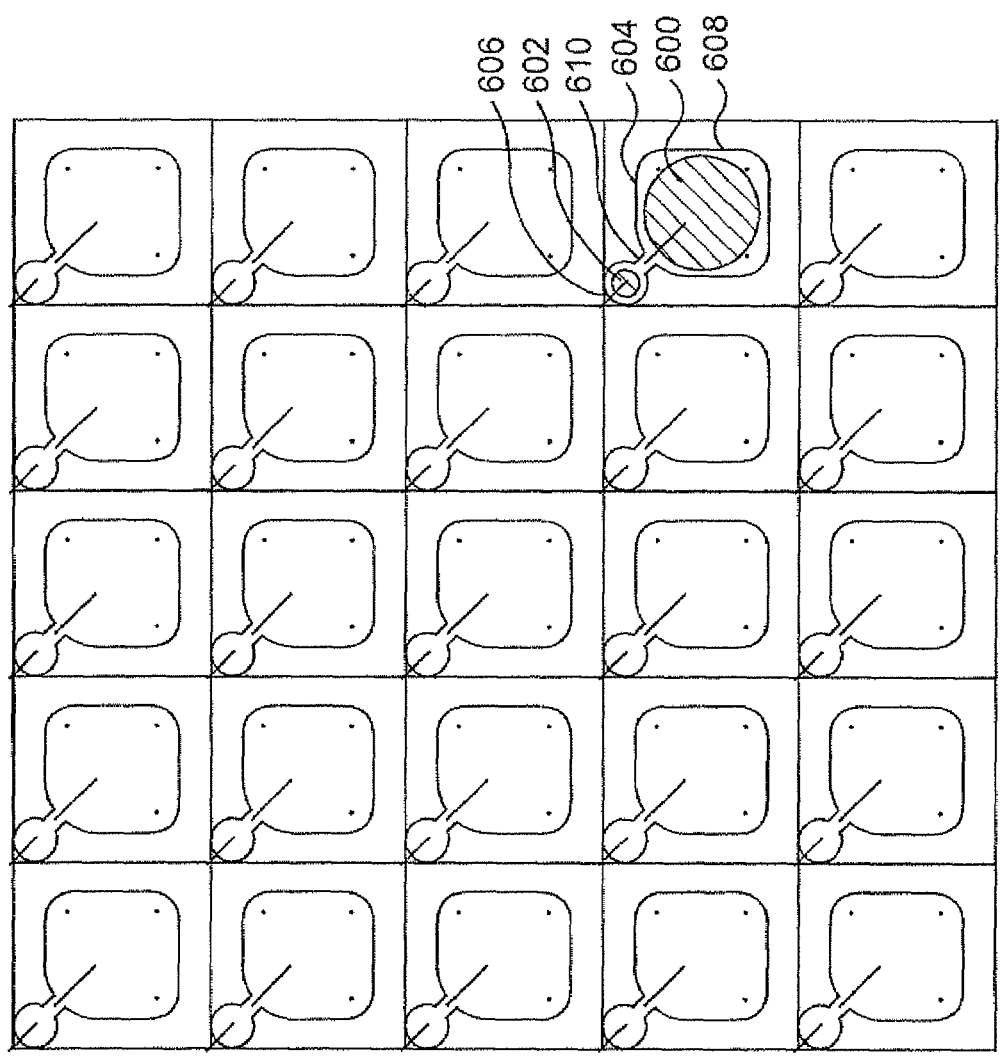
FIG. 6 is a schematic diagram of a top view of a portion of another exemplary crystallization apparatus having two films, according to an embodiment of the present invention.

FIG. 6 illustrates another embodiment of the present invention using a first film supported by a latticed bottom plate and a second film supported by a latticed top plate. As shown, this embodiment disposes a screening solution 600 and a precipitant solution 602 within a single through-hole 604 of a top plate. Preferably, a hydrophobic mask on the top surface of the bottom film holds solutions 600 and 602 in place within the through-hole 604. Through-hole 604 includes a first chamber 606 and a second chamber 608 connected by a gas passage 610. In this manner, vapor solution can flow from precipitant solution 602 through gas passage 610 and to screening solution 600, to promote crystal growth within the first chamber 606. Also, preferably, through-hole 604 is isolated from its surrounding through-holes by an adhesive seal around through-hole 604. The apparatus of FIG. 6 is used in a manner similar to the methods described above in reference to FIGS. 5A-5D.

Returning to FIG. 2, in another embodiment of the present invention, frame 202 has a component design that enables different films to be applied to different sites. For example, rather than being a single piece, frame 202 could include an outside frame into which one or more inner frames are inserted. The outside frame could have a portion of its opening covered with film, or could have no film at all. Each inner frame could have a different type of film, and could be interchangeably placed within the outer frame. In this manner, a researcher can use various configurations of the inner frames to cover different test sites of a single apparatus with different films.

In a further embodiment of the present invention, the components of the apparatus are configured to accommodate sitting drop and sandwich drop formats. For example, when top plate 526 of FIGS. 5A-5D is made thicker, the apparatus becomes a sitting drop configuration, or alternatively, if the sample volume of the precipitant solution 506 is reduced so that it does not contact the bottom of top film 528 of top plate 526, the apparatus provides a sitting drop configuration.

Figure 7:
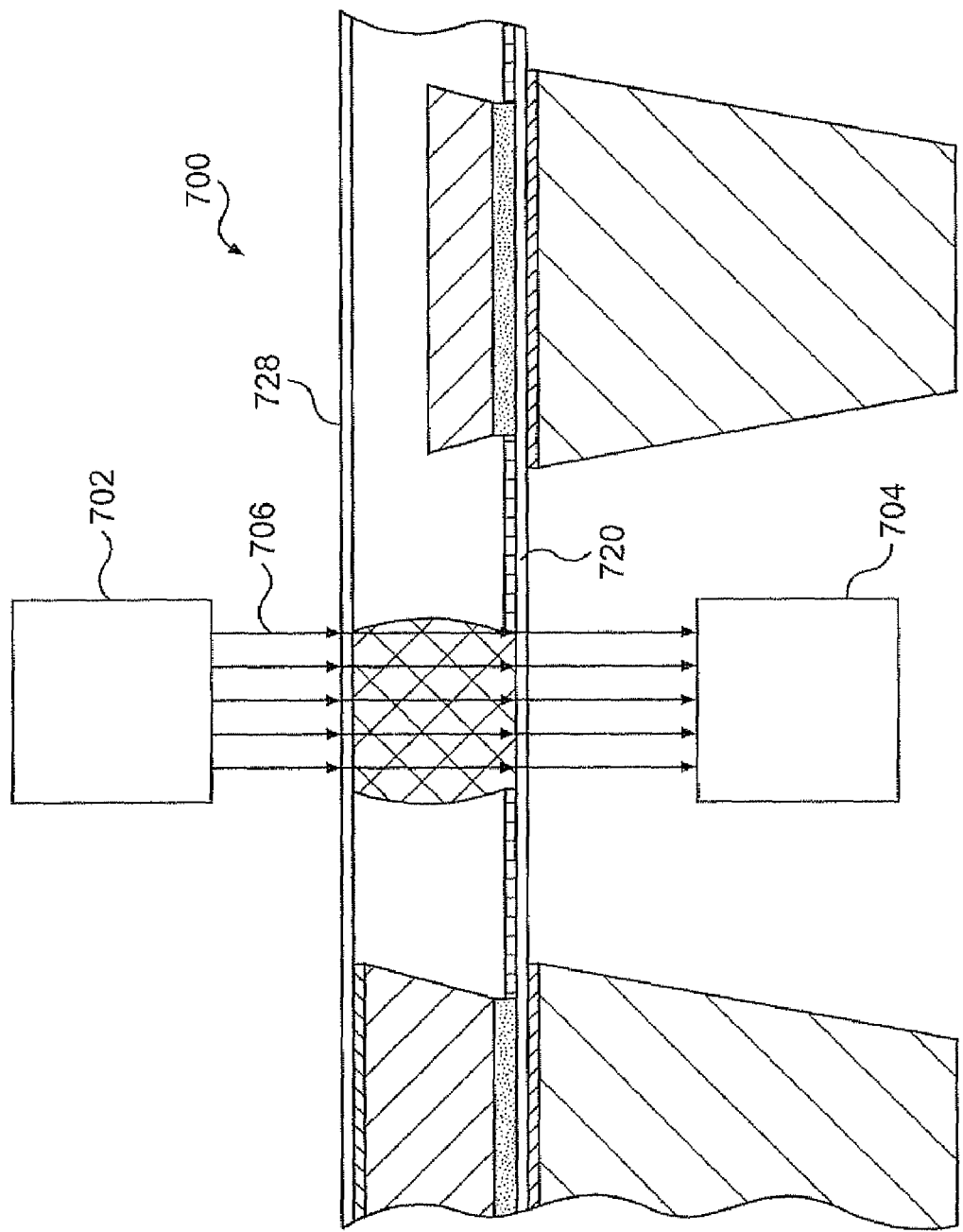
FIG. 7 is a schematic diagram illustrating the detection of crystals in an exemplary crystallization apparatus having two films, according to an embodiment of the present invention.

In a preferred embodiment, however, the embodiments of FIGS. 5A-5D and 6 use a sandwich drop format because it enables the detection of the presence of target compound crystals optically or with other electromagnetic radiation (e.g., x-rays), with minimal distortion. FIG. 7 illustrates an example of this detection method, with an emitter 702 (e.g., an electromagnetic radiation emitter) on one side of an apparatus 700 and a detector 704 (e.g., electromagnetic radiation detector) on the opposite side. Detection system sensitivity is optimized by flat transparent thin films 720 and 728 that hold the sample in a sandwich configuration, with the films 720 and 728 parallel and with the detection beams 706 normal to the films 720 and 728. The films are preferably transparent to the beams typically used in crystal detection systems, such as electromagnetic radiation. The embodiments of FIGS. 5A-5D, 6, and 7 attempt to optimize the automated detection of crystals at the earliest time by enabling the assembled plates to be repeatedly scanned by a detection system without interrupting the vapor diffusion/crystal growth process.

A further embodiment of the present invention accelerates and controls the crystal growth process by pumping volatile vapor (e.g., water or alcohol) away from a crystallization site. This approach can be applied to the embodiments described above that have separate precipitant and screening solutions (e.g., the separate drops 600 and 602 shown in FIG. 6). In such case, pumping out the volatile vapor accelerates, facilitates, and controls the concentration of the precipitant solution. Instead of separate precipitant and screening solutions, however, a preferred embodiment mixes a protein solution and a screening solution in the same location to form a precipitant solution, and pumps volatile vapor away from that precipitant solution to promote and control crystal growth within the precipitant solution.

Controlled removal of volatile vapor from a crystallization site accelerates the rate at which the volatiles remaining in solution within the site evaporate into the gas environment of the test site. In the case of separate screening and precipitant solutions, both the screening solution and the precipitant solution evaporate more rapidly. The concentration of protein in the precipitant solution therefore increases more rapidly, due to both vapor diffusion to the screening solution and vapor removed by pumping. In the case of a single volume of protein solution and screening solution combined into a precipitant solution, the precipitant solution evaporates more rapidly when pumped, thereby accelerating the increase in concentration of protein in the precipitant solution.

According to this embodiment of the present invention, volatile vapor is pumped away from a crystallization site at least once during the crystallization process. Preferably, however, a crystallization site is subjected to several cycles of pumping that provide a desired evaporation rate and rate of increase in protein concentration. In each cycle, volatile vapor is pumped out and replaced with ambient air or gas that is generally of a lower level of volatiles (e.g., in the case of water vapor, the ambient air is of a lower humidity) than the gas environment within the site had been before the pumping. When the gas environment in the site is replaced with ambient gas having a lower volatile content, increased volatile evaporation of the precipitant solution occurs, thereby increasing the precipitant solution's concentration. After a period of incubation in which more volatiles evaporate into the gas environment of the crystallization site, the next pumping cycle commences, to remove the newly accumulated volatile vapor. To facilitate crystallization, the period of incubation can include holding the temperature low and the pumping cycles can use very desiccated gas of low volatile content. In addition, the crystallization site can be held under low pressure (partial vacuum), e.g., in between pumping cycles, to further accelerate the evaporation rate and rate of increase in protein concentration.

In controlling temperature to facilitate crystallization, as an example, the incubation temperature can be lowered, which in some cases enables the initiation of crystal formation, while the concentration of the precipitant solution increases due to the pumping. Without pumping, the lower temperature could slow concentration of the precipitant solution to an unacceptably low rate. Crystallization screening is usually done at either 4° C. or 20° C., but with pumping can be done at lower temperatures as long as freezing does not occur.

In controlling the volatile content during pumping cycles, in an embodiment of the present invention, ambient air is conditioned by a desiccant air dryer. In another embodiment of the invention, a desiccant is added to the crystallization site or to the surroundings outside the crystallization site (from which the ambient air or gas is drawn).

To provide the pumping feature of this embodiment of the present invention, an exemplary crystallization site is sealed except for a vent on the sealed site. In one embodiment, the vent is a passive vent that is open (i.e., not normally closed), but that inhibits vapor diffusion out of the site. In one example, a passive vent is a passage that provides communication between the crystallization site and the surroundings outside the site (e.g., the ambient air or gas). This passage has a length, volume, shape, and/or configuration that sufficiently inhibits vapor diffusion out of the site.

As an example, to form the passage, at least one wall of the crystallization site is made of film and the passive vent is disposed in the film. This passive vent could be formed in the film by, for example, laser ablation. This laser-ablated passage would not be normally closed, but would be either small enough or long enough to sufficiently inhibit vapor diffusion out of the site. In an alternative embodiment, the passive vent could be provided by a vapor permeable material.

In another embodiment, the vent is an active vent that is normally closed, but that opens to allow passage of volatile vapor out and ambient air or gas in the site. In one example, the active vent is a valve that is normally closed when no pressure differential exists between the pressure inside the crystallization site and the pressure outside the crystallization site. When a pressure differential is applied, however, the valve opens and allows the passage of air, gas, and volatile vapor. Thus, for example, if the pressure outside of the crystallization site is reduced, the higher pressure inside the site forces the valve open, allowing volatile vapor to escape from the site. The pressure inside the site then equalizes with the vacuum pressure outside of the site. Then, when the vacuum outside the site is removed, and the outside pressure is raised (e.g., to standard atmospheric pressure or above), fresh ambient air or gas enters the site and the valve closes.

In one implementation, at least one wall of the crystallization site is made of film and the valve is disposed in the film. The valve is normally closed when no pressure differential exists across the film. To provide this function, the valve can be a slit cut into the film by, for example, piercing the film with a sharp wedge-shaped tip. The width of the wedge-shaped tip is preferably equal to the desired length of the valve vent. As one of ordinary skill in the art would appreciate, other methods for forming the valve in the film could be used. In addition, in an alternative embodiment, the valve is a mechanical structure such as a flap valve.

The film in which a vent is formed is preferably compliant, as well as compatible with the method used to detect crystal growth. In being compliant, the film preferably flexes or bends and has memory that enables it to deform and return to its original shape. In this manner, for example, the film can be cut, with the material around the cut separating as the cut is made and then rejoining after the cut is made to provide a normally closed active vent, To enable crystal growth detection, the film is preferably transparent to the detection medium used, for example, allowing the passage of electromagnetic waves such as light or x-rays. In an embodiment of the invention, the film is made of approximately 0.001-0.003 inch thick transparent Teflon™.

Figure 8A:
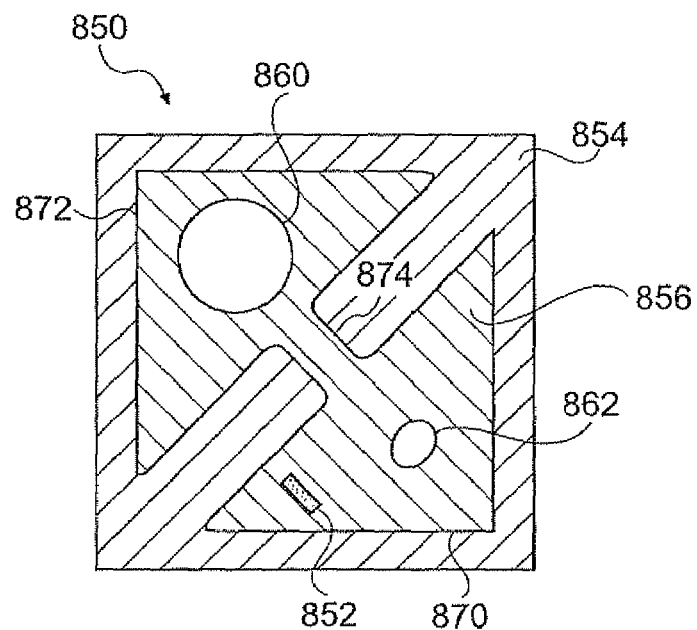
FIG. 8A is a schematic diagram of an exemplary crystallization site that has a separate precipitant solution and screening solution and is adapted to pump out volatile vapor, according to an embodiment of the present invention.

FIG. 8A illustrates an exemplary crystallization site 850 that separates a precipitant solution 862 from a screening solution 860 and is adapted to pump out volatile vapor.

As shown, crystallization site 850 includes a structure 854 that defines the sidewalls of the site. Structure 854 could be, for example, a lattice plate having through-holes, each of which define a site. This lattice plate could be made of, for example, metal, hard plastic, or ceramic. Stainless steel is preferred because of its susceptibility to photochemical etching. Preferably, structure 854 is relatively stiff and dimensionally stable. Alternatively, structure 854 could be a layer of pressure sensitive adhesive that has been punched, formed, die-cut, or printed to form a plurality of crystallization sites. This punched, formed, die-cut, or printed pressure sensitive adhesive (being of suitable thickness) would define the sidewalls of the sites and also provide a surface to which upper and lower films (described below) can adhere.

In FIG. 8A, a lower film is attached to the bottom side of structure 854. Optionally, the lower film has a hydrophobic mask 856 that helps hold solutions 860 and 862 in place. An upper film is attached to the top side of structure 854. Together, structure 854 and the upper and lower films seal the crystallization site 850. Structure 854 defines a first chamber 870 and a second chamber 872 connected by a gas passage 874. In this manner, vapor from precipitant solution 862 can flow from first chamber 870, through gas passage 874, into second chamber 872, and to screening solution 860, to promote crystal growth within precipitant solution 862.

The upper or lower film of the crystallization site 850 contains an active vent 852 that is normally closed when the pressure inside site 850 is equal to the ambient pressure. When a pressure differential is applied across the film, vent 852 opens to allow passage of volatile vapor out and ambient air or gas in. Reducing the outside pressure below that of the inside causes vent 852 to open to allow volatile vapor to escape. Increasing the outside pressure above that of the inside causes the vent 852 to open to allow ambient air or gas to enter site 850. Although vent 852 is shown aligned with chamber 870, vent 852 could be disposed anywhere in communication with the interior of site 850 (e.g., over chamber 872 or passage 874), except in contact with the liquids in chambers 870 and 872.

An embodiment of the present invention provides a method for forming crystals using the exemplary structure of FIG. 8A. According to this method, the samples of screening solution 860 and precipitant solution 862 are first deposited on the lower film. Structure 854 and the upper film are then placed over the solutions 860 and 862 to seal them within the site 850. The differences in concentration between solutions 862 and 860 cause vapor diffusion from the precipitant solution 862 to the screening solution 860. The gas environment within site 850 therefore contains volatile vapor evaporated off of the precipitant solution 862. As this vapor diffusion occurs, the method continues by reducing the pressure outside the site 850 to below the pressure inside the site 850. This pressure differential causes vent 852 to open, thereby allowing volatile vapor to escape. The pressures inside and outside of site 850 are then allowed to equalize. As pressure equilibrium is reached, vent 852 closes.

The pressure outside site 850 is then increased above the reduced pressure inside the site, e.g., the outside pressure is allowed to return to ambient pressure, which causes vent 852 to open to allow outside air or gas to enter site 850. The pressures inside and outside of site 850 are then allowed to equalize again. As pressure equilibrium is reached, vent 852 closes and seals the site 850. With the gas environment inside of site 850 replaced with ambient air or gas, the vapor diffusion continues in a period of incubation until the next pumping cycle.

The magnitude or depth of vacuum, its duration, and the frequency and the number of pumping cycles can be varied to control the rate of concentration of the precipitant solution 862 and thereby control the initiation of crystallization, and, subsequently, the rate at which crystallization continues. For example, higher vacuums and longer durations of vacuum can provide a more complete exchange of volatile vapor for ambient air or gas. Higher frequencies and numbers of pumping cycles can provide more exchanges of volatile vapor and ambient air or gas.

Figure 8B:
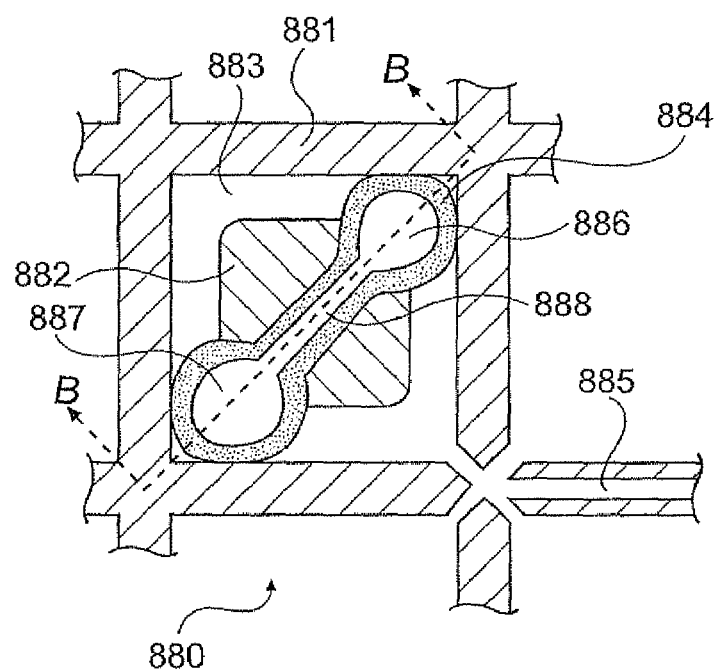
FIG. 8B is a schematic diagram of exemplary crystallization site that separates a precipitant solution from a screening solution, and is adapted to pump out volatile vapor and mix the separate precipitant solution and screening solution, according to an embodiment of the present invention.
Figure 8C:
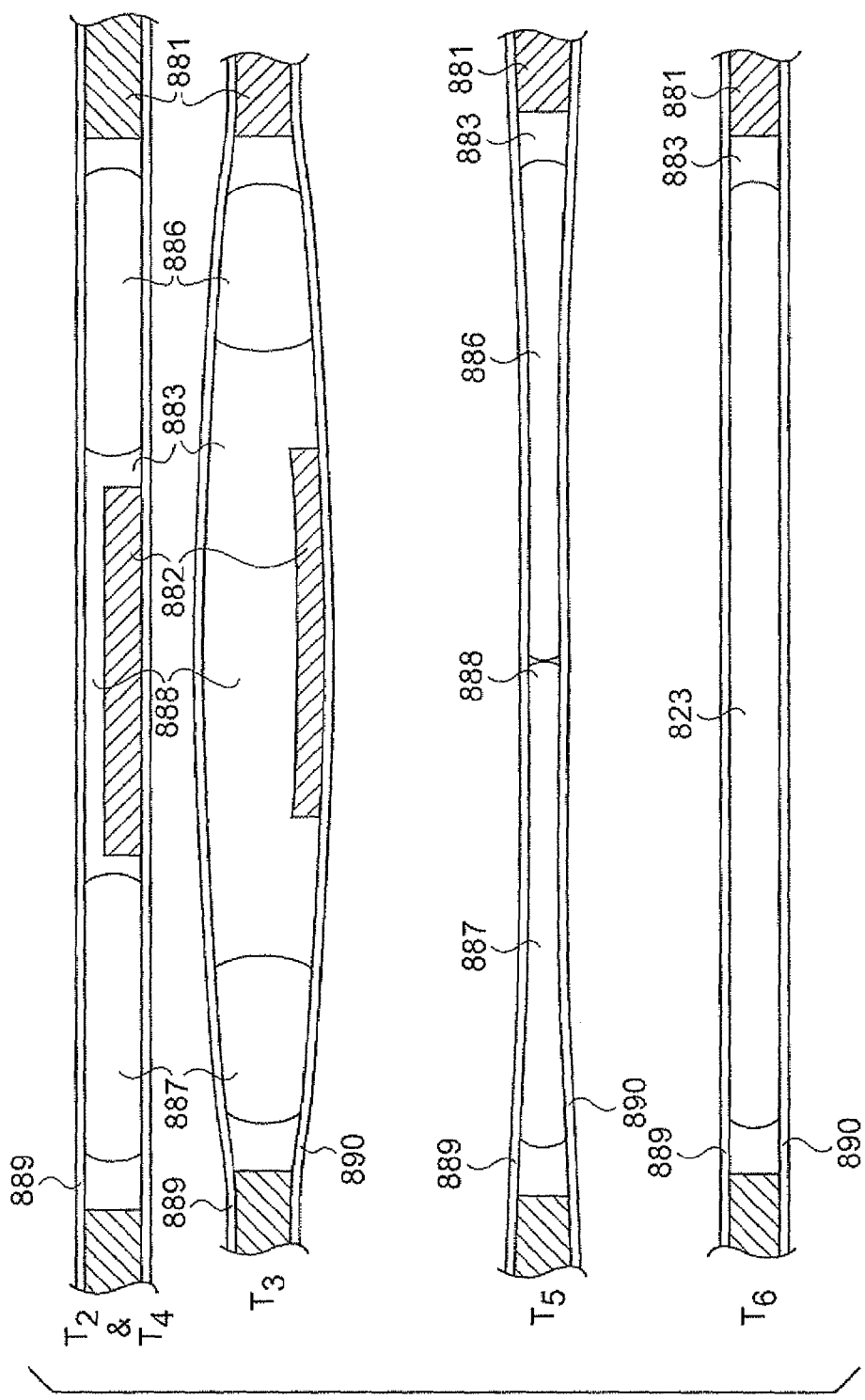
FIG. 8C is a schematic diagram showing cross-sectional views of the crystallization site of FIG. 8B along line B-B at different steps of an exemplary method for forming crystals using the site of FIG. 8B, according to an embodiment of the present invention.

FIGS. 8B and 8C illustrate another exemplary crystallization site 880 that separates a precipitant solution 887 from a screening solution 886 and is adapted to pump out volatile vapor. Crystallization site 880 is further adapted to mix the separate precipitant solution 887 and screening solution 886 if desired. Crystallization site 880 is preferably one site of a multi-site apparatus.

As shown, crystallization site 880 includes a structure 881 that defines the sidewalls of the site. Preferably, structure 881 is a layer of pressure sensitive adhesive or a film with surfaces of pressure sensitive adhesive that has been punched, formed, die-cut, or printed to form a plurality of crystallization sites.

Structure 881, by its thickness, defines the sidewalls of site 880 and provides a surface to which an upper film 889 and lower film 890 can adhere (as shown in the cross-sections of FIG. 8C).

Within the site 880 defined by structure 881, a hydrophobic mask 884 is disposed on the lower film 890, which defines the areas in which precipitant solution 887 and screening solution 886 are held. Hydrophobic mask 884 also defines a channel 888 through which solutions 886 and 887 can diffuse and/or mix. Optionally, as shown in FIG. 8B, site 880 can also include an internal site structure 882 that further defines channel 888. Structure 882 is preferably a pressure sensitive adhesive that is adhered to lower film 890 and is approximately half the thickness of the site-defining structure 881.

In addition to defining site 880, structure 881 defines the remaining sites of the multi-site apparatus, as well as the vents connected to the sites. In the example of FIG. 8B, structure 881 defines a vent 885 that is in communication with four adjacent sites, one of which is site 880. Vent 885 can be active or passive. In one embodiment, the layout of the multiple sites and the vents to each site is such that the volume of each vent is roughly equal. Together, upper film 889, structure 881, and lower film 890 seal the crystallization site 888, except for vent 885.

An embodiment of the present invention provides a method for forming crystals using the exemplary structure of FIG. 8B. FIG. 8C illustrates cross-sectional views of the structure along line B-B at different steps of the method. According to the exemplary method, at time $T_1$, samples of screening solution 886 and precipitant solution 887 are first deposited on lower film 890 within the structure 881 and within the hydrophobic mask 884. Upper film 889 is then placed over the solutions 886 and 887 to seal them within the site 881. At this point, the configuration of site 880 is as shown at time $T_2$ of FIG. 8C.

The differences in concentration between solutions 886 and 887 cause vapor diffusion from the precipitant solution 887 to the screening solution 886 through channel 888. The gas environment within site 881 therefore contains volatile vapor evaporated off of the precipitant solution 887.

As this vapor diffusion occurs, the method continues by reducing the pressure outside the site 880 to below the pressure inside the site 880. This initial application of a vacuum causes upper film 889 and lower film 890 to bulge outward as shown at time $T_3$ in FIG. 8C As shown, the position and shape of solutions 886 and 887 change and the volume of channel 888 increases. The higher pressure inside site 880 then pushes out the accumulated volatile vapor through vent 885, which is either active or passive.

As pressure equilibrium is reached between the inside and outside pressures, the bulges of films 889 and 890 subside and vent 885 closes if it is an active vent. At this time $T_4$, the configuration of site 880 is roughly the same as it was at time $T_2$, as shown in FIG. 8C.

At time $T_5$, the vacuum is released, which increases the pressure outside site 880 to above the reduced pressure inside the site. This differential pressure causes upper film 889 and lower film 890 to bulge inward as shown for time $T_5$ in FIG. 8C. The position and shape of solutions 886 and 887 change, the volume of channel 888 decreases, and the solutions 886 and 887 contact each other. The higher pressure outside site 880 then pushes outside air or gas into site 880 through vent 885. The pressures inside and outside of site 880 are then allowed to equalize again. As pressure equilibrium is reached, site 880 returns to the condition shown at time $T_6$, which is similar to times $T_2$ and $T_4$ except that solutions 886 and 887 are joined as one volume of solution 823. With the gas environment inside of site 880 replaced with ambient air or gas, the vapor diffusion continues in a period of incubation until the next pumping cycle.

In one aspect of this embodiment, the differential pressures applied across films 889 and 890 are sufficient enough to cause movements of films 889 and 890 that squeeze solutions 886 and 887 such that they contact each other in channel 888. This condition would occur, for example, as shown at time $T_5$ in FIG. 8C. After precipitant solution 887 and screening solution 886 contact each other, they would begin to diffuse into each other. Further pumping and movement of films 889 and 890 could be used to control the rate of this diffusion. For example, rapidly applying high vacuums for short durations promotes rapid mixing. Thus, the sandwich configuration provided by compliant films 889 and 890 in combination with the pumping enable control over mixing and diffusion of a precipitant and screening solution or a combination of both. After the solutions are adequately mixed, further pumping enables control over the concentration of the mixed solutions. A researcher can therefore use this embodiment of the present invention to obtain results quickly and in a controlled manner. Combining this embodiment with high resolution optical and light scattering detection systems having automatic feedback to control the pumping parameters (e.g., depth and duration of vacuum, rate of change of pressure, and cycle frequency) and other parameters such as temperature, constitutes a powerful high throughput screening system for rapid detection of successful screening solutions as well as for growth of high quality crystals.

Figure 8D:
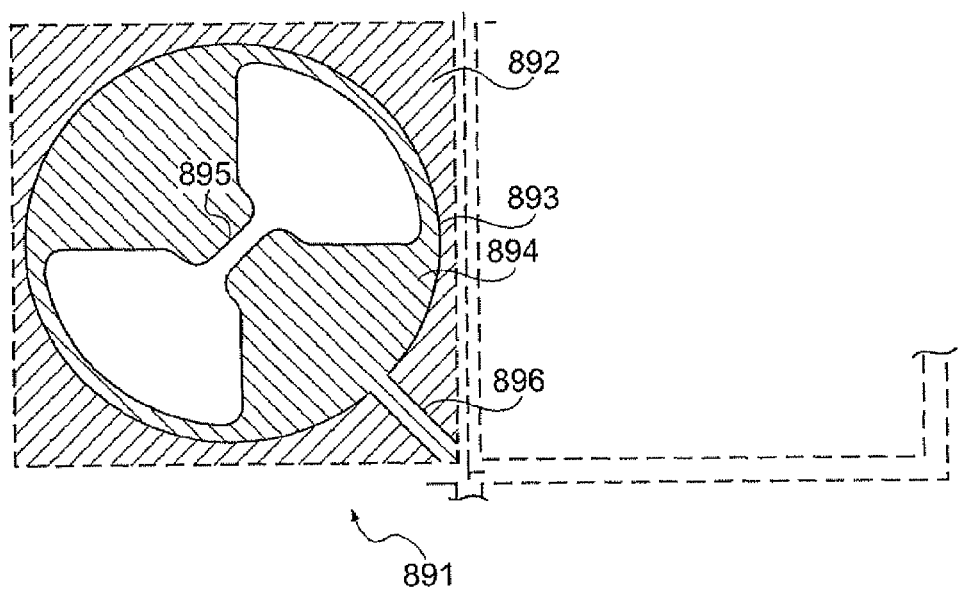
FIG. 8D is a schematic diagram of a crystallization site that separates a precipitant solution from a screening solution, is adapted to pump out volatile vapor and mix the separate precipitant solution and screening solution, and is conveniently susceptible to manufacture, according to an embodiment of the present invention.

FIG. 8D illustrates an alternative embodiment of a crystallization site that separates a precipitant solution from a screening solution and is adapted to pump out volatile vapor and mix the separate precipitant solution and screening solution. This alternative embodiment provides a construction that is conveniently susceptible to manufacture. As shown, a crystallization site 891 (which is preferably one site of a multi-site apparatus) according to this embodiment includes a structure 892 to which an upper and lower film are attached. Structure 892 and the upper and lower films define a chamber 893 in which the precipitant and screening solutions are disposed. Preferably, structure 892 is made of plastic or steel and has a circular hole that defines chamber 893. This circular hole can be easily machined, punched, or etched to form structure 892.

A hydrophobic mask 894 defines the areas in which the precipitant and screening solutions are held, as well as a channel 895 separating the solutions. Channel 895 can be used (in conjunction with the movement of the upper and lower films, described in detail below) to guide the precipitant and screening solutions toward each other if mixing is desired. Hydrophobic mask 894 can be applied to one or both of the upper and lower films.

Structure 892 further defines a passage 896 in communication with chamber 893. Passage 896 can be a passive or active vent or can be in communication with a passive or active vent. Passage 896 provides a passage through which accumulated volatile vapor can exit chamber 893 and air or gas can enter chamber 893.

The apparatus of FIG. 8D can be used in a manner similar to the methods described above in reference to FIGS. 8A-8C.

Figure 8E:
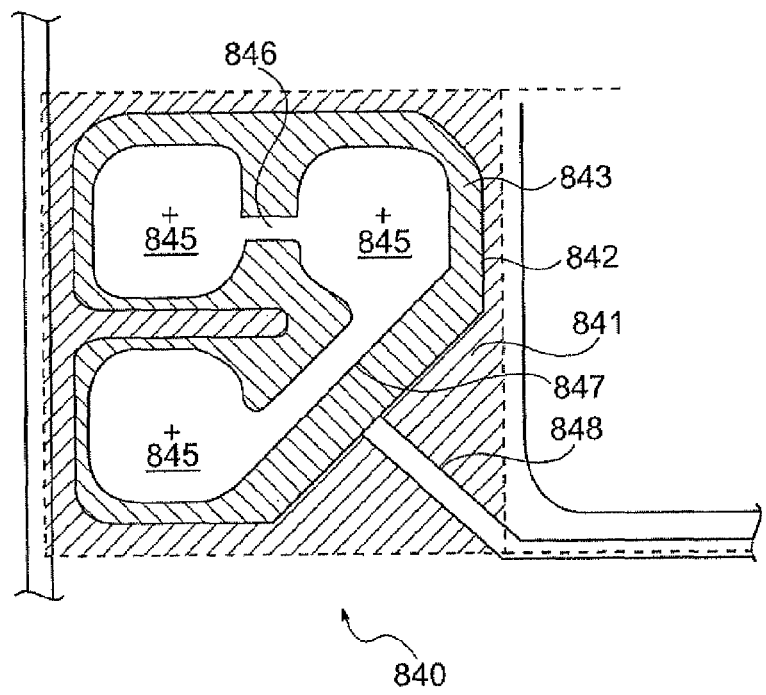
FIG. 8E is a schematic diagram of an alternative embodiment of a crystallization site that separates a precipitant solution from a screening solution, allows for two volumes of screening solution, and is adapted to pump out volatile vapor and mix the solutions, according to an embodiment of the present invention.

FIG. 8E illustrates an alternative embodiment of a crystallization site that separates the precipitant solution from the screening solution, allows for two volumes of screening solution, and is adapted to pump out volatile vapor and mix the solutions if desired. As shown, a crystallization site 840 (which is preferably one site of a multi-site apparatus) according to this embodiment includes a structure 841 to which an upper and lower film are attached. Structure 841 and the upper and lower films define a chamber 842 in which the precipitant and screening solutions are disposed. Preferably, structure 841 is made of plastic, steel, or pressure sensitive adhesive.

A hydrophobic mask 843 defines the areas in which the precipitant and screening solutions are held. These areas include precipitant solution area 844 and screening solution areas 845. Hydrophobic mask 843 also defines a channel 846 separating the screening solutions and a channel 847 separating one volume of screening solution from the precipitant solution Channels 846 and 847 can be used (in conjunction with the movement of the upper and lower films, described in detail below) to guide the precipitant and screening solutions toward each other if mixing is desired. Hydrophobic mask 843 can be applied to one or both of the upper and lower films.

Structure 841 further defines a passage 848 in communication with chamber 842. Passage 848 can be a passive or active vent or can be in communication with a passive or active vent. Passage 848 provides a passage through which accumulated volatile vapor can exit chamber 842 and air or gas can enter chamber 842.

The apparatus of FIG. 8E can be used in a manner similar to the methods described above in reference to FIGS. 8A-8C.

Figure 8F:
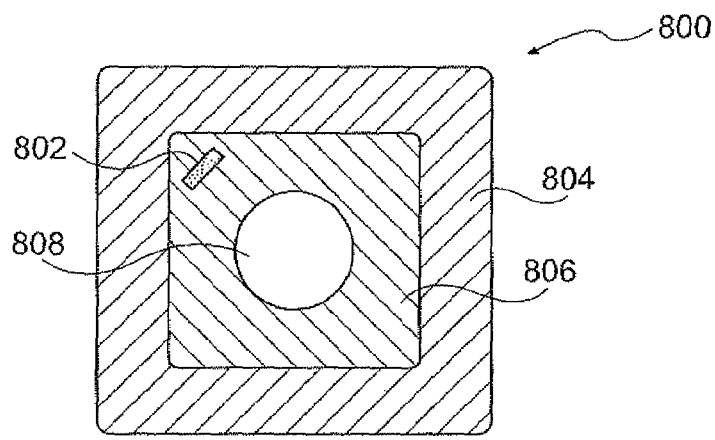
FIG. 8F is a schematic diagram of an exemplary crystallization site that has a single volume of precipitant solution and is adapted to pump out volatile vapor, according to an embodiment of the present invention.

FIG. 8F illustrates an exemplary crystallization site 800 that has a single volume of precipitant solution 808 and is adapted to pump out volatile vapor. As shown, crystallization site 800 includes a structure 804 that defines the sidewalls of the site 800. As described above, this structure 804 could be, for example, a lattice plate, a thermoformed plastic lattice plate, or a layer of punched, formed, die-cut, or printed pressure sensitive adhesive. A lower film is attached to the bottom side of structure 804. Optionally, the lower film has a hydrophobic mask 806 that helps hold precipitant solution 808 in place. An upper film is attached to the top side of structure 804, Together, structure 804 and the upper and lower films seal the crystallization site 800. Within this sealed site 800, volatile vapor evaporates off of precipitant solution 805, increasing the concentration of the molecules to be crystallized in precipitant solution 808, thereby promoting crystal growth within precipitant solution 808.

One of the films of the crystallization site 800 contains an active vent 802 that is normally closed when the pressure inside site 800 is equal to the ambient pressure. When a pressure differential is applied across the film, vent 802 opens to allow passage of volatile vapor out and ambient air or gas in. Reducing the outside pressure below that of the inside causes vent 802 to open to allow volatile vapor to escape. Increasing the outside pressure above that of the inside causes the vent 802 to open to allow ambient air or gas to enter site 800.

An embodiment of the present invention provides a method for forming crystals using the exemplary structure of FIG. 8F. According to this method, a volume (e.g., approximately 1 nl to 100 μl) of protein solution is deposited on the lower film inside hydrophobic mask 806. Then, a volume (e.g., approximately 1 nl to 100 μl) of screening solution is deposited on the lower film such that the protein solution and screening solution form a drop of precipitant solution 808. (The protein solution and screening solution could, of course, be placed in the reverse order.) Optionally, in forming the drop of precipitant solution 808, the protein and screening solutions could be mixed, for example, by stirring with a pipette. Structure 804 and the upper film are then placed over solution 808 to seal it within the site 800. Optionally, if not already mixed, the protein and screening solutions could be mixed at this point by movement of the films (described below). The site 800 is then incubated during which time volatile vapor evaporates off of solution 808. The gas environment within site 800 therefore accumulates volatile vapor from the solution 808.

The method continues by reducing the pressure outside the site 800 to below the pressure inside the site 800. This pressure differential causes vent 802 to open, thereby allowing volatile vapor to escape. The pressures inside and outside of site 800 are then allowed to equalize. As pressure equilibrium is reached, vent 802 closes.

The pressure outside site 800 is then increased above the reduced pressure inside the site, which causes vent 802 to open to allow ambient air or gas to enter site 800. The pressures inside and outside of site 800 are then allowed to equalize again. As pressure equilibrium is reached, vent 802 closes. With the gas environment inside of site 800 replaced with ambient air or gas, the evaporation of volatiles continues during a subsequent period of incubation until the next pumping cycle.

Figure 9:
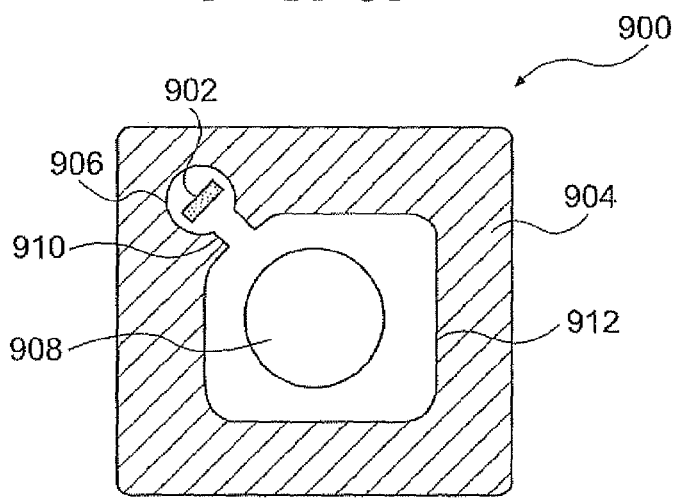
FIG. 9 is a schematic diagram of another exemplary crystallization site that has a single volume of precipitant solution and is adapted to pump out volatile vapor, according to an embodiment of the present invention.

FIG. 9 illustrates another exemplary crystallization site 900 that has protein and screening solution combined into a precipitant solution 908 and is adapted to pump out volatile vapor. Site 900 is similar in most respects to site 800 of FIG. 8B, except that the structure 904 of site 900 defines two chambers connected by a passage, instead of a single chamber as in site 800. As shown in FIG. 9, structure 904 defines a first chamber 906 and a second chamber 912 connected by a gas passage 910. Precipitant solution 908 is disposed in the second chamber 912. The active vent 902, which is formed in either the upper or lower film, is aligned with the first chamber 906. Volatile vapor flows from precipitant solution 908 through gas passage 910, into chamber 906, and out of vent 902, to concentrate precipitant solution 908 and thereby promote crystal growth within precipitant solution 908. The apparatus of FIG. 9 is used in a manner similar to the method described above in reference to FIG. 8B.

Figure 10:
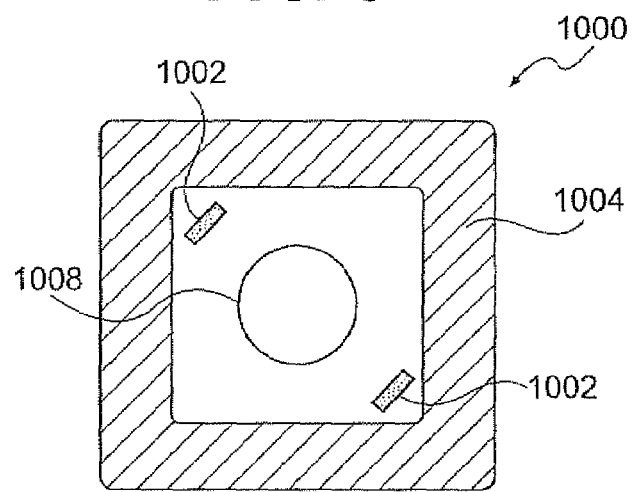
FIG. 10 is a schematic diagram of a crystallization site that has two vents, according to an embodiment of the present invention.

FIG. 10 illustrates an alternative embodiment of a crystallization site 1000, which has two active vents 1002, instead of one. In this exemplary crystallization site 1000, a structure 1004 defines the sidewalls of the site 1000. A lower film is attached to the bottom side of structure 1004. A precipitant solution 1008, which includes protein and screening solution, is disposed on the lower film. An upper film is attached to the top side of structure 1004. Together, structure 1004 and the upper and lower films seal the crystallization site 1000. Within this sealed site 1000, volatile vapor evaporates off of precipitant solution 1008, thereby concentrating precipitant solution 1008 and promoting crystal growth within precipitant solution 1008.

In the alternative embodiment of FIG. 10, the two vents 1002, each of which is disposed in either the upper or lower film, increase (in comparison to one vent) the rate at which volatile vapor can be pumped out. As with the above-described vents, the vents 1002 are normally closed when the pressure inside site 1000 is equal to the ambient pressure, and open when a pressure differential is applied across the upper film. As one of skill in the art would appreciate, in addition to the use of one or two vents, the present invention could use any number of vents, as needed to accommodate the rate at which volatile vapor must be removed to satisfy a specific application.

In addition to the number of vents, the placement of the vents can also vary. A vent can be positioned in an area of the film that is well supported (e.g., near the corner of a chamber defined by the sidewall structure, such as structure 1004), to avoid tearing the film at an endpoint of the vent. A vent is preferably spaced apart from the evaporating solution to avoid the solution's wetting the film in the area of the vent and possibly leaking through the vent. FIGS. 5A, 5B, 10, and 11 show vents positioned near the corner of the sidewall structure. The site 900 of FIG. 9, on other the hand, provides more support for the film in the area of vent 902 by positioning it over chamber 906.

The size of vent can also vary to accommodate different pumping conditions. The larger a vent, the faster any differential pressure applied across the film will be equalized. In one exemplary implementation using a crystallization site of a 96-well microplate and 0.001 inch-hick Teflon™ film, the vent could be approximately 0.005 to 0.050 inches. For a site of 384-well plate and 0.001 inch-thick Teflon™ film, the vent could be approximately 0.001 to 0.030 inches in length. For a site of a 1536-well plate and 0.001 inch-thick Teflon™ film, the vent could be approximately 0.001 to 0.015 inches in length.

Although FIGS. 8A-10 illustrate single crystallization sites, one of ordinary skill in the art would appreciate that the illustrated structures could be applied to a multiple site apparatus, for example, having 96, 384, or 1536 sites. In such case, the structure 854, 804, 904, or 1004 would be a lattice providing a through-hole for each site. In addition, to apply the pressure differential across a film, the entire device would preferably be placed under vacuum (to remove volatile vapor from the sites) or under pressure (to add ambient air or gas to the sites).

Figure 11:
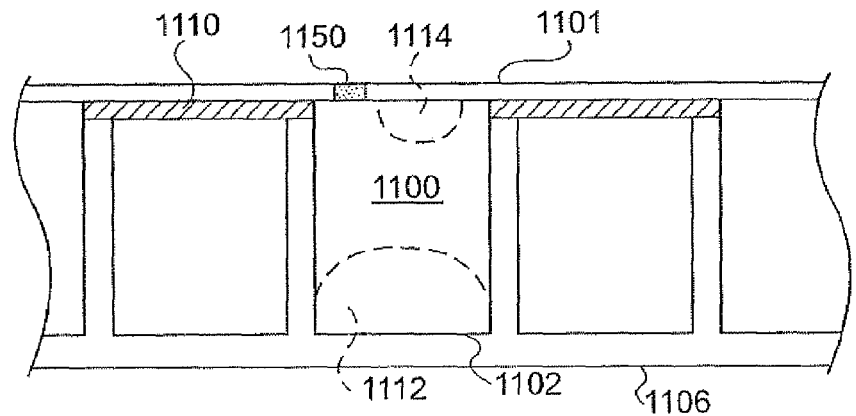
FIG. 11 is a schematic diagram of a cross-sectional side view of an exemplary crystallization site that has a microplate covered by a film and from which volatile vapor can be pumped, according to an embodiment of the present invention.

In another embodiment of the present invention, FIG. 11 illustrates a cross-sectional side view of an exemplary crystallization site 1100 from which volatile vapor can be pumped. In this example, site 1100 is formed by a microplate 1106 covered by a film 1101. Microplate 1106 defines a plurality of wells, one of which is well 1102. In preferred embodiments, the microplate 1106 is a polystyrene 96-, 384-, or 1536-well microplate. Film 1101 is adhered to the upper rims of microplate 1106 to seal each well. Film 1101 also preferably includes a hydrophobic coating 1110 to help contain the solutions. Although not shown, the upper rims of microplate 1106 could also be covered with a layer of sealant (e.g., an adhesive malleable sealant or an adhesive gasket) to help seal any gaps between film 1101 and microplate 1106.

Film 1101 includes an active vent disposed over each of the wells of microplate 1106, as illustrated by vent 1150 disposed over well 1102. Vent 1150 is normally closed when the pressure inside site 1100 is equal to the ambient pressure, and open when a pressure differential is applied across film 1101.

The crystallization site 1100 of FIG. 11 can be used either with a separate precipitant solution and screening solution or with a single volume of precipitant solution that includes protein and screening solution. According to a first method using a separate precipitant solution and screening solution, as shown in FIG. 11, a screening solution 1112 is first deposited in well 1102. A precipitant solution 1114 is then deposited on the bottom surface of film 1101, while film 1101 is inverted and before film 1101 is placed over microplate 1106. With precipitant solution 1114 in place, film 1101 is then turned over and placed over microplate 1106 such that precipitant solution 1114 is suspended over screening solution 1112 within the sealed site 1100. Microplate 1106 is then incubated, during which time vapor diffusion occurs from precipitant solution 1114 to screening solution 1112. Because of this vapor diffusion, the gas environment within site 1100 accumulates volatile vapor.

After a predetermined period of incubation, microplate 1106 is placed under vacuum. The reduction in ambient pressure to below the pressure within site 1100 causes vent 1150 to open, allowing the accumulated volatile vapor to escape. Preferably, microplate 1106 is held under vacuum long enough for the pressure in each well of the microplate 1106 to equalize with the lower outside pressure. As pressure equilibrium is reached, vent 1150 closes and seals site 1100.

The vacuum is then released from microplate 1106. Because site 1100 is still under partial vacuum at this point and the pressure outside site 1100 is now greater than the pressure inside, vent 1150 opens and allows ambient air or gas to enter site 1100. This ambient air or gas preferably has fewer volatile vapors than the gas pumped out of the site 1100. In an alternative embodiment, instead of simply releasing the vacuum from microplate 1106 and allowing it to reach standard atmospheric pressure inside each site, the microplate 1106 is further placed under pressure to help force ambient air or gas into the sites. In either case, once the pressure outside site 1100 equalizes with the pressure inside site 1100, vent 1150 closes and seals site 1100.

With the volatile vapor pumped out of site 1100 and replaced with ambient air or gas, microplate 1106 is then incubated, during which time further vapor diffusion occurs and additional volatile vapor accumulates in site 1100. The pumping cycle is then repeated at a frequency that provides the desired vapor diffusion and rate of concentration of the precipitant solution 1114. To monitor the initial formation of a crystal and/or the crystal growth rate, microplate 1106 is preferably read between incubation and pumping cycles. As an example, the pressurization cycles can take place inside a reader that provides the pumping function.

A second method for growing crystals uses the apparatus of FIG. 11 with a single volume of precipitant solution that includes protein and screening solution. In this case, no solution (solution 1114) is deposited on film 1101. Instead, a protein solution is first deposited in well 1102. A screening solution is then deposited in well 1102 so that the two solutions form a drop of precipitant solution 1112. (The protein and screening solutions could, of course, be deposited in the reverse order.) Film 1101 is then placed over microplate 1106. Microplate 1106 is then incubated, during which time volatile vapor evaporates off of solution 1112. As a result of this evaporation, the gas environment within site 1100 accumulates volatile vapor.

After a predetermined period of incubation, microplate 1106 is placed under vacuum. The reduction in ambient pressure to below the pressure within site 1100 causes vent 1150 to open, allowing the volatile vapor to escape. Preferably, microplate 1106 is held under vacuum long enough for the pressure in each well of the microplate 1106 to equalize with the lower outside pressure. As pressure equilibrium is reached, vent 1150 closes and seals site 1100.

The vacuum is then removed from microplate 1106. Because site 1100 is still under partial vacuum at this point and the pressure outside site 1100 is now greater than the pressure inside, vent 1150 opens and allows ambient air or gas to enter site 1100. This ambient air or gas preferably has fewer volatile vapors than the gas pumped out of the site 1100. In an alternative embodiment, instead of simply releasing the vacuum from microplate 1106 and allowing it to reach standard atmospheric pressure, the microplate 1106 is pressurized to help force ambient air or gas into the sites. In either case, once the pressure outside site 1100 equalizes with the pressure inside site 1100, vent 1150 closes and seals site 1100.

With the volatile vapor pumped out of site 1100 and replaced with ambient air or gas, microplate 1106 is then incubated, during which time further evaporation occurs and additional volatile vapor accumulates in site 1100. The pumping cycle is then repeated at a frequency that provides the desired rate of concentration of precipitant solution 1112. To monitor the initial formation of a crystal and/or the crystal growth rate, microplate 1106 is preferably read between incubation and pumping cycles.

Figure 12:
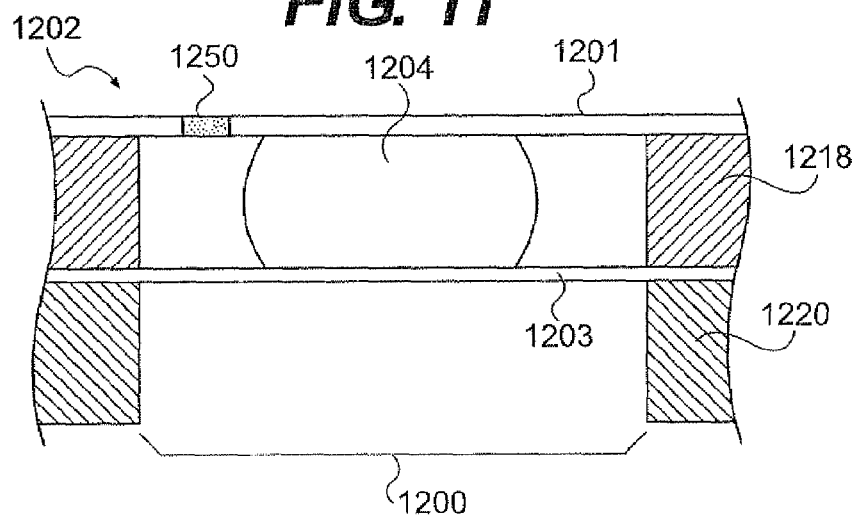
FIG. 12 is a schematic diagram of a cross-sectional side view of an exemplary crystallization site that has an upper and lower film and from which volatile vapor can be pumped, according to an embodiment of the present invention.

In another embodiment of the present invention, FIG. 12 illustrates a cross-sectional side view of an exemplary crystallization site 1200 from which volatile vapor can be pumped. In this example, site 1200 is one site of a multi-site crystallization apparatus 1202. Apparatus 1202 includes a lower film 1203 supported by a lower plate 1220 and an upper film 1201 supported by an upper plate 1218. The upper plate 1218 includes through-holes that define each site. These through-holes are areas in which the bottom surface of the upper film 1201 is not supported by the upper plate 1218, i.e., there is a hole in the upper plate 1218. The upper plate 1218 is placed on top of the lower film 1203. In this way, each through-hole of upper plate 1218, along with upper film 1201 and lower film 1203, provide a sealed site, such as site 1200. Although not shown, layers of adhesive or some other bonding material could be used between the plates and films to help seal the sites.

Upper film 1201 includes active vents disposed over each site, such as the vent 1250 disposed over site 1200. Vent 1250 is normally closed when the pressure inside site 1200 is equal to the ambient pressure, and open when a pressure differential is applied across film 1201. Optionally, vent 1250 could be disposed in lower film 1203 instead of upper film 1201.

A precipitant solution 1204, which includes protein and screening solution, is disposed within site 1200. Preferably, as shown in FIG. 12, solution 1204 wets both the bottom surface of film 1201 and the upper surface of film 1203. This contact helps contain the solution 1204 (perhaps with the aid of hydrophobic masks on films 1201 and 1203) and provides a flat surface through which solution 1204 can be more accurately and conveniently monitored for crystal growth, using, for example, electromagnetic readers.

An embodiment of the present invention provides a method for forming crystals using the exemplary structure of FIG. 12. According to this method, a protein solution is first deposited on film 1203, with the upper plate 1218 and upper film 1201 not yet joined with the lower film 1203 and lower plate 1220. A screening solution is then deposited on or in contact with the protein solution so that the two solutions start to mix to form a drop of precipitant solution 1204. Optionally, in forming the drop of precipitant solution 1204, the protein and screening solutions are mixed, for example, by stirring with a pipette.

Upper plate 1218 and upper film 1201 are then placed over lower film 1203, with a through-hole of upper plate 1218 around precipitant solution 1204. Precipitant solution 1204 wets upper film 1201 and lower film 1203. Precipitant solution 1204 is therefore contained within the site 1200 defined by the upper film 1201, the lower film 1203, and the through-hole of upper plate 1218. Optionally, if not already mixed, the protein and screening solutions could be mixed at this point by movement of the films (described below). Apparatus 1202 is then incubated, during which time volatiles evaporate off of solution 1204. Because of this evaporation, the gas environment within site 1200 accumulates volatile vapor.

After a predetermined period of incubation, apparatus 1202 is placed under vacuum. The reduction in ambient pressure to below the pressure within site 1200 causes vent 1250 to open, allowing the volatile vapor to escape. Preferably, apparatus 1202 is held under vacuum long enough for the pressure in each site of apparatus 1202 to equalize with the lower outside pressure. As pressure equilibrium is reached, vent 1250 closes and seals site 1200.

The vacuum is then removed from apparatus 1202. Because site 1200 is still under partial vacuum at this point and the pressure outside site 1200 is now greater than the pressure inside, vent 1250 opens and allows ambient air or gas to enter site 1200. This ambient air or gas preferably has fewer volatile vapors than the gas pumped out of the site 1200. In an alternative embodiment, instead of simply releasing the vacuum from apparatus 1202 and allowing it to reach standard atmospheric pressure, apparatus 1202 is pressurized to help force ambient air or gas into the sites. In either case, once the pressure outside site 1200 equalizes with the pressure inside site 1200, vent 1250 closes and seals site 1200.

With the volatile vapor pumped out of site 1200 and replaced with ambient air or gas, apparatus 1202 is then incubated, during which time further evaporation occurs and additional volatile vapor accumulates in site 1200. The pumping cycle is then repeated at a frequency that provides the desired rate of concentration of precipitant solution 1204. To monitor the initial formation of a crystal and/or the crystal growth rate, apparatus 1202 is preferably read between incubation and pumping cycles. Having solution 1204 sandwiched between upper film 1201 and lower film 1203 improves the efficiency and accuracy of these readings.

Figure 13A:
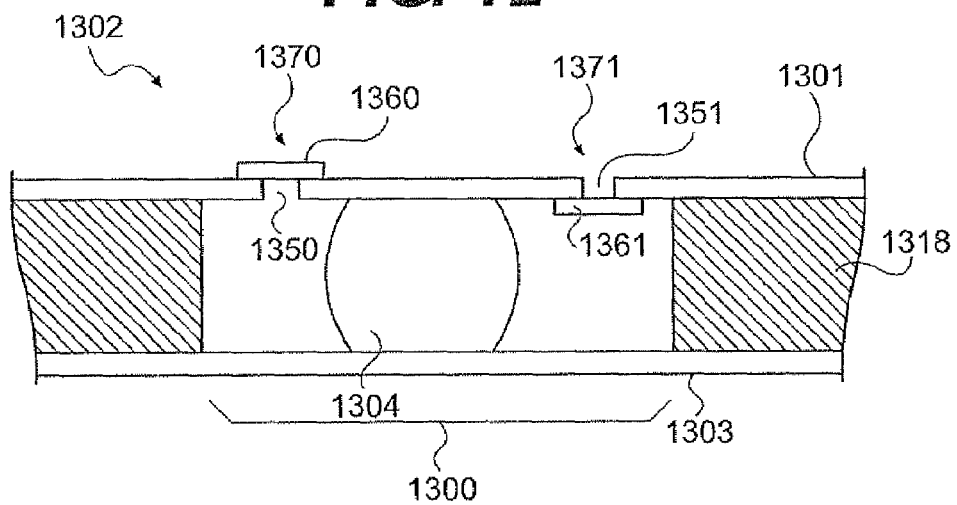
FIG. 13A is a schematic diagram of a cross-sectional side view of an exemplary crystallization apparatus having a crystallization site with flap valves through which volatile vapor can be pumped, according to an embodiment of the present invention.

In another embodiment of the present invention, FIG. 13A illustrates a cross-sectional side view of another exemplary apparatus 1302 having a crystallization site 1300 with an active vent. In this example, the active vent is provided by flap valves through which volatile vapor can be pumped. As shown, apparatus 1302 includes a support structure 1318 sandwiched between two layers 1301 and 1303. Upper layer 1301 and lower layer 1303 can be made of film as described above, but are preferably made of a rigid material, such as glass or rigid plastic. Structure 1318 includes through-holes that define each site, such as site 1300. The solution 1304 is disposed in site 1300, sealed by structure 1318, lower layer 1303, and upper layer 1301.

Upper layer 1301 includes two flap valves, one that acts as a one-way outlet valve and another that acts as a one-way inlet valve. (Optionally, one or both of these flap valves could be disposed in lower layer 1303.) The outlet valve 1370 is provided by an inlet opening 1350 covered by a flap 1360 disposed on the side of layer 1301 that is outside site 1300. Flap 1360 opens away from site 1300 to allow the passage of volatile vapor out of site 1300, and closes against layer 1301 to prevent the entry of outside gas or air into site 1300. The inlet valve 1371 is provided by an inlet opening 1351 covered by a flap 1361 disposed on the side of layer 1301 that is inside site 1300. Flap 1361 opens into site 1300 to allow the passage of outside gas or air into site 1300, and closes against layer 1301 to prevent the passage of volatile vapor outside of site 1300.

Outlet valve 1370 and inlet valve 1371 act in conjunction to provide the active vent and pumping feature of this embodiment of the present invention. The valves 1370 and 1371 are normally closed. When a pressure differential is applied across layer 1301, one valve opens and the other remains closed. If the pressure inside site 1300 is greater than the pressure outside, then flap 1360 of outlet valve 1370 opens and flap 1361 of the inlet valve 1371 remains closed, pressed against the inside of layer 1301. If the pressure inside site 1300 is less than the pressure outside, then flap 1361 of inlet valve 1371 opens and flap 1360 of outlet valve 1370 remains closed, pressed against the outside of layer 1301.

In accordance with an exemplary method for forming crystals using apparatus 1302 of FIG. 13A, a protein solution is first deposited on layer 1303, with the upper layer 1301 not yet covering site 1300. A screening solution is then deposited on or in contact with the protein solution so that the two solutions form a drop of precipitant solution 1304. Optionally, in forming the drop of precipitant solution 1304, the protein and screening solutions could be mixed, for example, by stirring with a pipette.

Upper layer 1301 (and structure 1318, if it is not already in place) is then placed over lower layer 1303. Solution 1304 is therefore contained within the site 1300 defined by the upper layer 1301, the lower layer 1303, and the through-hole of structure 1318. Optionally, if not already mixed, the protein and screening solutions could be mixed at this point by movement of a layer if either of the layers is not rigid (described below). Apparatus 1302 is then incubated, during which time volatiles evaporate off of solution 1304. As a result of this evaporation, the gas environment within site 1300 accumulates volatile vapor.

After a predetermined period of incubation, apparatus 1302 is placed under vacuum. The reduction in ambient pressure to below the pressure within site 1300 causes flap 1360 of outlet valve 1370 to open, allowing the accumulated volatile vapor to escape. At the same time, the higher pressure within site 1300 keeps flap 1361 of inlet valve 1371 closed. Preferably, apparatus 1302 is held under vacuum long enough for the pressure in site 1300 to equalize with the outside vacuum pressure. As pressure equilibrium is reached, flap 1360 of outlet valve 1370 closes.

The vacuum is then released from apparatus 1302. Because site 1300 is still under partial vacuum at this point and the pressure outside site 1300 is now greater than the pressure inside, flap 1361 of inlet valve 1371 opens and allows ambient air or gas to enter site 1300. At the same time, the lower pressure within site 1300 holds flap 1360 of outlet valve 1371 closed against the upper layer 1301. The ambient air or gas entering the site 1300 preferably contains fewer volatile vapors than the gas pumped out of the site 1300. In an alternative embodiment, instead of simply releasing the vacuum from apparatus 1302 and allowing it to reach standard atmospheric pressure, apparatus 1302 is pressurized to help force ambient air or gas into the sites. In either case, once the pressure outside site 1300 equalizes with the pressure inside site 1300, flap 1361 of inlet valve 1371 closes and seals site 1300.

With the volatile vapor pumped out of site 1300 and replaced with ambient air or gas, apparatus 1302 is then incubated, during which time further evaporation occurs and additional volatile vapor accumulates in site 1300. The pumping cycle is then repeated at a frequency that provides the desired rate of concentration of precipitant solution 1304. To monitor the initial formation of a crystal and/or the crystal growth rate, apparatus 1302 is preferably read between incubation and pumping cycles. Having solution 1304 sandwiched between upper layer 1301 and lower layer 1303 improves the efficiency and accuracy of these readings.

FIG. 13B illustrates another example of a site 1352 of a crystallization apparatus 1350 having an active vent, according to an embodiment of the present invention. In this example, the active vent is provided by holes in compliant film that are closed by resting against adjacent structures of the crystallization apparatus. As shown, crystallization apparatus 1350 includes a lower film 1354 supported by a lower plate 1356 and an upper film 1358 supported by an upper plate 1360. The upper plate 1360 includes through-holes that define each site. These through-holes are areas in which the bottom surface of the upper film 1358 is not supported by the upper plate 1360, i.e., there is a hole in the upper plate 1360. The upper plate 1360 is placed on top of the lower film 1354. In this way, each through-hole of upper plate 1360, along with upper film 1358 and lower film 1354, provide a sealed site, such as site 1352.

To provide the active vent, upper film 1358 includes a hole 1362 that is disposed adjacent to a portion of upper plate 1360 and lower film 1354 includes a hole 1364 that is disposed adjacent to a portion of lower plate 1356. In this embodiment upper plate 1360 and lower plate 1356 are offset to enable the hole 1364 of lower film 1354 to be disposed adjacent to a portion of lower plate 1356.

Apparatus 1350 also includes adhesive layers 1366 and 1368. Adhesive layer 1366 bonds upper film 1358 to upper plate 1360. Importantly, however, the area of upper film 1358 around hole 1362 is not bonded to upper plate 1360. Likewise, adhesive layer bonds lower film 1354 to lower plate 1356, but the area of lower film 1354 around hole 1364 is not bonded to lower plate 1356. In this manner, as represented by the dotted line 1370, upper film 1358 can move away from upper plate 1360 in the area around hole 1362, thereby opening hole 1362. Likewise, as represented by the dotted line 1372, lower film 1354 can move away from lower plate 1356 in the area around hole 1364, thereby opening hole 1364.

An embodiment of the present invention provides a method for forming crystals using the crystallization apparatus 1350 of FIG. 13B. According to this method, a protein solution is first deposited on film 1354, with the upper plate 1360 and upper film 1358 not yet joined with the lower film 1354 and lower plate 1356. A screening solution is then deposited on or in contact with the protein solution so that the two solutions start to mix to form a drop of precipitant solution 1380. Optionally, in forming the drop of precipitant solution 1380, the protein and screening solutions are mixed, for example, by stirring with a pipette.

Upper plate 1360 and upper film 1358 are then placed over lower film 1354, with a through-hole of upper plate 1360 around precipitant solution 1380. Precipitant solution 1380 wets upper film 1358 and lower film 1354. Precipitant solution 1380 is therefore contained within the site 1352 defined by the upper film 1358, the lower film 1354, and the through-hole of upper plate 1360. Optionally, if not already mixed, the protein and screening solutions could be mixed at this point by movement of the films (described below). Apparatus 1350 is then incubated, during which time volatiles evaporate off of solution 1380. Because of this evaporation, the gas environment within site 1352 accumulates volatile vapor.

After a predetermined period of incubation, apparatus 1350 is placed under vacuum. The reduction in ambient pressure to below the pressure within site 1352 forces upper film 1358 and lower film 1354 outward from the higher internal pressure of site 1352. This outward force causes upper film 1358 to bulge as represented by the dotted line 1370, which in turn creates a space between the hole 1362 of upper film 1358 and upper plate 1360. This space opens hole 1362 and allows the accumulated volatile vapor to escape. At the same time, the outward force on lower film 1354 keeps the hole 1364 of lower film 1354 pressed against lower plate 1356, thereby keeping the hole 1364 closed.

Preferably, apparatus 1350 is held under vacuum long enough for the pressure in each site of apparatus 1350 to equalize with the lower outside pressure. As pressure equilibrium is reached, upper film 1358 returns to its original position with hole 1362 closed against upper plate 1360.

The vacuum is then removed from apparatus 1350. Because site 1352 is still under partial vacuum at this point and the pressure outside site 1352 is now greater than the pressure inside, upper film 1358 and lower film 1354 are forced inward. This inward force causes lower film 1354 to bulge as represented by the dotted line 1372, which in turn creates a space between the hole 1364 of lower film 1354 and lower plate 1356. This space opens hole 1364 and allows ambient air or gas to enter site 1352. At the same time, the inward force on upper film 1358 keeps the hole 1362 of upper film 1358 pressed against upper plate 1360, thereby keeping the hole 1362 closed.

The ambient air or gas that enters hole 1364 preferably has fewer volatile vapors than the gas pumped out of the site 1352. In an alternative embodiment, instead of simply releasing the vacuum from apparatus 1350 and allowing it to reach standard atmospheric pressure, apparatus 1350 is pressurized to help force ambient air or gas into the sites. In either case, once the pressure outside site 1352 equalizes with the pressure inside site 1352, lower film 1354 returns to its original position with hole 1364 closed against lower plate 1356, thereby sealing site 1352.

With the volatile vapor pumped out of site 1352 and replaced with ambient air or gas, apparatus 1352 is then incubated, during which time further evaporation occurs and additional volatile vapor accumulates in site 1352. The pumping cycle is then repeated at a frequency that provides the desired rate of concentration of precipitant solution 1380. To monitor the initial formation of a crystal and/or the crystal growth rate, apparatus 1350 is preferably read between incubation and pumping cycles. Having solution 1350 sandwiched between upper film 1358 and lower film 1354 improves the efficiency and accuracy of these readings.

FIGS. 13C and 13D illustrate alternative embodiments for providing an active vent using holes in compliant film that are closed by resting against adjacent structures of a crystallization apparatus. FIG. 13C shows a crystallization apparatus 1385 that includes a lower plate 1386 that has smaller through-holes than the upper plate 1387 (as opposed to having the same size through-holes and being offset, as in FIG. 13B). The smaller through-holes in lower plate 1386 provide a surface against which the hole 1388 of lower film 1389 can be closed.

FIG. 13D illustrates a crystallization apparatus 1390 that includes an upper plate 1391 and a lower plate 1392 having through-holes of the same size, but using an adhesive layer 1393 to create a space between the upper plate 1391 and the lower plate 1392 in which the lower film 1394 can move. This movement opens and closes a hole 1395 disposed in the lower film 1394 in the same manner as described above in reference to FIG. 13A. The space in which lower film 1394 can move is created by the thickness of adhesive layer 1393 and the distance that adhesive layer 1393 is held back from the portion of upper plate 1391 forming the inside wall of the site 1396.

FIGS. 14A, 14B, 15A, and 15B illustrate a mixing function that can be provided by embodiments of the present invention that sandwich a solution between surfaces, at least one of which is formed by a flexible material such as compliant film. The compliant film moves in and out (or up and down), which promotes mixing between two independently placed solutions (e.g., a protein solution followed by a screening solution). Such mixing can be especially helpful if the either of the two solutions is viscous. In an embodiment of the present invention, the mixing is completed before incubation (and the start of the concentration process) and is accomplished with high frequency, short duration, low pressure differential pumping, which moves the compliant film(s) rapidly to induce the mixing.

Figure 14A:
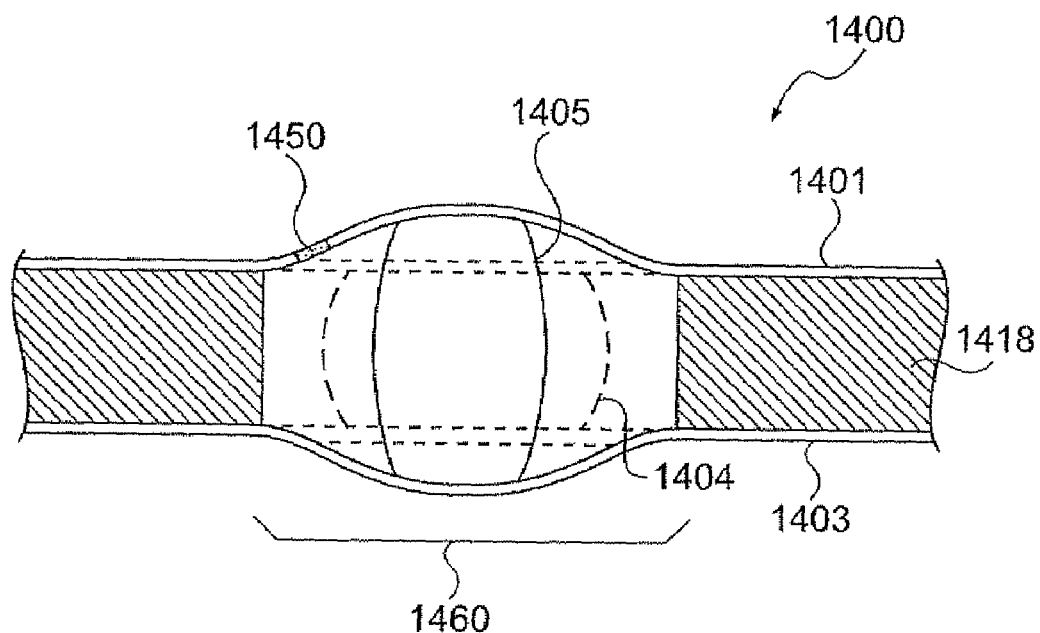
FIGS. 14A and 14B are schematic diagrams of a precipitant solution sandwiched between an upper compliant film and a lower compliant film, illustrating a mixing function, according to an embodiment of the present invention.
Figure 15A:
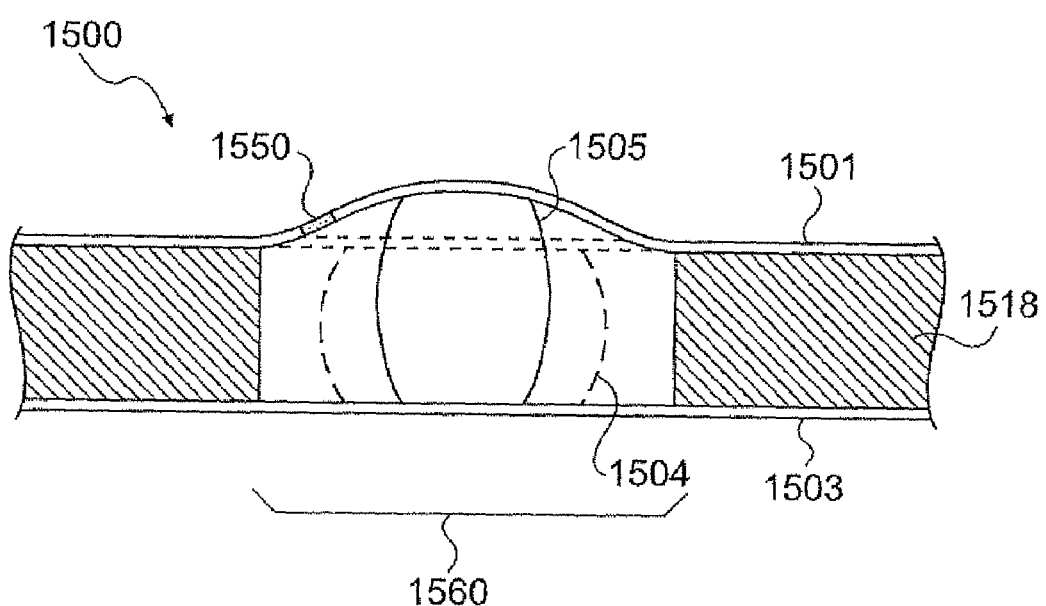
FIGS. 15A and 15B are schematic diagrams of a precipitant solution sandwiched between an upper compliant film and a lower noncompliant surface, illustrating a mixing function, according to an embodiment of the present invention.
Figure 14B:
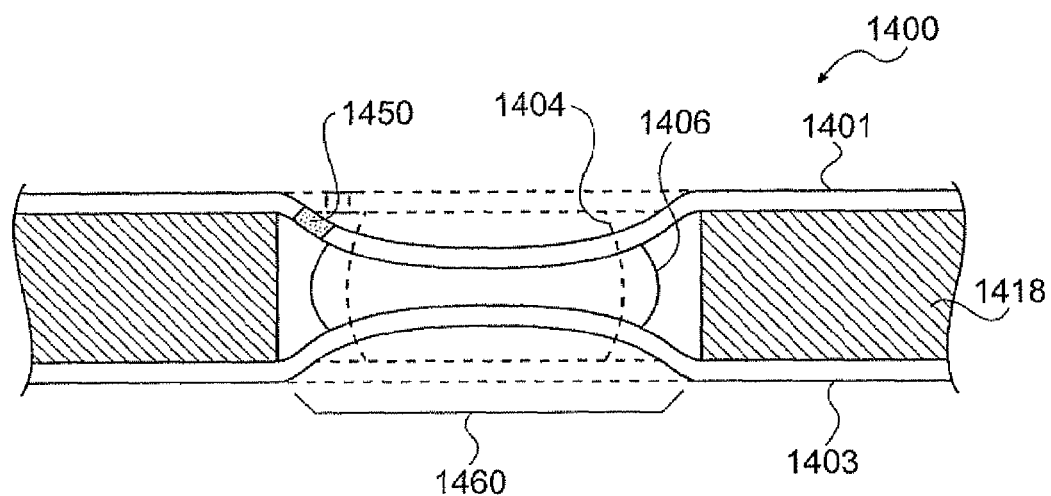
Figure 15B:
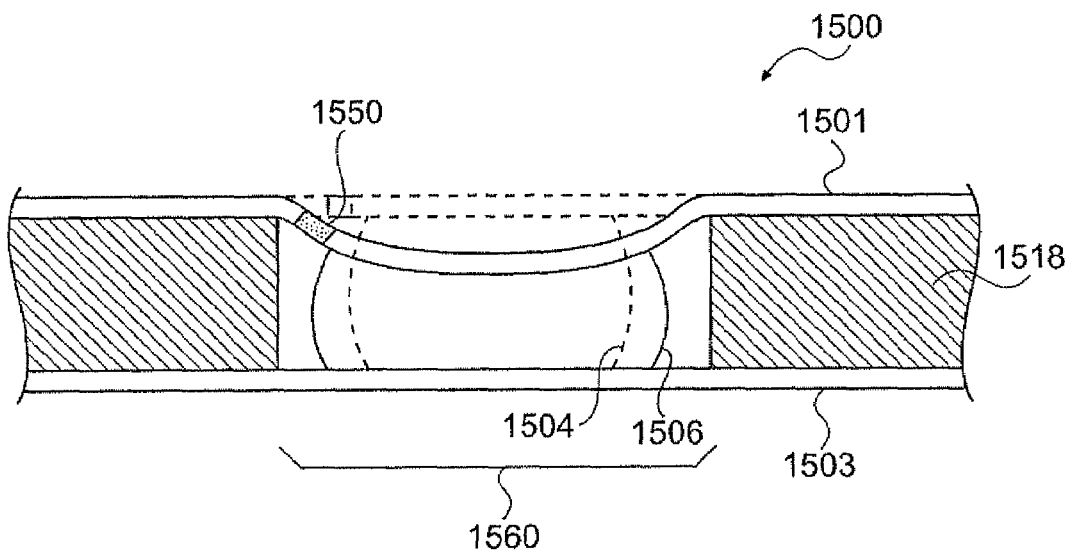

FIGS. 14A and 14B illustrate a combined protein and screening solution sandwiched between an upper compliant film 1401 and a lower compliant film 1403. FIGS. 15A and 15B illustrate a combined protein and screening solution sandwiched between an upper compliant film 1501 and a lower noncompliant structure 1503. The degree of mixing depends on, for example, the compliance of the sandwich film(s), the dimensions of the unsupported film, and the pressure differential applied between the inside and outside of the site. The compliance depends on the structural properties of the film as affected by, for example, the thickness and composition of the material of the film. The amount of mixing can therefore be controlled by choosing sandwich film that provides the desired amount of compliance, by choosing appropriate dimensions of the unsupported area of the film, by choosing an appropriate pressure differential, and by choosing an appropriate rate at which the pressure differential is applied.

The exemplary apparatus 1400 shown in FIGS. 14A and 14B demonstrates the movement of a solution between a first position 1404, a second position 1405, and third position 1406. The solution is sealed within a site 1460 defined by a sidewall structure 1418, an upper film 1401, and a lower film 1403. Sidewall structure 1418 could be, for example, a stainless steel lattice plate, a punched, formed, die-cut, or printed pressure sensitive adhesive, or a thermoformed plastic lattice plate. Upper film 1401 has an active vent 1450 that is normally closed.

To begin mixing, apparatus 1400 is rapidly placed under a vacuum. With the pressure outside of site 1460 lower than the pressure inside of site 1460, the compliant films 1401 and 1403 bulge as shown by the second position 1405 in FIG. 14A. This bulging changes the shape of the solution, thereby inducing mixing. When the pressure differential across upper film 1401 increases enough, the vent 1450 opens and allows the higher pressure volatile vapor to escape. Then, with the inside pressure equal with the outside vacuum pressure, the bulges in upper film 1401 and lower film 1403 subside, causing the solution to move back to the first position 1404. When the external vacuum is released, the opposite action occurs, with the films 1401 and 1403 bulging inward, as shown in FIG. 14B.

As the pumping cycles repeat, the solution moves between the first position 1404, the second position 1405, and the third position 1406. These movements mix the combined protein and screening solutions to provide a more evenly dispersed precipitant solution with which to begin the crystallization process (e.g., incubating as the next step after mixing). In addition, with a suitable detection system (e.g., a laser light scattering detection system) providing feedback on concentration gradients, the movements can be controlled to mix the solutions at a desired rate to a achieve a desired diffusion.

The exemplary apparatus 1500 shown in FIGS. 15A and 15B also demonstrates the movement of a solution between a first position 1504, a second position 1505, and third position 1506, but using only one compliant film 1501. The solution is sealed within a site 1560 defined by a sidewall structure 1518, an upper film 1501, and a lower structure 1503. Upper film 1501 has an active vent 1550 that is normally closed. Sidewall structure 1518 could be, for example, a stainless steel lattice plate, a punched, formed, die-cut, or printed pressure sensitive adhesive, or a thermoformed plastic lattice plate. Lower structure 1503 could be, for example, glass or a rigid plastic.

To begin the mixing, apparatus 1500 is rapidly placed under a vacuum. With the pressure outside of site 1560 lower than the pressure inside of site 1560, the air or gas inside the site expands and the compliant film 1501 expands and bulges as shown by the second position 1505 in FIG. 15A. This bulging changes the shape of the solution, thereby inducing mixing. When the pressure differential across upper film 1501 increases enough, the vent 1550 opens and allows the higher pressure volatile vapor to escape. Then, with the inside pressure equal with the outside vacuum pressure, the bulge in upper film 1501 subsides causing the solution to move back to the first position 1504. When the external vacuum is released, the opposite action occurs, with the upper film 1501 bulging inward, as shown in FIG. 15B.

As the pumping cycles repeat, the solution moves between the first position 1504, the second position 1505, and the third position 1506. These movements mix the combined protein and screening solutions to provide a more evenly dispersed precipitant solution with which to begin the crystallization process.

Figure 16:
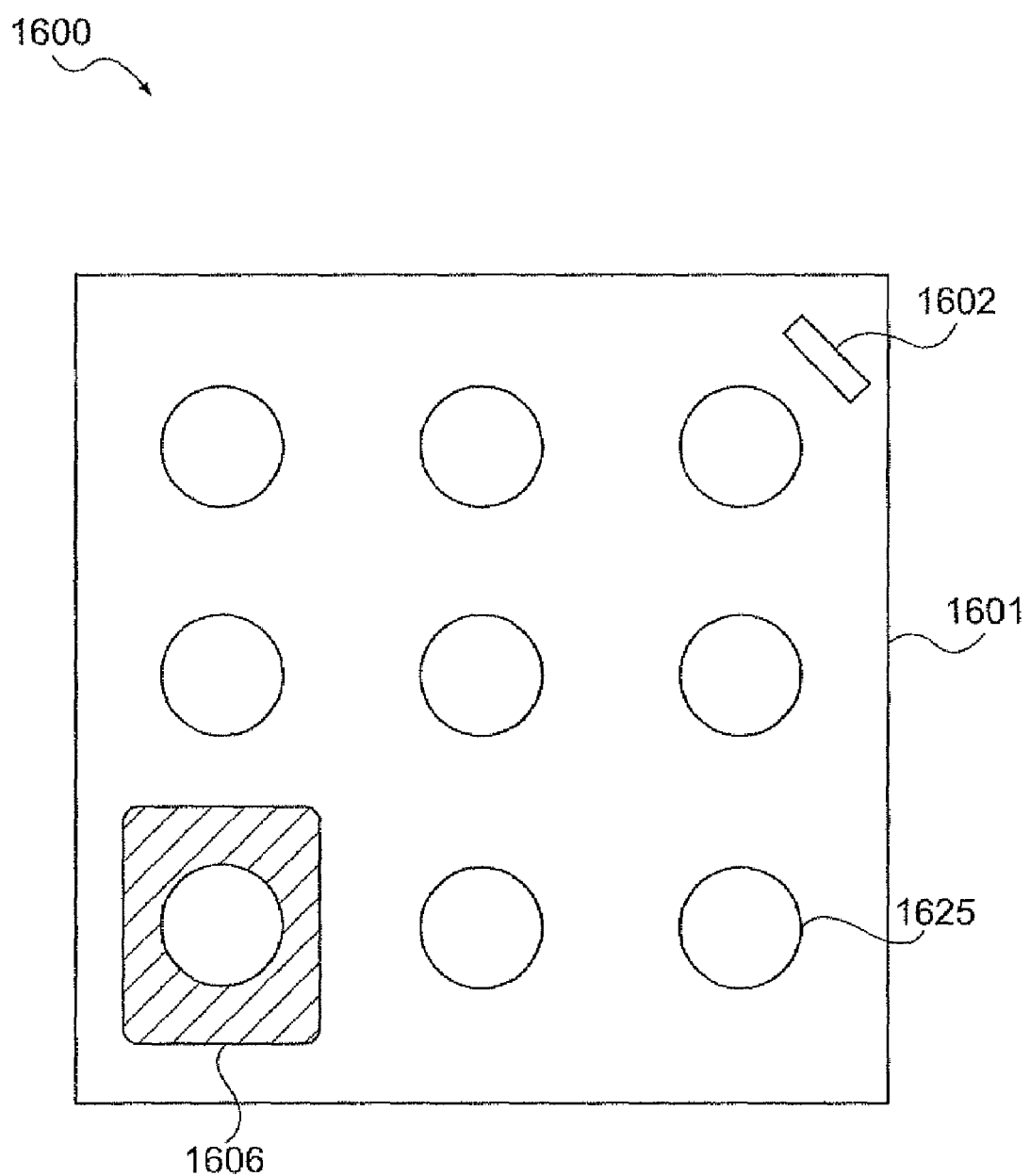
FIG. 16 is a schematic diagram of a single crystallization site that contains a plurality of solutions and can be pumped to remove volatile vapor, according to an embodiment of the present invention.

FIG. 16 illustrates a further embodiment of the present invention in which a single site 1600 containing a plurality of solutions 1625 can be pumped to remove volatile vapor. This configuration allows the placement of solutions 1625 containing different concentrations or variations of the same screening solution in a single site 1600. In this manner, the single site 1600 can serve both a screening and optimization function. In other words, the single site 1600 can not only determine if a screening solution is conducive to crystal growth, but can also determine the particular concentration or variation of the screening solution at which crystal growth is optimized. This combined screening and optimization approach can greatly decrease the time needed to grow high quality crystals.

As shown in FIG. 16, exemplary crystallization site 1600 includes a structure 1601 defining the sidewalls of the site 1600. Structure 1601 is disposed between an upper and lower film. An array of solutions 1625 is sandwiched between the upper and lower films, and sealed in the site 1600 defined by the structure 1601 and the upper and lower films. Preferably, the upper and lower films have hydrophobic masks that hold the solutions 1625 in place, as illustrated by the one representative mask 1606. The upper film (or optionally, the lower film) contains an active vent 1602 that is normally closed. When a pressure differential is applied across the upper film, vent 1602 opens to allow passage into or out of the site 1600. Although only one vent 1602 is shown in FIG. 16, one of ordinary skill in the art would appreciate that any number of vents could be used in the upper film to enable the desired pumping volume and to adequately remove volatile vapor from all areas of site 1600.

Site 1600 is used in a manner similar to the pumping methods described above. In one embodiment of a method for growing crystals using site 1600, a volume of protein solution is placed in each test location 1625 on the lower film. A volume of screening solution is then placed on or in contact with each of the placed protein solutions, such that the protein and screening solutions form volumes of precipitant solution. Optionally, in forming the volumes of precipitant solution, the protein and screening solutions could be mixed, for example, by stirring with a pipette.

Preferably, the concentration of screening solution at each location 1625 varies, which provides the optimization function described above. With the array of precipitant solutions 1625 deposited on the lower film, the solutions 1625 are then sealed within site 1600 by placing the upper film (and the structure 1601, if it is not already in place) over the lower film. Preferably, the array of solutions 1625 is sandwiched between the upper and lower films, to help contain them and to provide favorable views through which to monitor crystal growth. Optionally, if not already mixed, the protein and screening solutions could be mixed at this point by pressure differential induced movement of the films (as described above).

With the array of solutions 1625 contained within the site 1600 defined by structure 1601 and the upper and lower films, site 1600 is then incubated, during which time volatiles evaporate off of the plurality of solutions 1625. Because of this evaporation, the gas environment within site 1600 accumulates volatile vapor.

After a period of incubation, site 1600 is placed under vacuum. The reduction in ambient pressure to below the pressure within site 1600 causes vent 1602 to open, allowing the accumulated volatile vapor to escape. Preferably, site 1600 is held under vacuum long enough for the pressure in site 1600 to equalize with the lower outside pressure. As pressure equilibrium is reached, vent 1602 closes.

The vacuum is then released from apparatus 1600. Because site 1600 is still under partial vacuum at this point and the pressure outside site 1600 is now greater than the pressure inside, vent 1602 opens and allows ambient air or gas to enter site 1600. The ambient air or gas entering the site 1600 preferably has fewer volatile vapors than the gas pumped out of the site 1600. In an alternative embodiment, instead of simply releasing the vacuum from site 1600 and allowing it to reach standard atmospheric pressure, site 1600 is pressurized to help force ambient air or gas into the site 1600. In either case, once the pressure outside site 1600 equalizes with the pressure inside site 1600, vent 1602 closes and seals site 1600.

With the volatile vapor pumped out of site 1600 and replaced with ambient air or gas, site 1600 is then incubated, during which time further evaporation occurs and additional volatile vapor accumulates in site 1600. The pumping cycle is then repeated at a frequency that provides the desired rate of concentration of the precipitant solutions 1625. To monitor the initial formation of a crystal and/or the crystal growth rate, apparatus 1600 is preferably read between incubation and pumping cycles.

Figure 17A:
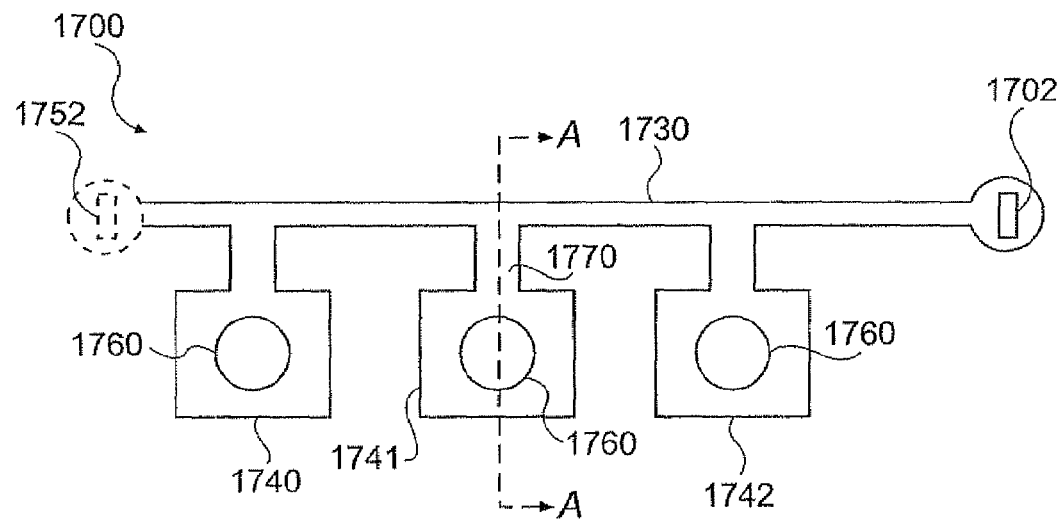
FIG. 17A is a schematic diagram of a plurality of crystallization sites that are connected by a common gas passage from which volatile vapor can be pumped, according to an embodiment of the present invention.

FIG. 17A illustrates a further embodiment of the present invention in which a plurality of crystallization sites is connected by a common gas passage from which volatile vapor can be pumped. As shown in the exemplary apparatus 1700, crystallization sites 1740, 1741, and 1742 are connected to gas passage 1730. The sites 1740, 1741, and 1742 and gas passage 1730 are preferably defined by a structure, such as punched, formed, die-cut, or printed pressure sensitive adhesive, sandwiched between an upper and lower film. A common vent 1702 for sites 1740, 1741, and 1742 is formed in the upper film along gas passage 1730, from which volatile vapor can be pumped. Having a common vent 1702 minimizes the number of vents that must be cut or otherwise formed in the upper film.

FIG. 17B illustrates a cross-sectional view of crystallization site 1741 along line A-A of FIG. 17A, according an embodiment of the present invention. As shown, site 1741 is defined by an upper film 1761 mounted on an upper plate 1769, a layer of glue 1765, and a lower film 1762 mounted on a lower plate 1767. Glue layer 1765 surrounds site 1741 except for the opening 1770, which allows communication with the passage 1730 and vent 1702.

In accordance with an exemplary method for forming crystals using apparatus 1700 of FIG. 17A, a volume of protein solution is first deposited on the lower film at each site 1740, 1741, and 1742, with the upper film not yet covering the sites. A volume of screening solution is then deposited on or in contact with each of the protein solutions so that the two solutions start to mix to form volumes of precipitant solution 1760. Optionally, in forming the volumes of precipitant solution, the protein and screening solutions are mixed, for example, by stirring with a pipette.

The upper film surface (and the sidewall-defining structure, if it is not already in place) is then placed over the lower film. Solutions 1760 are therefore contained within the site 1700 defined by the upper film, the lower film, and the sidewall-defining structure (e.g., a punched, formed, die-cut, or printed pressure sensitive adhesive). Optionally, if not already mixed, the protein and screening solutions could be mixed at this point by movement of the films (as described above). Apparatus 1700 is then incubated, during which time volatiles evaporate off of solutions 1760. As a result of this evaporation, the gas environment within site 1700 accumulates volatile vapor.

After a predetermined period of incubation, apparatus 1700 is placed under vacuum. Consequently, the higher pressure inside gas passage 1730 and sites 1740, 1741, and 1742 forces vent 1702 open, allowing volatile vapor to escape. Preferably, apparatus 1700 is held under vacuum long enough for the pressure in gas passage 1730 and sites 1740, 1741, and 1742 to equalize with the outside vacuum pressure. As pressure equilibrium is reached, vent 1702 closes.

The vacuum is then removed from apparatus 1700. Because gas passage 1730 and sites 1740, 1741, and 1742 are still under partial vacuum at this point and the pressure outside is now greater than the pressure inside, vent 1702 opens and allows ambient air or gas to enter gas passage 1730 and sites 1740, 1741, and 1742. The ambient air or gas entering preferably has fewer volatile vapors than the gas pumped out. In an alternative embodiment, instead of simply releasing the vacuum from apparatus 1700 and allowing it to reach standard atmospheric pressure, apparatus 1700 is pressurized to help force ambient air or gas into gas passage 1730 and sites 1740, 1741, and 1742. In either case, once the pressure outside equalizes with the pressure inside, vent 1702 closes and seals gas passage 1730 and sites 1740, 1741, and 1742.

With the volatile vapor pumped out and replaced with ambient air or gas, apparatus 1700 is then incubated, during which time further evaporation occurs and additional volatile vapor accumulates in gas passage 1730 and sites 1740, 1741, and 1742. The pumping cycle is then repeated at a frequency that provides the desired rate of concentration of precipitant solutions 1760. To monitor the initial formation of a crystal and/or the crystal growth rate, apparatus 1700 is preferably read between incubation and pumping cycles. Having solutions 1760 sandwiched between the upper and lower films improves the efficiency and accuracy of these readings.

Because of the configuration of sites 1740, 1741, and 1742 with respect to vent 1702, it is likely that different amounts of volatile vapor will be removed from the sites. In other words, the greater the distance between a site and vent 1702, the less complete the removal of volatile vapor will likely be. Proportionally fewer volatile vapor will be removed from the sites farthest from vent 1702 than those closer to vent 1702. Thus, in the exemplary configuration of FIG. 17, more volatile vapor will be pumped from site 1742 than site 1741. Likewise, more volatile vapor will be pumped from site 1741 than 1740. These variations will, in turn, affect the rate of concentration of precipitant solution at each site, and correspondingly, the. These variations can therefore be used to control, and perhaps optimize, the initiation of crystallization and the subsequent rate of crystallization, across the various sites. For example, the same concentration of precipitant solution can be placed at each site, and the different rates of concentration provided by the different sites can help determine which rate of concentration initiates crystal growth the fastest.

A further embodiment of the apparatus 1700 of FIG. 17 compensates for variations in the rates of concentration among the sites 1740, 1741, and 1742 by providing another vent 1752 along gas passage 1730. In this manner, volatile vapor can be pumped more evenly from the sites and can escape through both vents 1702 and 1752.

The above-described embodiments involving a single volume of precipitant solution, which includes protein and screening solution, describe the independent placement of the two solutions on the same surface (e.g., on a lower film). In this case, once the two solutions are placed on or in contact with each other, they start to mix. Alternatively, instead of placing the solutions on the same surface, another embodiment places the screening solution on the top of the lower surface and places the protein solution on the bottom of the upper surface. The upper and lower surfaces are then brought together (e.g., as shown in FIG. 12) so that the protein solution and screening solution contact each other and begin to mix. This mixing can be enhanced by providing flexible, moving surfaces (e.g., compliant films) that move the solutions, as shown and described above in reference to FIGS. 14A, 14B, 15A, and 15B. As an alternative, embodiments with less compliant film or rigid films or structures can have the solutions mixed by mechanically moving the top film up and down over the bottom film after the solutions have contacted one another.

Figure 18A:
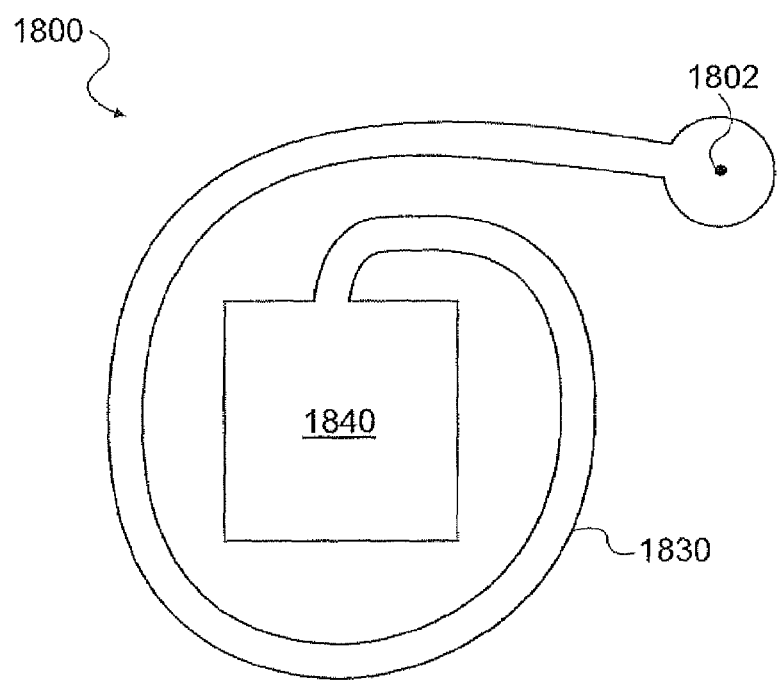
FIG. 18A is a schematic diagram of an exemplary crystallization site having an extended gas passage that is used to control initiation of crystallization and crystal growth rate, according to an embodiment of the present invention.

FIG. 18A illustrates another embodiment of the present invention in which an extended gas passage is used to control the initiation of crystallization, the rate of concentration of a precipitant solution, and the crystal growth rate. As shown, an exemplary apparatus 1800 according to this embodiment includes a crystallization site 1840 connected to a long (in this case, spiral) gas passage 1830 having a termination 1802 at its end opposite the site 1840. Termination 1802 could either be an active (e.g., valve) or passive (e.g., laser ablated hole) vent. The length, cross sections, and volume of gas passage 1830 affect the time needed to allow passive diffusion of (in the case of a passive vent 1802) or to pump (in the case of an active vent 1802) volatile vapor out of site 1840. In one embodiment, the site 1840 and gas passage 1830 are formed by etching a base plate (such as a plastic, metal, or ceramic base plate). An upper film, having termination 1802, is placed over the etched base plate to seal the site 1840 and gas passage 1830.

An extended and constricted gas passage having only a passive termination 1802 can be used to achieve the desired rate of concentration because of its ability to inhibit the rate of vapor diffusion. Additional degrees of control can be achieved by pumping on the passive termination. In other words, pumping can be used to draw volatile vapor out of the open termination 1802. In addition, even more control over rate of concentration can be provided by using an active termination and pumping, in conjunction with an extended gas passage.

Although shown as a spiral in FIG. 18A, gas passage 1830 could, of course, be of any suitable configuration, length, cross section, and volume necessary to achieve the desired rate of concentration of the precipitant solution. In this respect, etching, thermoforming, and adhesive printing are suitable for their flexibility in forming a variety of shapes and sizes.

Figure 18B:
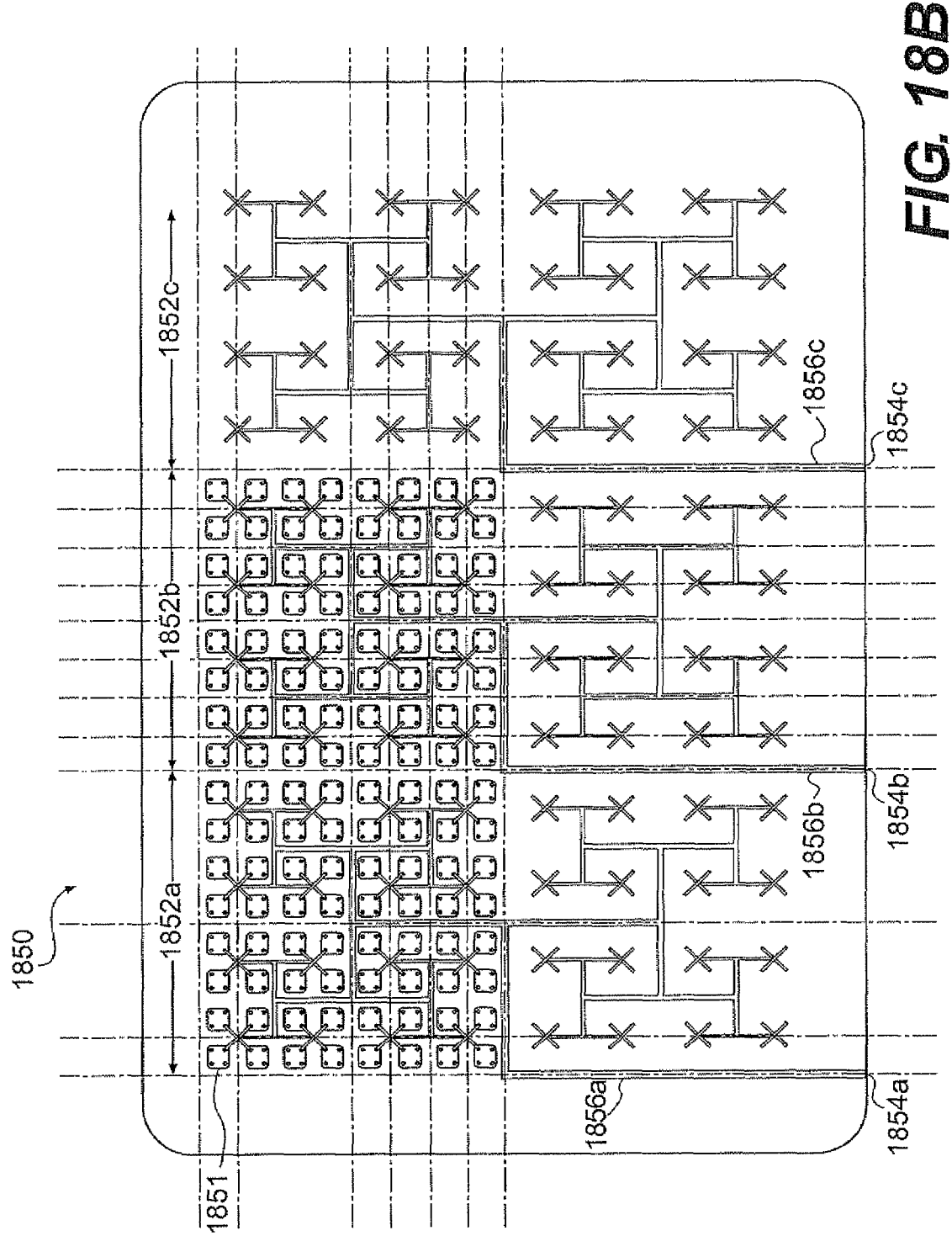
FIG. 18B is a schematic diagram of an exemplary gas passage configuration for a 384-site plate, which is used to control the rate of concentration of precipitant solution in each site, according to an embodiment of the present invention.

FIG. 18B illustrates an exemplary gas passage configuration for a 384-site plate, which is used to control the rate of concentration of precipitant solution in each site, according to an embodiment of the present invention. As shown, the plate 1850 includes three zones 1852a, 1852b, and 1852c of sites 1851, with each zone having 127 sites. For clarity, FIG. 18B shows only a portion of the sites 1851. It should be understood, however, that there would be a complete array of 384 sites 1851 according to this embodiment.

In an embodiment of the present invention, plate 1850 is constructed using a pressure sensitive adhesive sandwiched between a film and a stainless steel plate. The pressure sensitive adhesive (e.g., by printing, forming, die-cutting, or punching) and/or the stainless steel plate (e.g., by etching) could provide the structure defining the sites and passages. In another embodiment, plate 1850 is constructed using a structure (e.g., pressure sensitive adhesive or rigid plate) sandwiched between two films, where the structure defines the sites and passages.

The sites 1851 within a zone are in communication with a common passage terminating at the edge of plate 1850. The sites 1851 of zone 1852a are in communication with termination 1854a through passage 1856a. The sites 1851 of zone 1852b are in communication with termination 1854b through passage 1856b. The sites 1851 of zone 1852c are in communication with termination 1854c through passage 1856c. The terminations 1854a, 1854b, and 1854c can either be active or passive vents.

As shown in FIG. 18B, the gas passages 1856a, 1856b, and 1856c increase in size as they reach their respective terminations 1854a, 1854b, and 1854c. This increase accommodates the accumulated volume of volatile vapor drawn from the sites 1851. As an example, leading from a site 1851, a gas passage could be approximately 0.005 inches deep and 0.010 inches wide, and increase in width incrementally at each juncture up to about 0.050 inches wide where the gas passage meets the termination.

An important aspect of the gas passage configuration shown in FIG. 18B is the uniform vapor diffusion volume it provides for each site. In other words, the volume, as represented by the distance and cross-sectional area of each branch of the gas passage, is the same between each site and the termination. This uniformity, although not required, enables a uniform rate of concentration for each of the precipitant solutions in the sites. Although FIG. 18B shows one type of uniform configuration, one of ordinary skill in the art would understand that other configurations providing the same function are possible. In addition, the sites could be subdivided into fewer or greater numbers of zones than those shown in FIG. 18B.

Figure 19A:
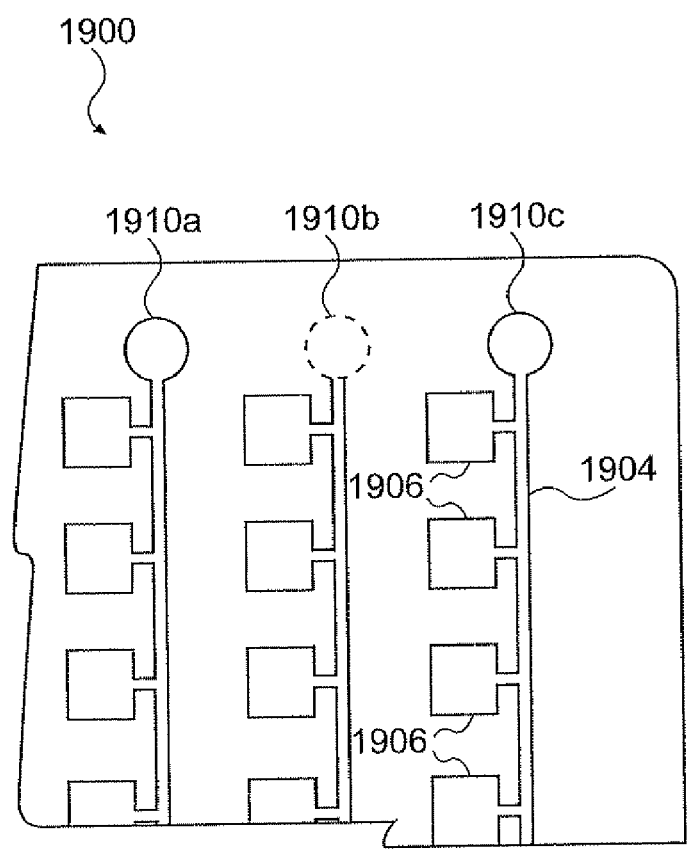
FIG. 19A is a schematic diagram of an exemplary crystallization plate that has a plurality of crystallization sites and can be customized to provide pumping in only a portion of the sites, according to an embodiment of the present invention.

FIG. 19A illustrates a further embodiment of the present invention in which a crystallization plate 1900 having a plurality of crystallization sites can be customized to provide a vent in only a portion of the sites. As shown, plate 1900 includes an array of crystallization sites. Among the plurality of crystallization sites, groups of sites are connected by a gas passage. In the exemplary plate 1900 of FIG. 19A, for example, each column of sites is connected by a common gas passage, such as the gas passage 1904 connecting sites 1906 of the same column. The crystallization plate 1900 is customizable by allowing a user to choose whether a particular gas passage (and therefore its corresponding group of sites) is vented.

To provide this customization, in one embodiment, crystallization plate 1900 is made with a pressure sensitive adhesive sandwiched between an upper and lower film. The lower film provides the surface on which the solutions are deposited. The upper film provides vents that can be selectively applied to the gas passages. The pressure sensitive adhesive can be etched, printed, formed, punched, or die-cut, for example, to define the crystallization sites and gas passages shown in FIG. 19A. The pressure sensitive adhesive is also of a thickness suitable for serving as the sidewalls of the crystallization sites and gas passages.

The pressure sensitive adhesive is etched, printed, or otherwise applied to create through-holes in its structure that correspond to the crystallization sites and gas passages. However, the chambers 1910 over which the vents of the upper film are disposed are not etched through the pressure sensitive adhesive. Instead, these chambers 1910 are perforated. Thus, in assembling plate 1900, a user determines which groups of sites can be pumped by removing the perforated vent chamber 1910 associated with those groups. In this example, the perforated areas 1910a and 1910c have been removed to create vent chambers. On the other hand, the perforated area 1910b has been left on. Thus, crystallization sites in communication with the vent chambers created by the removed perforated areas 1910a and 1910c are pumped, while the sites associated with the perforated area 1910b are not pumped.

Figure 19B:
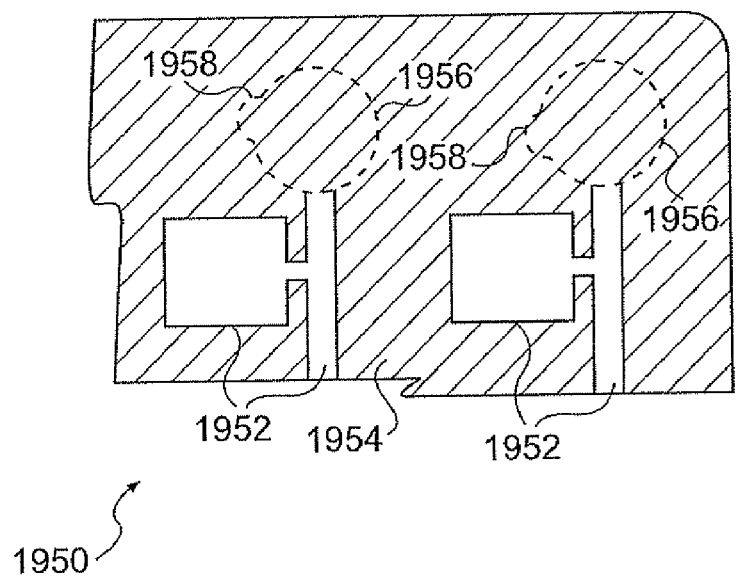
FIG. 19B is a schematic diagram of an exemplary layer of pressure sensitive adhesive that can be customized to provide pumping in only a portion of the sites in a crystallization apparatus, according to an embodiment of the present invention.

FIG. 19B illustrates an exemplary layer 1950 of pressure sensitive adhesive, according to this embodiment of the present invention. The blank areas 1952 indicate where the layer of pressure sensitive adhesive has been etched away or not applied to provide the crystallization sites and gas passages. The crosshatched area 1954 indicates where the pressure sensitive adhesive has not been etched and retains its original thickness. The perforated areas 1956 indicate areas of the pressure sensitive adhesive that a user can remove by, for example, pulling tabs 1958. Removing an area 1956 creates a vent chamber that is in communication with its adjacent gas passage.

The upper film includes a vent aligned over each selectable area 1956. If a selectable area 1956 is removed, then the vent that is aligned with that selectable area 1956 provides a means for pumping the adjacent gas passage and its associated crystallization sites. If a selectable area 1956 is not removed, then the vent that is aligned with that selectable area 1956 rests against the pressure sensitive adhesive of the selectable area and does not serve any pumping function. In this manner, a user can control which groups (in this example, columns) of crystallization sites will be pumped by removing the corresponding selectable areas 1956 of those groups.

Although FIGS. 19A and 19B show selectable areas 1956 associated with a group of sites, the same principal could be applied to individual sites. In other words, a removable area of the pressure sensitive adhesive could be associated with each crystallization site.

In an alternative embodiment, instead of providing removable perforated areas in the pressure sensitive adhesive, a removable material is disposed on top of the upper film, covering a vent. In this configuration, the chamber, gas passage, and/or crystallization site in communication with the vent always remains open (i.e., they do not include removable portions, such as perforated area 1910b of FIG. 19A). For example, for all of the chambers 1910 of FIG. 19A, the pressure sensitive adhesive would be etched through to form the chamber over which the vents are disposed. To provide the selective application of a vent, the vent is covered by a removable material on the top surface of the upper film. In this manner, a user removes the removable material to apply the vent to the chamber. The user is thus able to deposit the precipitant solutions on the lower film, assemble the upper film over the lower film (with the a sidewall structure in between, such as a pressure sensitive adhesive), and then selectively remove the material covering the vents to customize which sites will be subject to pumping.

In addition to opening vents, a further alternative embodiment of the present invention enables a user to close vents to inhibit or stop further vapor diffusion or pumping. For example, a user can place a removable material (e.g., a drop of oil or a film with temporary adhesive, such as that used on Post-It™ notes) or a permanent material (e.g., glue) over a vent. Using a removable material would enable the user to inhibit or stop further concentration of the precipitant solution by applying the removable material over the vent, and then resume concentration when desired by removing the removable material. Thus, for example, in a multiple-site plate, if initial crystal growth is detected in one site, the vent to that one site can be covered to halt her concentration, and the pumping can continue, providing further concentration for the remaining sites.

An important aspect of using pumping to remove volatile vapor is the resultant ability to control concentration rates of the precipitant solution based on the magnitude, duration, frequency, and number of the pumping cycles. The ability to manipulate the concentration rate of the precipitant solution, coupled with the periodic reading of a site, enables a user to control and detect the initiation of crystallization and, subsequently, to control the rate of crystallization and adjust the concentration rate of the precipitant solution to optimize crystal growth. This also helps minimize the over-proliferation of crystals at a site by halting further concentration of the precipitant solution after detection of a crystal.

For example, a site can be pumped at relatively short intervals until a crystal is first detected. At that point, the pumping can be suspended to stop the further concentration of the precipitant solution and inhibit the initiation of more crystals. The rate of crystal growth under non-pumping conditions can be monitored and, if no further crystal growth is detected, the pumping can be re-started and then monitored for its effect on crystal growth and adjusted accordingly.

Therefore, an important aspect of the invention adjusts the pumping, and therefore the rate of concentration of the precipitant solution, in response to the crystal growth detected through regular readings of the sites (e.g., using laser light scattering detection systems). The feedback received from the monitoring is used to adjust the pumping to achieve the desired rate of concentration and the resultant desired effect on crystal initiation and/or subsequent growth.

In another aspect of the present invention, pumping is used not only to remove volatile vapor but also to initiate and control the mixing of a precipitant solution and screening solution, whether the solutions are deposited in contact with each other (as in FIGS. 8F, 9, and 10, for example) or apart (as in FIGS. 8A-8E, for example). The pumping moves the film(s), which moves the solutions, as described above in reference to FIGS. 8c, 14A, 14B, 15A, and 15B. The movement of the film(s) and solutions can therefore control the rate of mixing. This enables the researcher or an automated system to actively mix or allow the solutions to diffuse or a combination of mixing and diffusion with periodic detection to monitor crystal initiation and/or growth. For example, a researcher seeking to optimize the initiation of crystallization can control the pH change caused by the diffusion of the screening solution into the precipitant solution and can determine the particular pH at which crystallization starts.

Figure 20A:
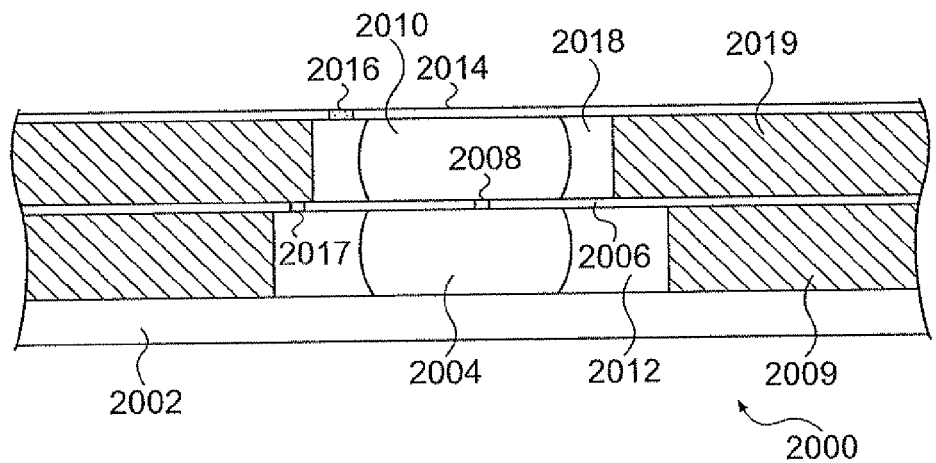
FIG. 20A is a schematic diagram of an exemplary crystallization site in which a screening solution and precipitant solution are separated by a film having an opening through which the screening solution can be pumped to flow into and mix with the precipitant solution, according to an embodiment of the present invention.
Figure 20B:
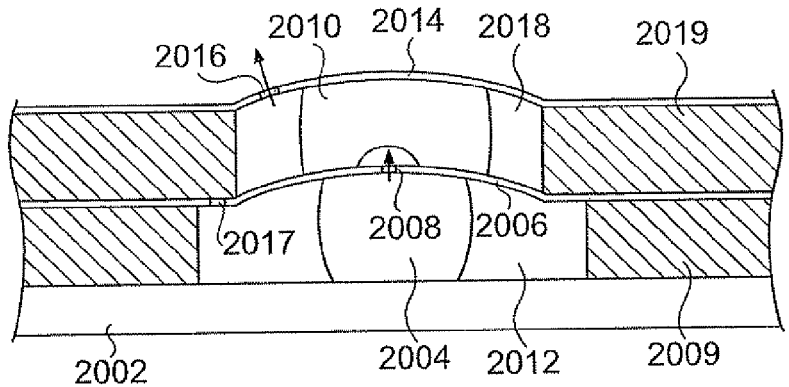
FIG. 20B is a schematic diagram illustrating the crystallization site of FIG. 20A with a pressure differential across the first and second films that allows air and vapor to pass out of the site and screening solution to flow into the precipitant solution.
Figure 20C:
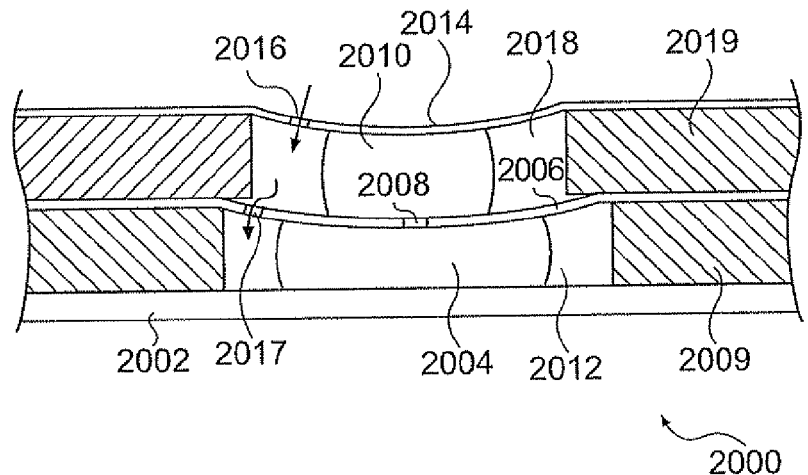
FIG. 20C is a schematic diagram illustrating the crystallization site of FIG. 20A with a pressure differential across the first and second films that allows air to enter the chambers of the site.

FIGS. 20A, 20B, and 20C illustrate a further aspect of control over the mixing and diffusion of a screening solution into a precipitant solution, according to an alternative embodiment of the present invention. In this embodiment, the control is provided by pumping in conjunction with an opening in a film through which the screening solution can be made to flow into the precipitant solution. The opening can be normally closed (e.g., acting as a valve) or always open.

FIG. 20A illustrates an exemplary crystallization site in which a screening solution and precipitant solution are separated by a film having an opening through which the screening solution can be pumped into the precipitant solution and then diffuse into and mix with the precipitant solution, according to an embodiment of the present invention. As shown in FIG. 20A, a crystallization site 2000 according to this embodiment includes a rigid surface 2002 on which a screening solution 2004 is deposited. A compliant film 2006 supported by a plate 2009 is disposed over screening solution 2004, which is sandwiched between rigid surface 2002 and a first side of film 2006.

Film 2006 includes an opening 2008, which can be, for example, a normally closed valve or an always opened hole. The center of screening solution 2004 is preferably roughly coincidental with opening 2008. A precipitant solution 2010 is disposed on the second side of film 2006 opposite the first side. The center of precipitant solution 2010 is preferably roughly coincidental with opening 2008.

A second film 2014 supported by a plate 2019 covers the precipitant solution 2010 to sandwich precipitant solution 2010 between the first film 2006 and the second film 2014. Second film 2014 has an active vent 2016 that is normally closed.

First film 2006 also includes a vent 2017 that is disposed adjacent to support 2019. In this manner, vent 2017 functions as a one-way valve as described above in reference to FIGS. 13B, 13C, and 13D.

In conjunction with pumping, opening 2008 provides control over the rate at which screening solution 2004 flows into precipitant solution 2010. FIGS. 20B and 20C illustrate how the pumping and opening 2008 effect this control over flow and subsequently, diffusion. In particular, a vacuum is applied to site 2000, which creates a pressure differential across first film 2006 and a pressure differential across second film 2014. These pressure differentials cause films 2006 and 2014 to bulge outward as shown in FIG. 20B. The pressure differential across second film 2014 causes vent 2016 to open but vent 2017 to remain closed, and forces or pumps vapor out of chamber 2018 through vent 2016 (as represented by the arrow). The pressure differential across first film 2006 opens opening 2008 (if it is normally closed) and forces screening solution 2004 to flow into precipitant solution 2010 (as represented by the arrow). The duration and depth of the low pressure and the size of opening 2008 determine the volume of screening solution 2004 pumped into precipitant solution 2014.

When the pressure outside site 2000 is returned to the initial pressure or above, films 2006 and 2014 bulge inward and open vents 2016 and 2017, allowing air to pass into chambers 2018 and 2012 (as represented by the arrows), as shown in FIG. 20C. Valve 2008 is also opened, but since it is smaller than valve 2017, and since liquid flows more slowly than gas, the volume of gas entering chamber 2012 is much larger than the volume of liquid entering 2012. Thus, the volume of liquid entering chamber 2012 is less than the volume of screening solution 2004 that exited chamber 2012 in FIG. 20B, thereby providing a net gain of screening solution 2004 flow into the precipitant solution 2010 and into chamber 2018. With each pumping cycle, a greater volume of screening solution 2004 would be disposed in chamber 2018, flowing into and mixing with the precipitant solution 2010.

The magnitude of vacuum, its duration, and the frequency and the number of pumping cycles can be varied to control the rate and volume of flow of the screening solution into the precipitant solution, as well as the rate of concentration of the precipitant solution. The size of valve or opening 2008 can also be varied to control the rate of flow and/or diffusion. Consequently, in controlling the flow and diffusion, this embodiment can control the initiation of crystallization, and, subsequently, the rate at which crystallization continues.

Related to this control, the embodiment of FIG. 20A is also conducive to monitoring and adjusting the control based on feedback received from a detection system. In particular, because crystallization site 2000 sandwiches precipitant solution 2010, the apparatus provides a flat, optically favorable surface through which to detect concentration gradients and crystal initiation and growth. For example, a laser light scattering detection system could be positioned above film 2014 to read precipitant solution 2010. Based on these readings, the pumping could be adjusted to achieve the desired flow, diffusion, mixing, and crystal initiation and growth.

As one of ordinary skill in the art would appreciate, although FIGS. 20A, 20B, and 20C describe surface 2002 as rigid, surface 2002 could also be flexible and still achieve the desired function. In this alternative embodiment, surface 2002 would bend outward (down) in FIG. 20B and inward (up) in FIG. 20C. This movement of surface 2002 may alter the net flow of screening solution 2004 (in comparison to a rigid surface 2002), but otherwise would provide the same functions described above.

In a further aspect of the present invention, in addition to depositing a protein solution and a screening solution at a site, a small starter crystal or starter particle is deposited at the site to initiate crystallization. This approach helps avoid the concurrent growth of multiple crystals at a single site. As an alternative to a starter crystal, plasma treatment of the site, or of a portion of the site, could also be used to initiate crystallization.

Although embodiments of this invention illustrate apparatus having 1, 96, 384, or 1536 test sites, it should be understood that the invention is not limited to any specific number of test sites. For example, the apparatus of the present invention can be configured with any number of test sites (e.g., 6, 12, 24, 48, 96, 384, 1536, 3456, etc.). Indeed, with the embodiment in which two films are used to provide the crystallization chambers, hydrophobic inks on the film can provide a large number of test sites, assuming that the corresponding small sample volumes are possible.

Unlike the crystallization devices of the prior art, the apparatus of the present invention can be used more effectively with an automatic or robotic multi-channel pipetting system that dispenses small sample volumes. The primary reason for this advantage is that, in placing samples of smaller volumes (e.g., below 1 ul), the automatic dispensing systems must physically touch off the surface onto which the sample is being dispensed (to get the sample to release from the pipette). With the prior art crystallization devices, which provide hard surfaces (e.g., polystyrene) onto which to dispense samples, this exercise cannot be accomplished easily, especially when using generic pipette tips, which can vary in length and straightness. Thus, the prior art devices can create undesirable inconsistencies in pipetting or malfunction of the automatic equipment. In contrast, with the present invention, because of the flexibility of the film, pipette tips can be pushed into the surface of the film to ensure touch off at each location. (With such operations, instead of positioning the face of the film perpendicular to the pipette tip(s), it can be desirable to angle the film, e.g., 30 degrees, to help the solution break away.) Thus, the present invention can operate with smaller volumes of protein or other precipitant, which can significantly reduce the cost of growing crystals. Moreover, the present invention is compatible with the robotic systems that dispense these small volumes.

The present invention addresses many of the needs of crystallographers, researchers, and others involved in pharmaceutical structure based drug discovery efforts. The present invention provides a fast, reliable, repeatable, and cost effective solution for screening solutions to find those that will produce crystals of a target compound. Indeed, with the present invention, a user can manually or automatically prepare thousands of experiments a day, using, for example, as little as 1 nl of protein solution per site, and can create reproducible results.

The present invention provides one or more of the following benefits:

1) Experiments can be prepared manually or with a robotic system—provides scalability;
2) Reduced drop size—saves expensive and scarce (e.g., protein) samples and produces results in hours instead of weeks and months;
3) Increased speed—96-site embodiment prepares up to 12,000 experiments per 8 hour day automated/6,000 manually, while the high density embodiments enable four and sixteen fold increases over the 96-site embodiment (with automation);
4) Near-foolproof sealing—eliminates wells lost by uncontrolled evaporation;
5) Smaller reaction chamber—reduces costs associated with reagents and, with high density embodiments, sample volumes are reduced ten- to one thousand-fold;
6) Precision engineered and matched components—ensures proper placement of drops in wells or site locations;
7) Identification markings with pre-printed well location information—eases documentation and viewing of experimental results;
8) Innovative film usage—allows for removal of crystal samples during the experiment for closer examination and the ability to return the sample back to the original site location and reseal without disturbing adjacent sites; and
9) The 384, 1536, and 3456 high-density sandwich drop embodiments enable the use of high speed automated detection systems.

A specific application of the present invention enables a high throughput method for manually or automatically screening solutions for the crystallization of proteins to produce macro molecular crystals.

Although embodiments of the present invention describe the use of protein solutions, one of ordinary skill in the art would appreciate that the present invention is applicable to substances to be crystallized other than proteins, such as polypeptides, viruses, virus particles, and nucleic acids. For this reason, notwithstanding the particular benefits of using the present invention with protein solutions, the present invention should be understood to be broadly applicable to any substance to be crystallized from a precipitant solution.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A crystal forming apparatus comprising:
   a sealed site, wherein an inside pressure exists within the site and an outside pressure exists outside of the site; and
   a vent on the sealed site, wherein the vent is closed when the inside pressure is substantially equal to the outside pressure, and wherein the vent is open when the inside pressure and the outside pressure are substantially different,
   wherein the sealed site comprises a well of a microplate covered by a film, and wherein the vent comprises a slit cut in the film.

2. A crystal forming apparatus comprising:
   a sealed site, wherein an inside pressure exists within the site and an outside pressure exists outside of the site; and
   a vent on the sealed site, wherein the vent is closed when the inside pressure is substantially equal to the outside pressure, and wherein the vent is open when the inside pressure and the outside pressure are substantially different,
   wherein the sealed site has a hydrophobic mask adapted to hold a solution in place.

3. A crystal forming apparatus comprising:
   a sealed site, wherein an inside pressure exists within the site and an outside pressure exists outside of the site; and
   a vent on the sealed site, wherein the vent is closed when the inside pressure is substantially equal to the outside pressure, and wherein the vent is open when the inside pressure and the outside pressure are substantially different,
   wherein the sealed site comprises a sidewall structure sandwiched between a first film and a second film, and wherein the vent comprises a slit cut in the first film.

4. The apparatus of claim 3, wherein the sidewall structure comprises one of a lattice plate having through-holes, a thermoformed lattice plate, and a layer of pressure sensitive adhesive.

5. The apparatus of claim 3, wherein the first film is mounted on the sidewall structure and the second film is mounted on a support structure.

6. The apparatus of claim 3, wherein at least one of the first film and the second film has a hydrophobic mask adapted to hold a solution in place.

7. A crystal forming apparatus comprising:
   a sealed site, wherein an inside pressure exists within the site and an outside pressure exists outside of the site; and
   a vent on the sealed site, wherein the vent is closed when the inside pressure is substantially equal to the outside pressure, and wherein the vent is open when the inside pressure and the outside pressure are substantially different,
   wherein the sealed site has a wall that moves when the inside pressure is substantially different from the outside pressure.

8. The apparatus of claim 7, wherein the wall is made of a compliant film.

9. A crystal forming apparatus comprising:
   a sealed site, wherein an inside pressure exists within the site and an outside pressure exists outside of the site; and
   a vent on the sealed site, wherein the vent is closed when the inside pressure is substantially equal to the outside pressure, and wherein the vent is open when the inside pressure and the outside pressure are substantially different,
   wherein the vent comprises a one-way outlet valve and a one-way inlet valve.

10. The apparatus of claim 9, wherein the one-way outlet valve comprises an outlet wall opening through a first wall of the sealed site and an outlet flap covering the outlet opening on a side of the first wall outside the sealed site, and
    wherein the one-way inlet valve comprises an inlet opening through a second wall of the sealed site and an inlet flap covering the inlet opening on a side of the second wall inside the sealed site.

11. The apparatus of claim 9, wherein the sealed site comprises a support structure sandwiched between a first rigid surface and a second rigid surface, wherein the one-way outlet valve is disposed in one of the first rigid surface and the second rigid surface, and wherein the one-way inlet valve is disposed in one of the first rigid surface and the second rigid surface.

12. A crystal forming apparatus comprising:
    a sealed site, wherein an inside pressure exists within the site and an outside pressure exists outside of the site; and
    a vent on the sealed site, wherein the vent is closed when the inside pressure is substantially equal to the outside pressure, and wherein the vent is open when the inside pressure and the outside pressure are substantially different,
    wherein the sealed site has a hydrophobic mask adapted to hold a plurality of solution apart from each other.

13. The apparatus of claim 12, wherein the sealed site comprises a film on which the hydrophobic mask is disposed.

14. The apparatus of claim 9, wherein the sealed site comprises:
    an upper plate having a through-hole defining the site;
    an upper film bonded to the upper plate, wherein the upper film has an upper opening disposed against a portion of the upper plate, and wherein the upper film is not bonded to the upper plate in an area surrounding the upper opening, such that the area of the upper film surrounding the upper opening can move away from the upper plate and provide communication between the upper opening and the site;
    a lower plate having a through-hole; and
    a lower film bonded to the lower plate, wherein the lower film has a lower opening disposed against a portion of the lower plate, and wherein the lower film is not bonded to the lower plate in an area surrounding the lower opening, such that the area of the lower film surrounding the lower opening can move away from the lower plate and provide communication between the lower opening and the site,
    wherein the upper opening comprises the one-way outlet valve and the lower opening comprises the one-way outlet valve.

15. A crystal forming apparatus comprising:
    a sealed site, wherein an inside pressure exists within the site and an outside pressure exists outside of the site; and
    a vent on the sealed site, wherein the vent is closed when the inside pressure is substantially equal to the outside pressure, and wherein the vent is open when the inside pressure and the outside pressure are substantially different,
    wherein the sealed site comprises a first chamber adapted to hold a precipitant solution and a second chamber adapted to hold a screening solution, and wherein the first chamber and the second chamber are connected by a gas passage.

16. The apparatus of claim 15, wherein the vent is aligned with the first chamber.

17. A crystal forming apparatus comprising:
a sealed site, wherein an inside pressure exists within the site and an outside pressure exists outside of the site; and
a vent on the sealed site, wherein the vent is closed when the inside pressure is substantially equal to the outside pressure, and wherein the vent is open when the inside pressure and the outside pressure are substantially different,
wherein the sealed site has a hydrophobic mask adapted to hold a precipitant solution and a screening solution apart.

18. The apparatus of claim 17, wherein the sealed site comprises a compliant wall adapted to contact the precipitant solution and the screening solution, and
wherein the compliant wall moves in response to a pressure differential between the outside pressure and the inside pressure, to mix the screening solution with the precipitant solution.

19. The apparatus of claim 18, wherein the hydrophobic mask defines a channel between the precipitant solution and the screening solution, the channel providing an area in which the precipitant solution and screening solution contact and mix.

20. A crystal forming apparatus comprising:
a sealed site, wherein an inside pressure exists within the site and an outside pressure exists outside of the site; and
a vent on the sealed site, wherein the vent is closed when the inside pressure is substantially equal to the outside pressure, and wherein the vent is open when the inside pressure and the outside pressure are substantially different,
wherein the sealed site is a first sealed site, and wherein the apparatus further comprises a second sealed site and a gas passage providing communication between the first sealed site and the second sealed site such that first sealed site and the second sealed site are sealed together.

21. The apparatus of claim 20, wherein the vent is disposed in the gas passage.

22. A crystal forming apparatus comprising:
a sealed site, wherein an inside pressure exists within the site and an outside pressure exists outside of the site; and
a vent on the sealed site, wherein the vent is closed when the inside pressure is substantially equal to the outside pressure, and wherein the vent is open when the inside pressure and the outside pressure are substantially different,
wherein the sealed site comprises:
a first film;
an adhesive layer attached to the first film, wherein the adhesive layer defines sidewalls of the sealed site, wherein the adhesive layer includes a removable portion that can be removed to form a chamber sealed along with the sealed site; and
a second film attached to the adhesive layer on a side of the adhesive layer opposite the first film,
wherein the vent is disposed in the second film aligned with the sealed chamber.

23. A crystal forming apparatus comprising:
a sealed site, wherein an inside pressure exists within the site and an outside pressure exists outside of the site;
a vent on the sealed site, wherein the vent is closed when the inside pressure is substantially equal to the outside pressure, and wherein the vent is open when the inside pressure and the outside pressure are substantially different; and
a second vent on the sealed site, wherein the second vent is closed when the inside pressure is substantially equal to the outside pressure, and wherein the second vent is open when the inside pressure and the outside pressure are substantially different.

24. A crystal forming apparatus comprising:
a sealed site, wherein an inside pressure exists within the site and an outside pressure exists outside of the site; and
a vent on the sealed site, wherein the vent is closed when the inside pressure is substantially equal to the outside pressure, and wherein the vent is open when the inside pressure and the outside pressure and substantially different,
wherein the sealed site comprises:
a chamber adapted to receive a solution; and
a gas passage in communication with the chamber on a first end of the gas passage,
wherein the vent is disposed on a second end opposite the first end of the gas passage.

25. The apparatus of claim 24, wherein the gas passage spirals around the chamber.

26. The apparatus of claim 24, further comprising a second sealed site having a second chamber adapted to receive a second solution, wherein the second sealed site is in communication with the first end of the gas passage, and wherein the gas passage increases in size from the first end to the second end.

27. A crystal forming apparatus comprising:
a sealed site, wherein an inside pressure exists within the site and an outside pressure exists outside of the site; and
a vent on the sealed site, wherein the vent is closed when the inside pressure is substantially equal to the outside pressure, and wherein the vent is open when the inside pressure and the outside pressure are substantially different,
wherein the sealed site comprises a sidewall structure sandwiched between a first film and a second film, the sidewall structure comprising a plate with a circular opening, the circular opening defining the sealed site.

28. A crystal forming apparatus comprising:
a first surface; and
an adhesive layer attached to the first surface,
wherein the adhesive layer defines a first plurality of crystallization sites in communication with a first gas passage and a second plurality of crystallization sites in communication with a second gas passage,
wherein the adhesive layer includes a first removable portion that, when removed, provides a first vent chamber in communication with the first gas passage, and
wherein the adhesive layer includes a second removable portion that, when removed, provides a second vent chamber in communication with the second gas passage.

29. The apparatus of claim 28, wherein the first surface is a film.

30. The apparatus of claim 28, wherein the first removable portion includes a tab with which the first removable portion can be pulled off.

31. The apparatus of claim 28, wherein the adhesive layer is perforated to provided the first removable portion and the second removable portion.

32. The apparatus of claim 28, further comprising:
a second surface attached to the adhesive layer on a side of the adhesive layer opposite the first surface;

a first vent disposed in the second surface, wherein the first vent is aligned with the first removable portion if the first removable portion has not been removed and with the first vent chamber if the first removable portion has been removed; and a second vent disposed in the second surface, wherein the second vent is aligned with the second removable portion if the second removable portion has not been removed and with the second vent chamber if the second removable portion has been removed.

33. The apparatus of claim 32, wherein the second surface is a film.

34. The apparatus of claim 33, wherein the second vent is a slit cut into the film.

35. A crystal forming apparatus comprising:
a crystallization site; and
a gas passage in communication with the crystallization site, wherein the gas passage inhibits vapor diffusion from inside the crystallization site to outside the crystallization site, and
wherein the gas passage spirals around the crystallization site.

36. A crystal forming apparatus comprising:
a crystallization site; and
a gas passage in communication with the crystallization site, wherein the gas passage inhibits vapor diffusion from inside the crystallization site to outside the crystallization site, and
wherein the gas passage is a first gas passage, and wherein the apparatus further comprises:
a second crystallization site;
a second gas passage in communication with the second crystallization site, wherein the second gas passage inhibits vapor diffusion from inside the second crystallization site to outside the second crystallization site,
wherein the first gas passage provides a first vapor diffusion volume between the first crystallization site and an ambient gas,
wherein the second gas passage provides a second vapor diffusion volume between the second crystallization site and the ambient gas, and
wherein the first vapor diffusion volume is substantially equal to the second vapor diffusion volume.

37. The apparatus of claim 36, wherein a portion of the first passage is in common with a portion of the second passage.

38. The apparatus of claim 37, wherein the first passage and the second passage increase in cross-sectional area as they extend from the first crystallization site and the second crystallization site, respectively.

39. A crystal forming apparatus comprising:
a crystallization site;
a gas passage in communication with the crystallization site, wherein the gas passage inhibits vapor diffusion from inside the crystallization site to outside the crystallization site; and
an active vent on the gas passage, wherein the active vent is closed when pressure inside the crystallization site is substantially equal to pressure outside the crystallization site, and wherein the active vent is open when the inside pressure and the outside pressure are substantially different.

* * * * *